(12) United States Patent
Schmidt

(10) Patent No.: US 8,951,736 B2
(45) Date of Patent: Feb. 10, 2015

(54) MULTIMER GLYCOSYLATED NUCLEIC ACID BINDING PROTEIN CONJUGATES AND USES THEREOF

(75) Inventor: Karsten Schmidt, San Diego, CA (US)

(73) Assignee: Sequenom, Inc., San Diego, CA (US)

( * ) Notice: Subject to any disclaimer, the term of this patent is extended or adjusted under 35 U.S.C. 154(b) by 0 days.

(21) Appl. No.: 13/456,179

(22) Filed: Apr. 25, 2012

(65) Prior Publication Data

US 2012/0276548 A1 Nov. 1, 2012

Related U.S. Application Data

(60) Provisional application No. 61/480,697, filed on Apr. 29, 2011.

(51) Int. Cl.
  *C12Q 1/68* (2006.01)
  *G01N 33/566* (2006.01)
  *G01N 33/563* (2006.01)
  *G01N 33/53* (2006.01)
  *C07K 14/44* (2006.01)

(52) U.S. Cl.
  CPC ............ *G01N 33/5308* (2013.01); *C07K 14/44* (2013.01)
  USPC .......................... 435/6.19; 435/6.11; 436/501

(58) Field of Classification Search
  CPC . G01N 33/5308; C12Q 2522/10; A61K 31/70
  See application file for complete search history.

(56) References Cited

U.S. PATENT DOCUMENTS

| | | | |
|---|---|---|---|
| 4,391,904 A | 7/1983 | Litman et al. | |
| 4,741,900 A | 5/1988 | Alvarez et al. | |
| 4,946,778 A | 8/1990 | Ladner et al. | |

FOREIGN PATENT DOCUMENTS

| | | |
|---|---|---|
| WO | WO 94/29469 | 12/1994 |
| WO | WO 97/00957 | 1/1997 |
| WO | WO 2006/056480 | 6/2006 |
| WO | WO 2011/127136 | 10/2011 |
| WO | WO 2012/054730 | 4/2012 |
| WO | WO 2012/149047 | 11/2012 |

OTHER PUBLICATIONS

Altschul Nucl. Acids Res. 25 (1977), 3389-3402.
Altschul, J. Mol. Biol. 215 (1990), 403-410.
Altschul, J. Mol. Evol. 36 (1993), 290-300.
Anderson, Science 256 (1992), 808- 813.
Ausubel, "Current Protocols in Molecular Biology", Green Publishing Associates and Wiley Interscience, N.Y. (1989).
Biocomputing: lnfoliuaties and Genome Projects, Smith, DM., ed., Academic Press, New York, 1994.
Bowie, Science 247: (1990) 1306-1310.
Brutlag et al., "Improved sensitivity of biological sequence database searches," CABIOS 6 (1990), 237-245.
Computational Molecular Biology, Lesk, A.M., ed., Oxford University Press, New York, 1988.
Cross et al., "The modified base J is the target for novel DNA binding protein in Kinetoplastid Protazoans," (1999) EMBO J. 18:6573-6581.
Cunningham and Wells, Science 244: (1989) 1081-1085.
Davis et al., "Basic methods in molecular biology", Davis LG, Dibmer MD, Battey Elsevier (1986).
Dayhoff et al., "A Model of Evolutionary Change in Proteins," Atlas of Protein Sequence and Structur3, Chapter 22: 345-352, Nat. Biomed. Res. Foundation, Washington, D. C. (1978).
Giordano, Nature Medicine 2 (1996), 534-539.
Grover et al., (2007) Angew Chem. Int. Ed. Engl. 46:2839-2843.
Hames and Higgins (Eds.) "Nucleic acid hybridization, a practical approach" IRL Press Oxford, Washington DC, (1985).
Harlow and Lane "Antibodies, A Laboratory Manual", CSH Press, Cold Spring Harbor, 1988.
Heidebrecht et al., "The Structural basis for recognition of base J containing DNA by a novel DNA binding domain in JBP1,"Nucleic Acids Research, vol. 39, No. 13, Mar. 16, 2011, pp. 5715-5728.
Henikoff Proc. Natl. Acad. Sd., USA, 89, (1989), 10915.
Houghton Proc. Natl. Acad. Sci. USA (82) (1985), 5131-5135.
Isner, Lancet 348 (1996), 370-374.
Kohler and Milstein Nature 256 (1975), 495-497.
Kozbor, "The production of monoclonal antibodies from human lymphocytes," Immunology Today 4 (1983), 72-79.
Malmborg, J. Immunol. Methods 183 (1995), 7-13.
Mayer, (Eds) "Immunochemical methods in cell and molecular biology" Academic Press, London (1987).
Merrifield et al. (1969) "Solid Phase Peptide Synthesis I. The Synthesis of a Tetrapeptide," J. Am. Chem. Soc. 85 (1963), 2149-2154.
Miller (1993), "Baculoviruses: high-level expression in insect cells," Curr. Op. Genet. Dev., 3, 97-101.
Muhlhauser, Circ. Res. 77 (1995), 1077-1086.
Needleman, J. Mol Biol. 48 (1970): 443- 453.
Owens, Proc. Natl. Acad. Sci. USA 98 (2001), 1471-1476.

(Continued)

Primary Examiner — Shafiqul Haq
(74) Attorney, Agent, or Firm — Grant IP, Inc.

(57) ABSTRACT

The technology relates in part to multimer conjugates comprising a scaffold linked to two or more polypeptides that specifically interact with a nucleic acid containing beta-D-glucosyl-hydroxymethylcytosine or beta-D-glucosyl-hydroxymethyluracil. The scaffold can be chosen from an antibody, an antibody fragment, a multimerized binding partner that interacts with a binding partner counterpart in each of the polypeptides, a polymer, and a polyfunctional molecule. The polypeptides can be from a kinetoplastid flagellate organism and may comprise a full-length native or modified protein or a fragment thereof that specifically interacts with the beta-D-glucosyl-hydroxymethylcytosine and/or the beta-D-glucosyl-hydroxymethyluracil in the nucleic acid. The conjugates provided herein can be used to detect the presence, absence or amount of beta-D-glucosyl-hydroxymethylcytosine and/or beta-D-glucosyl-hydroxymethyluracil-containing nucleic acid in a sample.

13 Claims, 1 Drawing Sheet

(56) References Cited

OTHER PUBLICATIONS

Rattan, Ann. NY Acad. Sci. 663 (1992); 48-62.
Robertson et al., "A novel method for the efficient and selective identification of 5-hydroxymethylcytosine in genomic DNA," Nucleic Acids Res. Apr. 1, 2011;39(8):e55.1-e55.10.
Sabatini et al., "Site-specific Interactions of JBP with Base and Sugar Moieties in Duplex J-DNA, Evidence for Both Major and Minor Groove Contacts," (2002) J. Biol. Chem. 277: 28150-28156.
Sabatini et al., (2002) J. Biol. Chem. 277:958-966.
Sambrook, Russell "Molecular Cloning, A Laboratory Manual", Cold Spring Harbor Laboratory, N.Y. (2001).
Schaper, Circ. Res. 79 (1996), 911-919.
Schaper, Current Opinion in Biotechnology 7 (1996), 635-640.
Schier, "Efficient in vitro affinity maturation of phage antibodies using BIAcore guided selections," Human Antibodies Hybridomas 7 (1996), 97-105.
Seifter, "Analysis for Protein Modifications and Nonprotein Cofactors," Meth. Enzymol. 182 (1990); 626-646.
Sequence Analysis in Molecular Biology, von Heinje, G., Academic Press, 1987.
Sequence Analysis Primer, Gribskov, M. And Devereux, eds., M Stockton Press, New York, 1991.
Shopes, "A Genetically Engineered Human IgG Mutant with Enhanced Cytolytic Activity," J Immunol. May 1, 1992;148(9):2918-2922.
Thompson Nucl. Acids Res. 2 (1994), 4673-4680.
Tijssen, "Practice and theory of enzyme immunoassays", Burden and von Knippenburg (Eds), vol. 15 (1985).
Verma, Nature 389 (1997), 239-242.
Wang, Nature Medicine 2 (1996), 714-716.
International Search Report and Written Opinion dated: Sep. 3, 2012 in International Application: PCT/US2012/035037 filed Apr. 25, 2012 and published as: WO 12/149047 on Nov. 1, 2012.

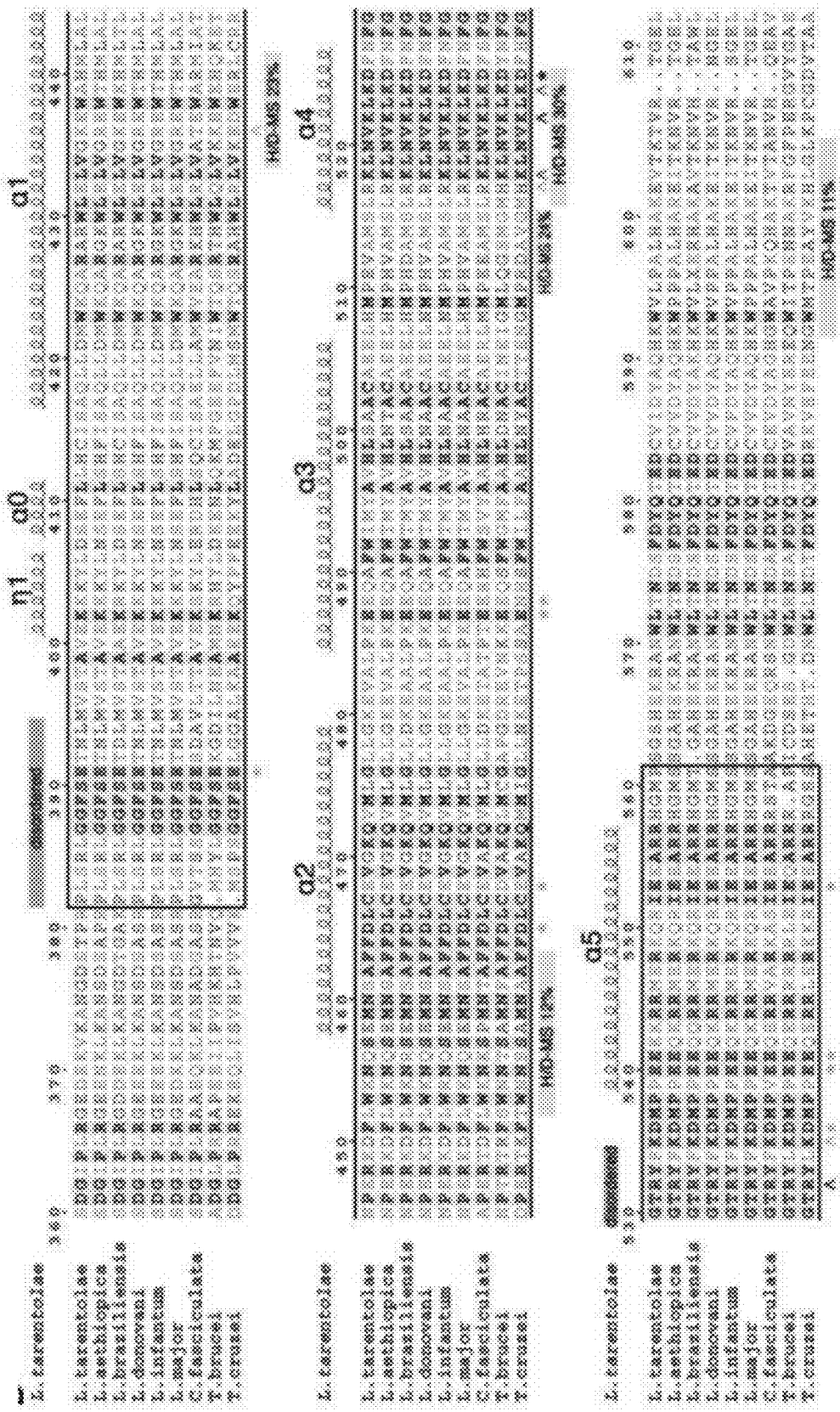

SEQUENCE LISTING

<160> NUMBER OF SEQ ID NOS: 21

<210> SEQ ID NO 1
<211> LENGTH: 827
<212> TYPE: PRT

-continued

<213> ORGANISM: Leishmania tarentolae

<400> SEQUENCE: 1

```
Met Glu Pro Asp Ser Lys Lys Val Lys Leu Asp Ile Phe Asn Phe Pro
1               5                   10                  15

Thr Thr Arg Glu Thr Arg Thr Pro Glu Glu Val Ala Glu Ser Tyr Ala
            20                  25                  30

Glu Ala Val Lys Ser His Pro Phe Tyr Asp Asn Val His Ser Val Val
        35                  40                  45

Asp Phe Tyr Asp Ser Gly Thr Ile Lys Asp Gly Arg Gly Gln Ile Ile
    50                  55                  60

Gly Val Val Leu Arg Glu Ala Leu Pro Lys Tyr Ala Ala Ser Met Ala
65                  70                  75                  80

Ser Glu Leu Leu Thr Ser Ala Ala Val Arg Thr Ser Leu Arg Ser Met
                85                  90                  95

Met Phe Gly Gly Glu Pro Pro Leu Ser Gly Ile Ala Gly Tyr Phe Asp
            100                 105                 110

Tyr Arg Gly Ser Pro Val Glu Leu Lys Ser Arg Lys Thr Ser Phe Thr
        115                 120                 125

Tyr Glu His Glu Ala Ala Trp Pro Ala Val Phe Pro Val Val Asp Tyr
    130                 135                 140

Val Ser Glu Ile Tyr Arg His Val Ala Pro Glu Arg Trp Lys Ala Gln
145                 150                 155                 160

Asn Asp Ala Ile Pro Asp Leu Val Arg Ile His Gly Thr Pro Phe Ser
                165                 170                 175

Thr Leu Thr Ile Asn Ser Arg Phe Arg Thr Ala Ser His Thr Asp Val
            180                 185                 190

Gly Asp Phe Asp Ala Gly Tyr Ser Cys Ile Ala Cys Leu Asp Gly Gln
        195                 200                 205

Phe Lys Gly Leu Ala Leu Ser Phe Asp Asp Phe Gly Ile Asn Val Leu
    210                 215                 220

Leu Gln Pro Arg Asp Val Met Ile Phe Asp Ser His His Phe His Ser
225                 230                 235                 240

Asn Thr Glu Val Glu Leu Ser Phe Ser Gly Asp Trp Lys Arg Leu
                245                 250                 255

Thr Cys Val Phe Tyr Tyr Arg Ala Ala Leu Gly Glu Pro Ala Ser Tyr
            260                 265                 270

Ala Glu Tyr Gln Arg Arg Leu Glu Lys Ser Lys Thr Asp Thr Arg Phe
        275                 280                 285

Thr Pro Val His His Val Arg Val Lys Glu Asn Gly Thr Ser Val
    290                 295                 300

Asn Arg Pro Ser Pro Val Tyr Pro Ile Ser Gln Ser Pro Phe Trp Val
305                 310                 315                 320

Pro Met Val Ala His Cys Leu Gln His Cys Ala Ser Ala Gln Cys
                325                 330                 335

Val His Glu Ala Met Thr Ala Asp Gly Ser Arg Leu Ala Glu Met Met
            340                 345                 350

Phe Gly Glu Ser Leu Ser Thr Ser Asp Gly Ile Pro Leu Arg Gly Glu
        355                 360                 365

Asp Glu Lys Val Lys Ala Asn Gly Asp Ser Thr Pro Arg Pro Leu Ser
    370                 375                 380

Arg Leu Gly Gly Phe Ser Glu Thr Asn Leu Met Val Ser Thr Ala Val
385                 390                 395                 400
```

```
Glu Lys Lys Lys Tyr Leu Asp Ser Glu Phe Leu Leu His Cys Ile Ser
                405                 410                 415

Ala Gln Leu Leu Asp Met Trp Lys Gln Ala Arg Ala Arg Trp Leu Glu
            420                 425                 430

Leu Val Gly Lys Glu Trp Ala His Met Leu Ala Leu Asn Pro Glu Arg
        435                 440                 445

Lys Asp Phe Leu Trp Lys Asn Gln Ser Glu Met Asn Ser Ala Phe Phe
    450                 455                 460

Asp Leu Cys Glu Val Gly Lys Gln Val Met Leu Gly Leu Leu Gly Lys
465                 470                 475                 480

Glu Val Ala Leu Pro Lys Glu Glu Gln Ala Phe Trp Ile Met Tyr Ala
                485                 490                 495

Val His Leu Ser Ala Ala Cys Ala Glu Glu Leu His Met Pro Glu Val
            500                 505                 510

Ala Met Ser Leu Arg Lys Leu Asn Val Lys Leu Lys Asp Phe Asn Phe
        515                 520                 525

Gly Gly Thr Arg Tyr Phe Lys Asp Met Pro Glu Glu Lys Lys Arg
    530                 535                 540

Arg Met Glu Arg Lys Gln Arg Ile Glu Glu Ala Arg Arg His Gly Met
545                 550                 555                 560

Pro Ser Gly Ser His Glu Lys Arg Ala Asn Trp Leu Thr Asn Asp Ser
                565                 570                 575

Phe Asp Tyr Gln Thr Glu Asp Cys Val Ile Asp Tyr Ala Gln His Lys
            580                 585                 590

Trp Val Leu Pro Ala Leu His Ala Lys Glu Val Thr Lys Thr Val Arg
        595                 600                 605

Thr Gly Glu Leu Pro Thr Thr Glu Arg Val Val Arg Val Leu Val Val
    610                 615                 620

Ile Pro Asp Pro Gln Ser Lys Leu Glu Asn Val Asp Cys Lys Leu Glu
625                 630                 635                 640

Val Pro Asp Met Val Gly Ser Ser Ser Glu Trp Glu Arg Leu Met Ser
                645                 650                 655

Ser Pro Ala Val His Arg Val Leu Ser Ala Ala Gln Arg Asn Leu Gln
            660                 665                 670

Leu Pro Asp Ser Val Thr His Gly Asn Val Gln Thr His Phe Ala Phe
        675                 680                 685

His Ser Thr Leu Pro Thr Asp Ile Tyr Asp Phe Val Val Leu Gln His
    690                 695                 700

Val Leu Ser Arg Ile Pro Asp Ala Gln Ala Ser Ala Tyr Ile Arg
705                 710                 715                 720

Arg Ala Ala Ala Leu Cys Ser Gly Cys Leu Phe Val Val Glu Thr Asp
                725                 730                 735

Val Gln Cys Arg Gln Tyr Tyr Thr Leu Lys Tyr Ser Ile Arg Cys Ser
            740                 745                 750

Tyr Asp Thr Val Ala Pro Leu Phe Phe Gln Leu His Arg Val Cys
        755                 760                 765

Tyr Gly Thr Lys Thr Ala Arg Val Arg Thr Lys Gly Glu Leu Glu Ser
    770                 775                 780

Leu Ile Pro Thr Val Cys Cys Ala Arg Tyr Lys Leu Gln Gly Ser Pro
785                 790                 795                 800

Leu Asn Thr Thr Val His Val Val Ser Pro Phe Pro Ser Cys Glu Val
                805                 810                 815

Gln Asn Leu Ser Ser Ala Leu Cys Asp Arg Ala
```

```
                   820                 825

<210> SEQ ID NO 2
<211> LENGTH: 253
<212> TYPE: PRT
<213> ORGANISM: Leishmania aethiopica

<400> SEQUENCE: 2

Ser Asp Gly Ile Pro Leu Arg Gly Glu Glu Asn Lys Leu Lys Ala Asn
1               5                   10                  15

Ser Asp Ser Ala Pro Arg Pro Leu Ser Arg Leu Gly Gly Phe Ser Glu
            20                  25                  30

Thr Asn Leu Met Val Ser Thr Ala Val Glu Lys Lys Tyr Leu Asn
        35                  40                  45

Ser Glu Phe Leu Ser His Phe Ile Ser Ala Gln Leu Leu Asp Met Trp
50                  55                  60

Lys Gln Ala Arg Gly Lys Trp Leu Glu Leu Val Gly Arg Glu Trp Thr
65                  70                  75                  80

His Met Leu Ala Leu Asn Pro Glu Arg Lys Asp Phe Leu Trp Lys Asn
                85                  90                  95

Gln Ser Glu Met Asn Ser Ala Phe Phe Asp Leu Cys Glu Val Gly Lys
            100                 105                 110

Gln Val Met Leu Gly Leu Leu Gly Lys Glu Val Ala Leu Pro Lys Glu
        115                 120                 125

Glu Gln Ala Phe Trp Thr Met Tyr Ala Val His Leu Asn Thr Ala Cys
130                 135                 140

Ala Glu Glu Leu His Met Pro His Val Ala Met Ser Leu Arg Lys Leu
145                 150                 155                 160

Asn Val Lys Leu Lys Asp Phe Asn Phe Gly Gly Thr Arg Tyr Phe Lys
                165                 170                 175

Asp Met Pro Pro Glu Glu Gln Lys Arg Arg Met Glu Arg Lys Gln Arg
            180                 185                 190

Ile Glu Glu Ala Arg Arg His Gly Met Ser Ser Gly Ala His Glu Lys
        195                 200                 205

Arg Ala Asn Trp Leu Thr Asn Asp Ser Phe Asp Tyr Gln Thr Glu Asp
    210                 215                 220

Cys Val Asp Tyr Ala Gln His Lys Trp Pro Pro Ala Leu His
225                 230                 235                 240

Ala Arg Glu Ile Thr Lys Asn Val Arg Thr Gly Glu Leu
                245                 250

<210> SEQ ID NO 3
<211> LENGTH: 813
<212> TYPE: PRT
<213> ORGANISM: Leishmania braziliensis

<400> SEQUENCE: 3

Met Glu Ser Ser Thr Lys Arg Ile Lys Met Asp Ile Phe Asn Phe Pro
1               5                   10                  15

Thr Ile Lys Glu Thr Arg Thr Pro Glu Glu Val Ala Glu Ser Tyr Ala
            20                  25                  30

Glu Ala Val Lys Leu His Pro Phe Tyr Asp Asn Ala His Cys Val Ile
        35                  40                  45

Asp Phe Tyr Asp Ser Gly Thr Ile Lys Asp Gly Arg Gly Glu Ile Ile
    50                  55                  60

Gly Val Val Leu Arg Lys Ala Leu Pro Lys Tyr Ala Thr Ser Met Ala
```

```
                65                  70                  75                  80
        Ser Ala Leu Leu Ile Ser Ala Ala Val Arg Thr Ser Leu Arg Ser Met
                        85                  90                  95
        Ile Phe Gly Gly Glu Ser Pro Leu Ser Gly Ile Ala Gly Tyr Phe Asp
                       100                 105                 110
        Tyr Arg Gly Ser Pro Val Glu Leu Lys Ser Arg Lys Thr Ser Phe Thr
                       115                 120                 125
        Tyr Glu His Glu Glu Ala Trp Ser Ala Val Phe Pro Val Val Asp Tyr
                       130                 135                 140
        Val Ser Glu Ile Tyr Arg His Val Ala Pro Glu Arg Trp Lys Ala Gln
        145                 150                 155                 160
        Asn Asn Ala Ile Pro Asp Leu Val Arg Ile His Gly Thr Pro Phe Ser
                       165                 170                 175
        Thr Leu Thr Ile Asn Ser Arg Phe Arg Thr Ala Ser His Thr Asp Val
                       180                 185                 190
        Gly Asp Phe Asp Ala Gly Tyr Ser Cys Ile Ala Cys Ile Asp Gly Lys
                       195                 200                 205
        Phe Lys Gly Leu Ala Leu Thr Phe Asp Asp Phe Arg Ile Asn Val Leu
                       210                 215                 220
        Met Gln Pro Arg Asp Val Met Val Phe Asp Ser His His Phe His Ser
        225                 230                 235                 240
        Asn Thr Glu Val Glu Val Ser Cys Ser Glu Glu Asp Trp Lys Arg Leu
                       245                 250                 255
        Thr Cys Val Phe Tyr Tyr Arg Thr Ala Leu Gly Glu Pro Ser Ser Tyr
                       260                 265                 270
        Ala Glu Tyr Arg Arg Arg Leu Glu Lys Ser Lys Gln Asp Pro Ser Phe
                       275                 280                 285
        Thr Pro Val Val Ser Asn Val Met Met Lys Glu Asn Gly Thr Asn Leu
                       290                 295                 300
        Asn Arg Pro Ser Pro Val His Pro Val Pro Pro Ser Pro Phe Trp Leu
        305                 310                 315                 320
        Pro Met Leu Ala His Cys Leu Gln His Cys Ala Ser Ala Ala Gln Ser
                       325                 330                 335
        Val His Glu Ala Met Thr Ala Asp Gly Ser Gln Leu Ala Glu Ile Ile
                       340                 345                 350
        Phe Gly Glu Pro Leu Ser Thr Ser Asp Gly Ile Pro Leu Arg Gly Asp
                       355                 360                 365
        Asp Glu Lys Leu Lys Ala Asn Gly Asp Thr Gly Ala Lys Pro Leu Ser
                       370                 375                 380
        Arg Leu Gly Gly Phe Ser Glu Thr Asp Leu Met Val Ser Thr Ala Ala
        385                 390                 395                 400
        Glu Lys Arg Lys Tyr Leu Asp Ser Glu Phe Leu Ser His Cys Ile Ser
                       405                 410                 415
        Ala Gln Leu Leu Asp Met Trp Lys Gln Ala Arg Ala Arg Trp Leu Glu
                       420                 425                 430
        Leu Val Gly Lys Glu Trp Lys His Met Leu Thr Leu Asn Pro Glu Arg
                       435                 440                 445
        Lys Asp Phe Leu Trp Lys Asn Arg Ser Glu Met Asn Ser Ala Phe Phe
                       450                 455                 460
        Asp Leu Cys Glu Val Gly Lys Gln Val Met Leu Gly Leu Leu Asp Lys
        465                 470                 475                 480
        Glu Ala Ala Leu Pro Lys Glu Glu Gln Ala Phe Trp Thr Met Tyr Ala
                       485                 490                 495
```

Val His Leu Ser Ala Ala Cys Ala Glu Glu Leu His Met Pro His Asp
        500                 505                 510

Ala Met Ser Leu Arg Lys Leu Asn Val Lys Leu Lys Asp Phe Asn Phe
        515                 520                 525

Gly Gly Thr Arg Tyr Phe Lys Asp Met Pro Pro Glu Glu Gln Gln Arg
        530                 535                 540

Arg Met Glu Arg Lys Gln Arg Ile Glu Glu Ala Arg Arg His Gly Met
545                 550                 555                 560

Thr Gly Ala His Glu Lys Arg Ala Asn Trp Leu Thr Asn Asp Ser Phe
                565                 570                 575

Asp Tyr Gln Thr Glu Asp Cys Val Val Asp Tyr Ala Lys His Lys Trp
                580                 585                 590

Val Leu Pro Glu Arg His Ala Lys Ala Val Thr Lys Asn Val His Thr
                595                 600                 605

Ala Trp Leu Pro Thr Arg Glu Glu Val Val Arg Val Leu Val Val Leu
        610                 615                 620

Pro Asp Leu Gln Ile Arg Val Glu Gly Val Asp Cys Lys Leu Glu Lys
625                 630                 635                 640

Pro Asp Thr Val Glu Asp Ser Ser Glu Trp Val Arg Leu Val Ser Ser
                645                 650                 655

Pro Ala Val His Arg Leu Leu Ala Ala Ala Gln Arg Asn Leu Gln Leu
                660                 665                 670

Pro Asp Asp Val Met His Gly Asn Ile His Ile Arg Phe Val Phe His
                675                 680                 685

Ser Thr Leu Pro Thr Asp Met Tyr Asp Phe Val Val Leu Gln His Val
        690                 695                 700

Leu Ser Arg Ile Pro Asp Asp Val Leu Ala Ser Ser Tyr Ile Thr Arg
705                 710                 715                 720

Ala Ala Ala Leu Cys Ser Gly Cys Leu Phe Val Glu Glu Thr Asp Val
                725                 730                 735

Gln Cys Arg Gln Tyr Tyr Thr Leu Lys Tyr Ser Ile Arg Arg Asn Tyr
                740                 745                 750

Asp Ala Val Ala Pro His Phe Phe Gln Gln Leu His Gln Ala Ser Tyr
                755                 760                 765

Gly Thr Lys Met Ala Arg Val Arg Thr Lys Gly Glu Leu Glu Ala Leu
        770                 775                 780

Ile Pro Thr Val Cys Cys Ala Arg Tyr Lys Leu Gln Gly Ser Pro Leu
785                 790                 795                 800

Asn Thr Thr Ile His Val Val Ser Pro Thr Ala Pro His
                805                 810

<210> SEQ ID NO 4
<211> LENGTH: 814
<212> TYPE: PRT
<213> ORGANISM: Leishmania donovani

<400> SEQUENCE: 4

Met Glu Pro Asp Pro Lys Lys Val Lys Leu Asp Ile Phe Asp Phe Pro
1               5                   10                  15

Thr Ala Arg Glu Thr Arg Thr Pro Glu Glu Val Ala Glu Ser Tyr Ala
                20                  25                  30

Glu Ala Val Lys Ser His Pro Phe Tyr Asp Asn Val His Ser Ala Ile
        35                  40                  45

Asp Phe Tyr Asp Ser Gly Thr Ile Lys Asp Gly Arg Gly Gln Ile Ile

```
                50                  55                  60
Gly Val Val Leu Arg Glu Ala Leu Pro Lys Tyr Ala Ala Ser Met Ala
65                  70                  75                  80

Ser Glu Leu Leu Ala Ser Ala Val Arg Thr Ser Leu Arg Ser Met
                85                  90                  95

Met Phe Gly Gly Glu Ser Pro Leu Ser Gly Ile Ala Gly Tyr Phe Asp
                100                 105                 110

Tyr Arg Gly Ser Pro Val Glu Leu Lys Ser Arg Lys Thr Ser Phe Thr
                115                 120                 125

Tyr Glu His Glu Ala Ala Trp Pro Ala Val Phe Pro Val Val Asp Tyr
                130                 135                 140

Val Ser Glu Leu Tyr Arg His Val Ala Pro Glu Arg Trp Lys Ala Gln
145                 150                 155                 160

Asn Asp Ala Ile Pro Asp Val Val Arg Ile His Gly Thr Pro Phe Ser
                165                 170                 175

Thr Leu Thr Ile Asn Ser Arg Phe Arg Thr Ala Ser His Thr Asp Val
                180                 185                 190

Gly Asp Phe Asp Gly Gly Tyr Ser Cys Ile Ala Cys Leu Asp Gly Gln
                195                 200                 205

Phe Lys Gly Leu Ala Leu Ala Phe Asp Asp Phe Gly Ile Asn Val Leu
                210                 215                 220

Met Gln Pro Arg Asp Val Met Ile Phe Asp Ser His His Phe His Ser
225                 230                 235                 240

Asn Thr Glu Val Glu Leu Ser Phe Ser Gly Glu Asp Trp Lys Arg Leu
                245                 250                 255

Thr Cys Val Phe Tyr Tyr Arg Ala Ala Leu Gly Glu Pro Ala Ser Tyr
                260                 265                 270

Ala Glu Tyr Arg Arg Arg Leu Glu Lys Ser Lys Gln Asp Thr Ser Phe
                275                 280                 285

Thr Pro Val Val Ser Asn Val Arg Val Lys Glu Asn Gly Thr Asn Leu
                290                 295                 300

Asn Arg Pro Ser Pro Val Tyr Pro Ile Phe Leu Ser Pro Phe Trp Val
305                 310                 315                 320

Pro Met Val Ala His Cys Leu Gln His Cys Ala Ser Glu Ala Gln Cys
                325                 330                 335

Val His Asp Ala Met Thr Ala Asp Gly Ser Arg Leu Ala Glu Val Met
                340                 345                 350

Phe Gly Glu Pro Leu Ser Thr Ser Asp Gly Ile Pro Leu Arg Gly Glu
                355                 360                 365

Glu Glu Lys Leu Lys Ala Asn Ser Asp Ser Ala Ser Arg Pro Leu Ser
                370                 375                 380

Arg Leu Gly Gly Phe Ser Glu Thr Asn Leu Met Val Ser Thr Ala Val
385                 390                 395                 400

Glu Lys Lys Lys Tyr Leu Asn Ser Glu Phe Leu Ser His Phe Ile Ser
                405                 410                 415

Ala Gln Leu Leu Asp Met Trp Lys Gln Ala Arg Gly Lys Trp Leu Glu
                420                 425                 430

Leu Val Gly Arg Glu Trp Thr His Met Leu Ala Leu Asn Pro Glu Arg
                435                 440                 445

Lys Asp Phe Leu Trp Lys Asn Gln Ser Glu Met Asn Ser Ala Phe Phe
                450                 455                 460

Asp Leu Cys Glu Val Gly Lys Gln Val Met Leu Gly Leu Leu Gly Lys
465                 470                 475                 480
```

```
Glu Ala Ala Leu Pro Lys Glu Gln Ala Phe Trp Thr Met Tyr Ala
                485                 490                 495

Val His Leu Asn Ala Ala Cys Ala Glu Leu Asn Met Pro His Val
            500                 505                 510

Ala Met Ser Leu Arg Lys Leu Asn Val Lys Leu Lys Asp Phe Asn Phe
        515                 520                 525

Gly Gly Thr Arg Tyr Phe Lys Asp Met Pro Glu Glu Gln Lys Arg
        530                 535                 540

Arg Met Glu Arg Lys Gln Arg Ile Glu Glu Ala Arg Arg His Gly Met
545                 550                 555                 560

Ser Ser Gly Ala His Glu Lys Arg Ala Asn Trp Leu Thr Asn Asp Ser
                565                 570                 575

Phe Asp Tyr Gln Thr Glu Asp Cys Val Val Asp Tyr Ala Gln His Lys
                580                 585                 590

Trp Val Pro Pro Ala Leu His Ala Lys Glu Ile Thr Lys Asn Val Arg
                595                 600                 605

Ser Gly Glu Leu Pro Thr Arg Glu Gly Val Val Arg Val Leu Val Val
            610                 615                 620

Leu Pro Asp Pro Gln Ser Lys Val Asp Cys Val Asp Cys Lys Leu Glu
625                 630                 635                 640

Val Ser Glu Thr Val Arg Cys Ser Cys Glu Trp Glu Arg Leu Met Ser
                645                 650                 655

Ser Pro Ala Val His Arg Val Leu Ala Ala Gln Arg Asn Leu Gln
            660                 665                 670

Leu Pro Asp Ser Val Thr His Asp Asn Ile Glu Ile Arg Phe Ala Phe
        675                 680                 685

His Ser Arg Leu Pro Thr Asp Met Cys Asp Phe Val Val Leu Gln His
            690                 695                 700

Val Leu Ser Cys Ile Pro Asp Asp Val Leu Ala Ser Ala Tyr Ile Arg
705                 710                 715                 720

Arg Ser Ala Ala Leu Cys Ser Gly Cys Val Phe Val Glu Thr Asp
                725                 730                 735

Val Gln Cys Arg Gln Tyr Tyr Thr Leu Lys Cys Ser Val Arg Cys Asp
            740                 745                 750

Tyr Asp Ala Val Ala Pro Leu Phe Phe Gln Gln Leu His Arg Val Ser
        755                 760                 765

Tyr Gly Thr Lys Ala Ala Arg Val Arg Thr Lys Gly Glu Leu Glu Ser
        770                 775                 780

Leu Ile Pro Thr Val Cys Cys Ala Arg Tyr Lys Leu Gln Gly Ser Pro
785                 790                 795                 800

Leu Asn Thr Thr Val His Val Val Ala Pro Ala Pro Pro Arg
                805                 810

<210> SEQ ID NO 5
<211> LENGTH: 814
<212> TYPE: PRT
<213> ORGANISM: Leishmania infantum

<400> SEQUENCE: 5

Met Glu Pro Asp Pro Lys Lys Val Lys Leu Asp Ile Phe Asp Phe Pro
1               5                   10                  15

Thr Ala Arg Glu Thr Arg Thr Pro Glu Glu Val Ala Glu Ser Tyr Ala
            20                  25                  30

Glu Ala Val Lys Ser His Pro Phe Tyr Asp Asn Val His Ser Ala Ile
```

```
                35                  40                  45
Asp Phe Tyr Asp Ser Gly Thr Ile Lys Asp Gly Arg Gly Gln Ile Ile
 50                  55                  60

Gly Val Val Leu Arg Glu Ala Leu Pro Lys Tyr Ala Ala Ser Met Ala
 65                  70                  75                  80

Ser Glu Leu Leu Ala Ser Ala Ala Val Arg Thr Ser Leu Arg Ser Met
                 85                  90                  95

Met Phe Gly Gly Glu Ser Pro Leu Ser Gly Ile Ala Gly Tyr Phe Asp
                100                 105                 110

Tyr Arg Gly Ser Pro Val Glu Leu Lys Ser Arg Lys Thr Ser Phe Thr
            115                 120                 125

Tyr Glu His Glu Ala Ala Trp Pro Ala Val Phe Pro Val Val Asp Tyr
        130                 135                 140

Val Ser Glu Leu Tyr Arg His Val Ala Pro Glu Arg Trp Lys Ala Gln
145                 150                 155                 160

Asn Asp Ala Ile Pro Asp Val Val Arg Ile His Gly Thr Pro Phe Ser
                165                 170                 175

Thr Leu Thr Ile Asn Ser Arg Phe Arg Thr Ala Ser His Thr Asp Val
            180                 185                 190

Gly Asp Phe Asp Gly Gly Tyr Ser Cys Ile Ala Cys Leu Asp Gly Gln
        195                 200                 205

Phe Lys Gly Leu Ala Leu Ala Phe Asp Asp Phe Gly Ile Asn Val Leu
210                 215                 220

Met Gln Pro Arg Asp Val Met Ile Phe Asp Ser His His Phe His Ser
225                 230                 235                 240

Asn Thr Glu Val Glu Leu Ser Phe Ser Gly Glu Asp Trp Lys Arg Leu
                245                 250                 255

Thr Cys Val Phe Tyr Tyr Arg Ala Ala Leu Gly Glu Pro Ala Ser Tyr
            260                 265                 270

Ala Glu Tyr Arg Arg Arg Leu Glu Lys Ser Lys Gln Asp Thr Ser Phe
        275                 280                 285

Thr Pro Val Val Ser Asn Val Arg Val Lys Glu Asn Gly Thr Asn Leu
        290                 295                 300

Asn Arg Pro Ser Pro Val Tyr Pro Ile Phe Leu Ser Pro Phe Trp Val
305                 310                 315                 320

Pro Met Val Ala His Cys Leu Gln His Cys Ala Ser Glu Ala Gln Cys
                325                 330                 335

Val His Asp Ala Met Thr Ala Asp Gly Ser Arg Leu Ala Glu Val Met
            340                 345                 350

Phe Gly Glu Pro Leu Ser Thr Ser Asp Gly Ile Pro Leu Arg Gly Glu
        355                 360                 365

Glu Glu Lys Leu Lys Ala Asn Ser Asp Ser Ala Ser Arg Pro Leu Ser
    370                 375                 380

Arg Leu Gly Gly Phe Ser Glu Thr Asn Leu Met Val Ser Thr Ala Val
385                 390                 395                 400

Glu Lys Lys Lys Tyr Leu Asn Ser Glu Phe Leu Ser His Phe Ile Ser
                405                 410                 415

Ala Gln Leu Leu Asp Met Trp Lys Gln Ala Arg Gly Lys Trp Leu Glu
            420                 425                 430

Leu Val Gly Arg Glu Trp Thr His Met Leu Ala Leu Asn Pro Glu Arg
        435                 440                 445

Lys Asp Phe Leu Trp Arg Asn Gln Ser Glu Met Asn Ser Ala Phe Phe
    450                 455                 460
```

Asp Leu Cys Glu Val Gly Lys Gln Val Met Leu Gly Leu Leu Gly Lys
465                 470                 475                 480

Glu Ala Ala Leu Pro Lys Glu Glu Gln Ala Phe Trp Thr Met Tyr Ala
            485                 490                 495

Val His Leu Asn Ala Ala Cys Ala Glu Glu Leu Asn Met Pro His Val
        500                 505                 510

Ala Met Ser Leu Arg Lys Leu Asn Val Lys Leu Lys Asp Phe Asn Phe
    515                 520                 525

Gly Gly Thr Arg Tyr Phe Lys Asp Met Pro Pro Glu Glu Gln Lys Arg
530                 535                 540

Arg Met Glu Arg Lys Gln Arg Ile Glu Glu Ala Arg His Gly Met
545                 550                 555                 560

Ser Ser Gly Ala His Glu Lys Arg Ala Asn Trp Leu Thr Asn Asp Ser
            565                 570                 575

Phe Asp Tyr Gln Thr Glu Asp Cys Val Phe Asp Tyr Ala Gln His Lys
        580                 585                 590

Trp Val Pro Pro Ala Leu His Ala Lys Glu Ile Thr Lys Asn Val Arg
    595                 600                 605

Ser Gly Glu Leu Pro Thr Arg Glu Gly Val Val Arg Val Leu Val Val
610                 615                 620

Leu Pro Asp Pro Gln Ser Lys Val Asp Cys Val Asp Cys Lys Leu Glu
625                 630                 635                 640

Val Ser Glu Thr Val Arg Cys Ser Cys Glu Trp Arg Leu Met Ser
            645                 650                 655

Ser Pro Ala Val His Arg Val Leu Ala Ala Gln Arg Asn Leu Gln
        660                 665                 670

Leu Pro Asp Ser Val Thr His Asp Asn Ile Glu Ile Arg Phe Ala Phe
    675                 680                 685

His Ser Arg Leu Pro Thr Asp Met Cys Asp Phe Val Val Leu Gln His
        690                 695                 700

Val Leu Ser Cys Ile Pro Asp Asp Val Leu Ala Ser Ala Tyr Ile Arg
705                 710                 715                 720

Arg Ser Ala Ala Leu Cys Ser Gly Cys Val Phe Val Val Glu Thr Asp
            725                 730                 735

Val Gln Cys Arg Gln Tyr Tyr Thr Leu Lys Cys Ser Val Arg Cys Asp
        740                 745                 750

Tyr Asp Ala Val Ala Pro Leu Phe Phe Gln Gln Leu His Arg Val Ser
    755                 760                 765

Tyr Gly Thr Lys Ala Ala Arg Val Arg Thr Lys Gly Glu Leu Glu Ser
    770                 775                 780

Leu Ile Pro Thr Val Cys Cys Ala Arg Tyr Lys Leu Gln Gly Ser Pro
785                 790                 795                 800

Leu Asn Thr Thr Val His Val Val Ala Pro Ala Pro Pro Arg
            805                 810

<210> SEQ ID NO 6
<211> LENGTH: 814
<212> TYPE: PRT
<213> ORGANISM: Leishmania major
<220> FEATURE:
<223> OTHER INFORMATION: Leishmania major strain Friedlin

<400> SEQUENCE: 6

Met Glu Pro Asp Pro Lys Lys Ile Lys Leu Asp Ile Phe Asn Phe Pro
1               5                   10                  15

-continued

```
Thr Ala Arg Glu Thr Arg Thr Pro Glu Glu Val Ala Glu Ser Tyr Ala
             20                  25                  30

Glu Ala Val Lys Ser His Pro Phe Tyr Asp Asn Val His Ser Val Ile
         35                  40                  45

Asp Phe Tyr Asp Ser Gly Thr Ile Lys Asp Gly Arg Gly Gln Ile Ile
     50                  55                  60

Gly Val Val Leu Arg Glu Ala Leu Pro Lys Tyr Ala Val Ser Met Ala
 65                  70                  75                  80

Ser Glu Leu Leu Ala Ser Ala Ala Val Arg Thr Ser Leu Arg Ser Met
                 85                  90                  95

Met Phe Gly Gly Glu Ser Pro Leu Ser Gly Ile Ala Gly Tyr Phe Asp
             100                 105                 110

Tyr Arg Gly Ser Pro Val Glu Leu Lys Ser Arg Lys Thr Ser Phe Thr
         115                 120                 125

Tyr Glu His Glu Ala Ala Trp Pro Ala Val Phe Pro Val Val Asp Tyr
     130                 135                 140

Val Ser Glu Leu Tyr Arg His Val Ala Pro Glu Arg Trp Lys Ala Gln
145                 150                 155                 160

Asn Asp Ala Ile Pro Asp Val Val Arg Ile His Gly Thr Pro Phe Ser
                 165                 170                 175

Thr Leu Thr Ile Asn Ser Arg Phe Arg Thr Ala Ser His Thr Asp Val
             180                 185                 190

Gly Asp Phe Asp Gly Gly Tyr Ser Cys Ile Ala Cys Leu Asp Gly His
         195                 200                 205

Phe Lys Gly Leu Ala Leu Ala Phe Asp Asp Phe Gly Ile Asn Val Leu
     210                 215                 220

Met Gln Pro Arg Asp Val Met Ile Phe Asp Ser His His Phe His Ser
225                 230                 235                 240

Asn Thr Glu Val Glu Leu Ser Phe Ser Gly Glu Asp Trp Lys Arg Leu
                 245                 250                 255

Thr Cys Val Phe Tyr Tyr Arg Ala Ala Leu Gly Glu Pro Ala Ser Tyr
             260                 265                 270

Ala Glu Tyr Gln Arg Arg Leu Glu Lys Ser Lys Gln Asp Asn Ser Phe
         275                 280                 285

Thr Pro Val Val Ser Asn Val Arg Val Lys Glu Asn Gly Thr Asn Leu
     290                 295                 300

Asn Arg Pro Ser Pro Val Tyr Pro Ile Cys Pro Ser Pro Phe Trp Val
305                 310                 315                 320

Pro Met Val Ala His Cys Leu Gln His Cys Ala Ser Glu Ala Gln Cys
                 325                 330                 335

Val His Asp Ala Met Thr Ala Asp Gly Ser Arg Leu Ala Glu Val Met
             340                 345                 350

Phe Gly Glu Pro Leu Ser Thr Ser Asp Gly Ile Pro Leu Arg Gly Glu
         355                 360                 365

Asp Lys Lys Leu Lys Ala Asn Ser Asp Ser Ala Ser Arg Pro Leu Ser
     370                 375                 380

Arg Leu Gly Gly Phe Ser Glu Thr Asn Leu Met Val Ser Thr Ala Val
385                 390                 395                 400

Glu Lys Lys Lys Tyr Leu Asn Ser Glu Phe Leu Ser His Phe Ile Ser
                 405                 410                 415

Ala Gln Leu Leu Asp Met Trp Lys Gln Ala Arg Gly Lys Trp Leu Glu
             420                 425                 430
```

```
Leu Val Gly Arg Glu Trp Thr His Met Leu Ala Leu Asn Pro Glu Arg
            435                 440                 445

Lys Asp Phe Leu Trp Lys Asn Gln Ser Glu Met Asn Ser Ala Phe Phe
450                 455                 460

Asp Leu Cys Glu Val Gly Lys Gln Val Met Leu Gly Leu Leu Gly Lys
465                 470                 475                 480

Glu Val Ala Leu Pro Lys Glu Gln Ala Phe Trp Thr Met Tyr Ala
                485                 490                 495

Val His Leu Asn Ala Ala Cys Ala Glu Leu His Met Pro His Val
            500                 505                 510

Ala Met Ser Leu Arg Lys Leu Asn Val Lys Leu Lys Asp Phe Asn Phe
            515                 520                 525

Gly Gly Thr Arg Tyr Phe Lys Asp Met Pro Pro Glu Glu Gln Lys Arg
            530                 535                 540

Arg Met Glu Arg Lys Gln Arg Ile Glu Glu Ala Arg Arg His Gly Met
545                 550                 555                 560

Ser Ser Gly Ala His Glu Lys Arg Ala Asn Trp Leu Thr Asn Asp Ser
                565                 570                 575

Phe Asp Tyr Gln Thr Glu Asp Cys Val Val Asp Tyr Ala Gln His Lys
            580                 585                 590

Trp Pro Pro Pro Ala Leu His Ala Lys Glu Ile Thr Lys Asn Val Arg
            595                 600                 605

Thr Gly Glu Leu Pro Thr Arg Glu Gly Val Val Arg Val Leu Val Val
            610                 615                 620

Leu Pro Asp Pro Gln Ser Lys Leu Glu Cys Val Asp Cys Lys Leu Glu
625                 630                 635                 640

Val Pro Glu Thr Val Arg Cys Ser Cys Glu Trp Glu Arg Leu Met Ser
                645                 650                 655

Ser Leu Ala Val Arg Arg Val Leu Ala Ala Gln Arg Asn Leu Gln
            660                 665                 670

Leu Pro Gly Ser Val Thr His Gly Asn Ile Glu Ile Arg Phe Ala Phe
            675                 680                 685

His Ser Arg Leu Pro Thr Asp Met Cys Asp Phe Val Val Leu Gln His
            690                 695                 700

Val Leu Ser Cys Ile Pro Asp Asp Val Leu Ala Ser Ala Tyr Ile Arg
705                 710                 715                 720

Arg Ala Ala Ala Leu Cys Thr Gly Cys Val Tyr Val Glu Thr Asp
                725                 730                 735

Val Gln Cys Arg Gln Tyr Tyr Thr Leu Lys Cys Ala Ala Arg Cys Asp
                740                 745                 750

Tyr Asp Ala Val Ala Ser Leu Phe Phe Gln Gln Leu His Arg Val Ser
            755                 760                 765

Tyr Gly Thr Lys Ala Ala Arg Val Arg Thr Lys Gly Glu Leu Glu Ser
770                 775                 780

Leu Ile Pro Thr Val Cys Cys Ala Arg Tyr Lys Leu Gln Gly Ser Pro
785                 790                 795                 800

Leu Asn Thr Thr Val His Val Val Ser Pro Ala Pro Ser Arg
                805                 810
```

<210> SEQ ID NO 7
<211> LENGTH: 814
<212> TYPE: PRT
<213> ORGANISM: Leishmania mexicana

<400> SEQUENCE: 7

-continued

```
Met Glu Pro Asp Ser Lys Lys Val Lys Leu Asp Ile Phe Ser Phe Pro
1               5                   10                  15

Thr Ala Arg Glu Thr Arg Thr Pro Glu Val Ala Glu Ser Tyr Ala
            20                  25                  30

Glu Ala Val Lys Ser His Pro Phe Tyr Asp Asn Val His Ser Val Ile
            35                  40                  45

Asp Phe Tyr Asp Ser Gly Thr Ile Lys Asp Gly Arg Gly Lys Ile Ile
        50                  55                  60

Gly Val Val Leu Arg Glu Ala Leu Pro Lys Tyr Ala Thr Ser Met Ala
65                  70                  75                  80

Ser Glu Leu Leu Thr Ser Ala Ala Val Arg Thr Ser Leu Arg Ser Met
                85                  90                  95

Met Phe Gly Gly Glu Ser Pro Leu Ser Gly Ile Ala Gly Tyr Phe Asp
                100                 105                 110

Tyr Arg Gly Ser Pro Val Glu Leu Lys Ser Arg Lys Thr Ser Phe Thr
            115                 120                 125

Tyr Glu His Glu Ala Glu Trp Pro Ala Val Phe Pro Val Ile Asp Tyr
            130                 135                 140

Val Ser Glu Leu Tyr Arg His Val Ala Pro Lys Gln Trp Lys Ala Gln
145                 150                 155                 160

Asn Asp Ala Ile Pro Asp Leu Val Arg Ile His Gly Thr Pro Phe Ser
                165                 170                 175

Thr Leu Thr Ile Asn Ser Arg Phe Arg Thr Ala Ser His Thr Asp Val
                180                 185                 190

Gly Asp Phe Asp Gly Gly Tyr Ser Cys Ile Ala Cys Leu Asp Gly Gln
            195                 200                 205

Phe Lys Gly Leu Ala Leu Ala Leu Asp Ser Phe Gly Ile Asn Val Leu
            210                 215                 220

Met Gln Pro Arg Asp Val Met Ile Phe Asp Ser His His Phe His Ser
225                 230                 235                 240

Asn Thr Glu Val Glu Leu Ser Phe Ser Gly Glu Asp Trp Lys Arg Leu
                245                 250                 255

Thr Cys Val Phe Tyr Tyr Arg Ala Ala Leu Gly Glu Pro Ala Ser Tyr
                260                 265                 270

Ala Glu Tyr Arg Arg Arg Leu Glu Lys Ser Lys Gln Asp Thr Ser Phe
            275                 280                 285

Thr Pro Ala Val Ser Asn Val Arg Val Lys Glu Asn Asp Thr Asn Leu
            290                 295                 300

Asn Arg Pro Ser Pro Val Tyr Pro Ile Ser His Ser Pro Phe Trp Val
305                 310                 315                 320

Pro Met Val Ala His Cys Leu Gln His Cys Ala Ser Ala Ala Gln Cys
                325                 330                 335

Val His Asp Ala Met Thr Ala Asp Gly Ser Arg Leu Ala Glu Val Met
                340                 345                 350

Phe Gly Glu Pro Leu Ser Thr Leu Asp Gly Ile Pro Leu Arg Arg Glu
            355                 360                 365

Asp Glu Lys Leu Lys Ala Asn Gly Asp Ser Ala Ser Arg Pro Leu Ser
            370                 375                 380

Arg Leu Gly Gly Phe Ser Glu Thr Asn Leu Met Val Thr Thr Ala Val
385                 390                 395                 400

Glu Lys Lys Lys Tyr Leu Asn Ser Glu Phe Leu Ser His Gly Ile Ser
                405                 410                 415
```

Ala Gln Leu Leu Asn Met Trp Lys Gln Ala Arg Ala Lys Trp Leu Glu
            420                 425                 430

Leu Val Ser Arg Glu Trp Thr His Met Ile Ala Leu Asn Pro Glu Arg
        435                 440                 445

Lys Asp Phe Leu Trp Lys Asn Gln Ser Glu Met Asn Ser Ala Phe Phe
450                 455                 460

Asp Leu Cys Glu Val Gly Lys Gln Val Met Leu Gly Leu Leu Gly Lys
465                 470                 475                 480

Glu Ala Ala Leu Pro Lys Glu Glu Gln Ala Phe Trp Thr Met Tyr Ala
                485                 490                 495

Val His Leu Asn Ala Ala Cys Ala Glu Glu Leu His Met Pro His Ala
            500                 505                 510

Ala Met Ser Leu His Lys Leu Asn Val Lys Leu Lys Asp Phe Asn Phe
        515                 520                 525

Gly Gly Thr Arg Tyr Phe Lys Asp Met Pro Pro Glu Glu Gln Lys Arg
    530                 535                 540

Arg Val Glu Arg Lys Gln Arg Ile Glu Glu Ala Arg His Gly Met
545                 550                 555                 560

Ser Ser Gly Ser His Glu Lys Arg Ala Asn Trp Leu Thr Asn Asp Ser
                565                 570                 575

Phe Asp Tyr Gln Thr Glu Asp Cys Ile Val Asp Tyr Ala Gln His Lys
            580                 585                 590

Trp Val Pro Pro Ala Val His Ala Lys Glu Ile Thr Lys Asn Val Arg
        595                 600                 605

Thr Gly Glu Leu Pro Thr Arg Glu Gly Leu Val Arg Val Leu Val Val
    610                 615                 620

Leu Pro Asp Pro Gln Ser Lys Val Lys Cys Val Asp Cys Lys Leu Glu
625                 630                 635                 640

Val Pro Glu Thr Leu Arg Cys Ser Ser Glu Trp Glu Arg Leu Met Ser
                645                 650                 655

Ser Leu Ala Val His Arg Val Leu Ala Ala Val Gln Arg Asn Leu Gln
            660                 665                 670

Leu Pro Asp Ser Val Thr Gln Gly Asn Ile Gln Ile His Phe Ala Phe
        675                 680                 685

His Ser Thr Leu Pro Thr Ala Val Tyr Asp Phe Val Val Leu Gln His
    690                 695                 700

Val Leu Ser Cys Ile Pro Glu Asp Val Leu Ala Ser Glu Tyr Ile Arg
705                 710                 715                 720

Arg Ala Ala Ala Leu Cys Ser Gly Cys Leu Phe Val Ala Glu Thr Asp
                725                 730                 735

Val Gln Cys Arg Gln Tyr Tyr Thr Leu Lys Cys Ala Val Arg Cys Asp
            740                 745                 750

Tyr Asp Thr Val Ala Pro Leu Phe Phe Gln Leu His Gln Ala Ser
        755                 760                 765

Tyr Gly Thr Lys Ala Ala Arg Val Arg Thr Lys Gly Glu Leu Glu Ser
    770                 775                 780

Leu Ile Pro Thr Val Cys Cys Ala Arg Tyr Lys Leu Lys Gly Ser Pro
785                 790                 795                 800

Leu Asn Thr Thr Val His Val Val Ser Pro Ala Pro Pro Ser
                805                 810

<210> SEQ ID NO 8
<211> LENGTH: 811
<212> TYPE: PRT

<213> ORGANISM: Crithidia fasciculata

<400> SEQUENCE: 8

```
Met Glu Pro Lys Ser Lys Lys Val Lys Gln Asp Ile Phe Asn Phe Pro
1               5                   10                  15

Asp Gly Lys Asp Val Pro Thr Thr Lys Glu Lys Ala Glu Ala Tyr Val
            20                  25                  30

Asp Ala Leu Lys Ala His Pro Phe Tyr Asp Asn Val His Ser Val Val
        35                  40                  45

Asp Val Tyr Asp Ser Ala Thr Leu Arg Asp Gly Lys Gly Arg Val Ile
    50                  55                  60

Gly Val Met Leu Arg Lys Ala Leu Pro Glu His Ala Thr Ala Ala
65                  70                  75                  80

Ser Gly Leu Leu Ser Ala Ala Val Arg Thr Ser Leu Arg Ser Ser
                85                  90                  95

Met Phe Gly Gly Glu Ser Pro Leu Ser Gly Ile Ala Gly Tyr Phe Asp
            100                 105                 110

Tyr Arg Gly Ser Pro Val Glu Leu Lys Ala Arg Lys Thr Ala Phe Thr
        115                 120                 125

Tyr Glu His Glu Lys Lys Trp Pro Ala Val Phe Pro Leu Val Asp Tyr
    130                 135                 140

Val Ser Glu Ile Tyr Lys Ser Val Met Pro Glu His Trp Ala Ala Gln
145                 150                 155                 160

Asp Ser Ala Ile Pro Asp Ile Val Arg Ile His Gly Thr Pro Phe Ser
                165                 170                 175

Thr Leu Thr Ile Asn Ser Arg Phe Arg Thr Ala Ser His Thr Asp Ala
            180                 185                 190

Gly Asp Phe Asp Gly Gly Tyr Ser Cys Ile Ala Cys Ile Asp Gly Asp
        195                 200                 205

Phe Lys Gly Leu Ala Leu Gly Phe Asp Phe His Val Asn Val Pro
    210                 215                 220

Met Gln Pro Arg Asp Val Leu Val Phe Asp Ser His Tyr Phe His Ser
225                 230                 235                 240

Asn Ser Glu Leu Glu Ile Ser Cys Pro Thr Glu Glu Trp Arg Arg Leu
                245                 250                 255

Thr Cys Val Phe Tyr Tyr Arg Ser Ala Leu Gly Glu Pro Ser Ser Tyr
            260                 265                 270

Ala Glu Tyr Arg Arg Arg Leu Ala Ala Gln Gln Asp Ser Thr Ala
        275                 280                 285

Gln Pro Val Ser Ser Val Val Glu Lys Pro Asn Gly Lys Asn Leu
    290                 295                 300

Tyr Lys Pro Ser Thr Val Phe Pro Ile Asp Pro Thr Pro Phe Ala Val
305                 310                 315                 320

Val Ala Gln Leu His Arg Leu His His Cys Ala Ala Lys Gly Leu Cys
                325                 330                 335

Val His Glu Leu Leu Ala Val Pro Ser Ser Pro Leu Ala Val Leu Leu
            340                 345                 350

Phe Gly Glu Arg Leu Ser Cys Ser Asp Gly Ile Pro Leu Arg Ala Ala
        355                 360                 365

Glu Gln Lys Leu Lys Ala Asn Ala Asp Gly Ala Ser Arg Gly Val Thr
    370                 375                 380

Ser Ser Gly Gly Phe Ser Glu Ser Asp Ala Val Leu Thr Thr Ala Val
385                 390                 395                 400
```

```
Glu Lys Ser Lys Tyr Leu Glu Arg Asp His Leu Ser Gln Cys Ile Ser
                405                 410                 415

Ala Glu Leu Leu Ala Met Trp Val Glu Ala Arg Lys His Trp Leu Arg
            420                 425                 430

Leu Val Ala Thr Glu Trp Ala Arg Met Ile Ala Thr Ala Pro Glu Arg
        435                 440                 445

Thr Asp Phe Leu Trp Lys Asn Lys Ser Pro Met Asn Thr Ala Phe Phe
    450                 455                 460

Asp Leu Cys Glu Val Ala Lys Gln Val Met Leu Gly Leu Leu Asp Lys
465                 470                 475                 480

Glu Thr Ala Thr Pro Thr Glu Arg His Phe Trp Ser Val Tyr Ala
                485                 490                 495

Ala His Leu His Arg Ala Cys Ala Glu Arg Leu Met Met Pro Glu Glu
            500                 505                 510

Ala Met Ser Leu Arg Lys Leu Asn Val Lys Leu Lys Asp Phe Ser Phe
        515                 520                 525

Gly Gly Thr Arg Tyr Phe Lys Asp Met Pro Val Glu Glu Gln Glu Arg
    530                 535                 540

Arg Val Ala Arg Lys Ala Ser Ile Glu Glu Ala Arg Arg Ser Thr
545                 550                 555                 560

Ala Ala Lys Asp Gly Glu Gln Arg Ser Asn Trp Leu Thr Asn Asp Ala
                565                 570                 575

Phe Asp Tyr Gln Thr Glu Asp Cys Glu Val Asp Tyr Ala Gly His Gly
            580                 585                 590

Trp Ala Val Pro Lys Gln His Ala Lys Thr Val Thr Ala Asn Val His
        595                 600                 605

Gln Glu Ala Val Ala Ala Thr Thr Glu Ala Val Arg Val Leu Val Val
    610                 615                 620

Leu Pro Arg Pro Pro Ser Gly Asp Arg Gly Asp Ala Ala Val Asp Leu
625                 630                 635                 640

Pro Lys Glu Val Thr Thr Ser Ala Glu Trp Val Arg Leu Met Ser Ser
                645                 650                 655

Pro Ala Val Arg Arg Val Leu Ala Ala Lys Gln Arg Asn Leu Thr Leu
            660                 665                 670

Leu Pro Asn Cys Asn Val Glu Ala Val Ser Leu Asn Phe Ala Tyr His
        675                 680                 685

Asp Ser Leu Pro Gln Lys Ala Thr Phe Asp Phe Val Val Leu Gln His
    690                 695                 700

Val Leu Ser Ala Met Pro Glu Asp Ala Ile Ala Thr Asp Tyr Val Ser
705                 710                 715                 720

Arg Met Arg Ser Ile Cys Thr Gly Cys Leu Phe Val Val Glu Thr Asp
                725                 730                 735

Val Gln Cys Arg Gln Tyr Phe Thr Leu His Tyr Pro Leu Arg Val Gln
            740                 745                 750

Tyr Asp Ala Val Ala Pro Ala Phe Phe Gln Leu Leu His Arg Cys Ser
        755                 760                 765

Tyr Gly Thr Pro Leu Ala Arg Thr Arg Thr Lys Ala Glu Val Glu Ala
    770                 775                 780

Leu Phe Pro Phe Val Cys Cys Ala Arg Tyr Lys Leu Gln Gly Ser Pro
785                 790                 795                 800

Met Asn Thr Val Val His Leu Leu Ala Leu Glu
                805                 810
```

<210> SEQ ID NO 9
<211> LENGTH: 839
<212> TYPE: PRT
<213> ORGANISM: Trypanosoma brucei

<400> SEQUENCE: 9

Met Arg Arg Gln Val Lys Lys Val Leu Arg Glu Lys Ala Asp Asp Ser
1               5                   10                  15

Met Lys Pro Gly Trp Asp Val Tyr Gln Pro Ser Asn Asp Val Val Tyr
            20                  25                  30

Ala Phe Asn His Tyr Met Gln Gly Ser Gln Ile Asp Ala Glu Ala Arg
        35                  40                  45

Glu Lys Ala Glu Lys Ala Phe Gln Glu Ala Val Lys Lys His Pro Phe
    50                  55                  60

His Asn Asn Ala Asp His Thr Val Asp Phe His Gly Thr Thr Val Phe
65                  70                  75                  80

Arg Asn Ala Lys Gly Lys Val Cys Gly Val Leu Ile Pro Lys Ala Leu
                85                  90                  95

Pro Ser Phe Ala Thr Ser Met Ala Ala Asp Val Leu Glu Cys Ala Val
            100                 105                 110

Ala Arg Thr Ser Leu Arg Ser Ala Leu Phe Gly Gly Val Ser Pro Asn
        115                 120                 125

Ser Gly Ile Ala Gly Tyr Phe Asp Tyr Arg Gly Thr Pro Val Glu Leu
130                 135                 140

Lys Cys Arg Lys Thr Ser Phe Thr Tyr Glu His Thr Lys Glu Trp Arg
145                 150                 155                 160

Ser Val Phe Pro Met Ile Asp Tyr Thr Ser Ala Ile Tyr Lys Ala Ala
                165                 170                 175

Leu Pro Asp His Trp Lys Ala Gln Asp Ala Ala Val Pro Asp Val Val
            180                 185                 190

Arg Ile His Gly Ser Pro Phe Ser Thr Leu Thr Val Asn Glu Arg Phe
        195                 200                 205

Arg Thr Ala Ser His Thr Asp Asn Gly Asp Phe Asp Asn Gly Tyr Gly
    210                 215                 220

Val Leu Ala Val Leu Lys Gly Glu Tyr Ser Gly Leu Ser Leu Ala Leu
225                 230                 235                 240

Asp Asp Tyr Gly Val Cys Phe Asn Met Gln Pro Thr Asp Val Leu Leu
                245                 250                 255

Phe Asp Thr His Leu Phe His Ser Asn Thr Glu Leu Glu Ala Lys Glu
            260                 265                 270

Ala Asn Ala Thr Trp Asn Arg Leu Ser Cys Val Phe Tyr Tyr Arg Ala
        275                 280                 285

Ala Leu Gly Glu Gln Pro Cys Val Glu Tyr Arg Arg Arg Leu Lys
    290                 295                 300

Lys Ala Lys Glu Glu Lys Ser Thr Ser Leu Ser Phe Asn His Ile Glu
305                 310                 315                 320

Gln Lys Asp Asn Gly Glu Asn Thr Asn Lys Pro Ala Pro Val Tyr Pro
                325                 330                 335

Val Ser Leu Thr Pro Phe Ser Cys Ala Ala Ser Ala Trp Ala Leu Arg
            340                 345                 350

Gly Cys Ala Ala Ala Met Leu Thr Arg Leu His Gly Leu Val Arg Glu
        355                 360                 365

Asn Ala Ser Leu Met Thr Glu Leu Phe Gly Glu Pro Val Glu Val Ala
    370                 375                 380

-continued

```
Asp Gly Leu Pro Arg Arg Ala Pro Glu Glu Ile Pro Val His Lys
385                 390                 395                 400

His Thr Asn Val Gln Met His Tyr Leu Gly Gly Phe Ser Glu Lys Gly
            405                 410                 415

Asp Ile Leu Asn Glu Ala Met Asn Lys Arg His Tyr Leu Asp Lys Glu
        420                 425                 430

Asn Leu Gln Lys Met Phe Gly Glu Glu Phe Val Asn Ile Trp Thr Gln
    435                 440                 445

Ser Arg Thr His Trp Leu Gln Leu Val Lys Lys Glu Trp Glu His Gln
450                 455                 460

Lys Glu Thr Asn Pro Thr Arg Thr Arg Phe Ser Trp Asn Asn Thr Ser
465                 470                 475                 480

Ala Met Asn Phe Ala Phe Phe Asp Leu Cys Asp Val Ala Lys Gln Leu
            485                 490                 495

Met Cys Gly Ala Phe Gly Asp Arg Glu Val Asn Lys Lys Glu Glu Gln
        500                 505                 510

Ser Phe Trp Gly Met Phe Ala Ala His Leu Asp Asn Ala Cys Ile Asn
    515                 520                 525

Glu Ile Gly Met Leu Gln Gly Ser Met Gly Met His Lys Leu Asn Val
530                 535                 540

Lys Leu Lys Asp Tyr Asn Phe Gly Gly Thr Arg Tyr Leu Lys Asp Met
545                 550                 555                 560

Pro Pro Glu Glu Gln Glu Arg Arg Arg Arg Leu Glu Ile Glu
            565                 570                 575

Gln Ala Arg Arg Arg Ala Pro Ile Cys Asp Ser Glu Ser Gly Asp Trp
        580                 585                 590

Leu Arg Asn Glu Ala Phe Asp Tyr Gln Thr Glu Asp Val Ala Val Asn
    595                 600                 605

Tyr Glu Arg Glu Gln Trp Ile Thr Pro Glu Asn Asn Ala Lys Arg Phe
610                 615                 620

Gly Phe Pro Glu Arg Gly Val Tyr Gly Ala Glu Gly Ala Ala Thr Gly
625                 630                 635                 640

Thr Ile Ser Val Leu Ile Val Leu Pro Lys Pro Thr Asn His Arg Gln
            645                 650                 655

Lys Thr Cys Glu Leu Pro Thr Ser Arg Glu Ala Asp Arg Ile Met Lys
        660                 665                 670

Asn Pro Ala Ala Gln Arg Leu Leu Cys Ala Lys Pro Cys Asn Ile Gly
    675                 680                 685

Leu Ser Thr Ser Ser Asn Lys Ser Arg Thr Val Leu Cys Gly Asn Ile
690                 695                 700

Arg Ile Asp Lys Val Phe Asp Gly Gly Ser Val Gly Gly Lys Met Tyr
705                 710                 715                 720

Asp Phe Val Ile Met Arg His Leu Leu Ala Ala Thr Gly Glu Arg
            725                 730                 735

Glu Pro Leu Glu Cys Leu Val Arg Trp Thr Ser Leu Ala Arg Tyr Cys
        740                 745                 750

Thr Phe Val Val Glu Val Asp Leu Leu Asp Arg His His Tyr Ile Leu
    755                 760                 765

Lys Ser Glu Ile Gly Glu Glu Tyr Ser Ala Val Ser Glu Ile Cys Phe
770                 775                 780

Ser Ala Leu Tyr Ser Ala Thr Tyr Ala Arg Asp Lys Val Asn Leu Arg
785                 790                 795                 800

Thr Thr Pro Cys Leu Leu Ser Phe Ile Asp Lys Ser Gly Asn Met Leu
```

```
                                805                 810                 815
Glu Ser Arg Phe Lys Phe Asn Gly Ser Pro Leu Asn Thr Val Ala Phe
                820                 825                 830

Val Val Arg Arg Glu Lys
        835

<210> SEQ ID NO 10
<211> LENGTH: 831
<212> TYPE: PRT
<213> ORGANISM: Trypanosoma cruzi

<400> SEQUENCE: 10

Met Lys Gln Lys Arg Gly Lys Gln Asp Val Lys Met Val Glu Ser Ala
1               5                   10                  15

Pro Pro Gln Leu Leu Pro Lys Lys Gly Arg Leu Glu Ile Ser Glu Leu
            20                  25                  30

Ala Pro Gln Gln Arg Thr Ile Arg Thr Ala Glu Glu Ile Glu Met Ala
        35                  40                  45

Tyr Asn Glu Ala Val Arg Lys His Pro Phe Tyr Asp Asn Ala Asp His
    50                  55                  60

Thr Ile Asp Phe His Asp Ala Thr Val Phe Arg Asp Ala Arg Gly Val
65                  70                  75                  80

Val Gly Gly Val Leu Leu Pro Gly Ala Leu Pro Ala Phe Ala Ala Thr
                85                  90                  95

Met Ala Ala Asp Val Leu Arg Pro Ala Ala Val Arg Thr Ser Leu Arg
            100                 105                 110

Ser Asn Met Phe Gly Gly Phe Ala Pro Leu Ser Gly Ile Ala Gly Tyr
        115                 120                 125

Phe Asp Tyr Arg Gly Ser Pro Val Glu Leu Lys Cys Arg Lys Thr Ser
    130                 135                 140

Phe Thr Tyr Glu Asn Val His Ser Trp Pro Asn Val Phe Pro Met Ile
145                 150                 155                 160

Asp Tyr Val Ser Ala Ile Tyr Lys Ala Val Phe Pro Glu Arg Trp Ala
                165                 170                 175

Ala Gln Asp Ala Ala Val Pro Asp Ile Val Arg Ile His Gly Ser Pro
            180                 185                 190

Phe Ser Thr Leu Thr Val Asn Gln Gln Phe Arg Thr Ala Ser His Thr
        195                 200                 205

Asp Ala Gly Asp Phe Asp Met Gly Tyr Gly Leu Leu Ala Val Leu Glu
    210                 215                 220

Gly Lys Phe Glu Gly Leu Ser Leu Ala Leu Asp Phe Gly Val Cys
225                 230                 235                 240

Phe Arg Met Gln Pro Arg Asp Val Leu Ile Phe Asn Thr His Phe Phe
                245                 250                 255

His Ser Asn Thr Glu Pro Glu Leu Asn His Pro Lys Asp Asp Trp Ser
            260                 265                 270

Arg Leu Thr Cys Val Cys Tyr Tyr Arg Ala Ala Leu Gly Glu Pro Ala
        275                 280                 285

Cys Val Ala Glu Tyr Glu Arg Arg Leu Ala Arg Ala Lys Glu Ile Gly
    290                 295                 300

Ala Ser Pro Pro Pro Ala Val Asp Ala Ile Leu Gln Lys Asp Asn Gly
305                 310                 315                 320

Asn Asn Phe Asn Lys Pro Ala Pro Thr Phe Thr Tyr Ser Leu Thr Pro
                325                 330                 335
```

```
Phe Gly Gly Ala Ala Ser Ile Cys Ser Leu His Cys Cys Thr Ala Lys
                340                 345                 350
Leu Leu Arg Leu His Glu Leu Leu Glu Asn Pro Thr Leu Glu Val
            355                 360                 365
Ile Leu Phe Gly Glu Ser Leu Arg Thr Asp Asp Gly Leu Pro Arg Arg
370                 375                 380
Glu Lys Glu Gln Leu Ile Ser Val His Leu Pro Val Val Lys Met
385                 390                 395                 400
Ser Pro Ser Gly Gly Phe Ser Glu Leu Gly Gly Ala Leu Lys Ala Ala
                405                 410                 415
Glu Glu Lys Gln Tyr Phe Phe Glu Glu Lys Tyr Leu Ala Asp Glu Leu
                420                 425                 430
Gly Pro Asp Leu Met Ser Met Trp Thr Gln Ser Arg Ala His Trp Leu
            435                 440                 445
Arg Leu Val Lys Glu Asp Trp Glu Arg Leu Cys Arg Arg Asp Pro Glu
            450                 455                 460
Arg Thr Lys Phe Thr Trp Asn Asn Ser Ser Ala Met Asn Ala Ala Phe
465                 470                 475                 480
Phe Asp Leu Cys Glu Val Ala Lys Gln Met Met Ile Gly Leu Leu Asn
                485                 490                 495
Lys Glu Thr Pro Ser Ser Ala Glu Asn His Ser Phe Trp Ile Leu Phe
            500                 505                 510
Ala Ala His Leu Asn Tyr Ala Cys Thr Thr Glu Asn Gly Met Pro Arg
            515                 520                 525
Asp Ala Val Gly Met His Lys Leu Asn Val Lys Leu Lys Asp Phe His
530                 535                 540
Phe Gly Gly Thr Arg Tyr Leu Lys Asp Met Pro Pro Glu Glu Gln Glu
545                 550                 555                 560
Arg Arg Leu Glu Arg Lys Lys Arg Ile Glu Glu Ala Arg Arg Gly
                565                 570                 575
Asn Ala Ala Arg Glu Thr His Thr Asp Asn Trp Leu Leu Asn Asp Thr
                580                 585                 590
Phe Asp Tyr Gln Gln Glu Asp Arg Lys Val Glu Phe Glu Glu Asn Gly
                595                 600                 605
Trp Met Thr Pro Glu Ala Tyr Val Lys His Leu Gly Leu Lys Pro Cys
            610                 615                 620
Gly Asp Val Thr Ala Ala Ser Pro Thr Glu Pro Ile His Val Leu
625                 630                 635                 640
Val Val Leu Pro Arg Pro Ala Ala Ala Pro Lys Asp Val Lys Arg
                645                 650                 655
Asp Val Pro Leu Ala Thr Ser Glu Glu Ser Ile Arg Leu Leu Met Asn
                660                 665                 670
Pro Ala Ala Gln Arg Val Leu Thr Gly Lys Ala Arg Asn Val Thr Leu
            675                 680                 685
Pro Ser Pro Leu Ser Phe Gly Gly Val Lys Ile Thr Val Leu Phe Asp
            690                 695                 700
Gly Asp Asp Ile Asp Cys Ile His Pro Asp Phe Val Val Leu Gln His
705                 710                 715                 720
Leu Leu Ala Ala Ile Glu Glu Asp Glu Ala Ala Lys Ala Arg Val Lys
                725                 730                 735
Tyr Trp Ala His Val Ala Arg Tyr Cys Val Phe Val Glu Thr Asp
            740                 745                 750
Val Arg Asp Arg Arg His Phe Leu Leu Arg Glu Glu Val Arg Val Ala
```

-continued

```
                755                 760                 765

Tyr Glu Asp Val Ala Glu Asp Cys Phe Arg Ser Leu His Ala Ala Ala
            770                 775                 780

Tyr Ser Thr Lys Cys Asn Arg Leu Arg Thr Thr Pro Ser Leu Ile Ala
785                 790                 795                 800

Leu Ser Asn Ser Lys Asn Ile Gly Leu Arg Phe Lys Phe Arg Gly Ser
            805                 810                 815

Pro Leu Asn Thr Ile Ala Leu Ile Val Val Gly Glu Arg Leu Asp
            820                 825                 830

<210> SEQ ID NO 11
<211> LENGTH: 832
<212> TYPE: PRT
<213> ORGANISM: Trypanosoma cruzi

<400> SEQUENCE: 11

Met Lys Gln Lys Arg Gly Lys Gln Asp Val Lys Met Leu Glu Ser Ala
1               5                   10                  15

Pro Pro Gln Leu Leu Pro Lys Lys Gly Arg Leu Glu Ile Ser Glu Leu
            20                  25                  30

Ala Pro Gln Gln Arg Thr Ile Arg Thr Ala Glu Glu Ile Glu Thr Ala
        35                  40                  45

Tyr Asn Glu Ala Val Arg Lys His Pro Phe Tyr Asp Asn Ala Asp His
    50                  55                  60

Thr Ile Asp Phe His Asp Ala Thr Val Phe Arg Asp Ala Arg Gly Val
65                  70                  75                  80

Val Gly Gly Val Phe Leu Pro Gly Ala Leu Pro Ala Phe Ala Ala Thr
                85                  90                  95

Met Ala Ala Asp Val Leu Arg Pro Ala Ala Val Arg Thr Ser Leu Arg
            100                 105                 110

Ser Asn Met Phe Gly Gly Phe Ala Pro Leu Ser Gly Ile Ala Gly Tyr
        115                 120                 125

Phe Asp Tyr Arg Gly Ser Pro Val Glu Leu Lys Cys Arg Lys Thr Ser
    130                 135                 140

Phe Thr Tyr Glu Asn Val His Ser Trp Pro Asn Val Phe Pro Met Ile
145                 150                 155                 160

Asp Tyr Val Ser Ala Ile Tyr Lys Ala Val Phe Pro Glu Gln Trp Ala
                165                 170                 175

Ala Gln Asp Ala Ala Val Pro Asp Ile Val Arg Ile His Gly Ser Pro
            180                 185                 190

Phe Ser Thr Leu Thr Val Asn Gln Gln Phe Arg Thr Ala Ser His Thr
        195                 200                 205

Asp Ala Gly Asp Phe Asp Met Gly Tyr Gly Leu Leu Ala Val Leu Glu
    210                 215                 220

Gly Lys Phe Glu Gly Leu Ser Leu Ala Leu Asp Asp Phe Gly Val Cys
225                 230                 235                 240

Phe Arg Met Gln Pro Arg Asp Ile Leu Ile Phe Asn Thr His Phe Phe
                245                 250                 255

His Ser Asn Thr Glu Pro Glu Leu Asn His Pro Arg Asp Asp Trp Ser
            260                 265                 270

Arg Leu Thr Cys Val Cys Tyr Tyr Arg Ala Ala Leu Gly Glu Pro Ala
        275                 280                 285

Cys Val Ala Glu Tyr Glu Arg Arg Leu Ala Arg Ala Lys Glu Ile Gly
    290                 295                 300
```

-continued

Ala Ser Pro Pro Pro Ala Val Asp Ala Ile Leu Gln Lys Asp Asn Gly
305                 310                 315                 320

Asn Asn Phe Asn Lys Pro Ala Pro Thr Phe Pro Tyr Leu Leu Thr Pro
            325                 330                 335

Phe Gly Gly Ala Ala Ser Val Cys Ser Leu His Cys Cys Thr Ala Lys
        340                 345                 350

Leu Leu Arg Leu His Glu Leu Leu Glu Asn Pro Thr Leu Glu Val
    355                 360                 365

Ile Leu Phe Gly Glu Ser Leu Arg Thr Asp Asp Gly Leu Pro Arg Arg
370                 375                 380

Glu Lys Glu Gln Leu Ile Ser Val His Leu Pro Val Val Lys Met
385                 390                 395                 400

Ser Pro Ser Gly Gly Phe Ser Glu Leu Gly Gly Ala Leu Lys Ala Ala
            405                 410                 415

Glu Glu Lys Gln Tyr Phe Phe Glu Glu Lys Tyr Leu Ala Asp Glu Leu
            420                 425                 430

Gly Pro Asp Leu Met Ser Met Trp Thr Gln Ser Arg Ala His Trp Leu
        435                 440                 445

Arg Leu Val Lys Glu Asp Trp Glu Arg Leu Cys Arg Arg Asp Pro Glu
450                 455                 460

Arg Thr Lys Phe Thr Trp Asn Asn Ser Ser Ala Met Asn Ala Ala Phe
465                 470                 475                 480

Phe Asp Leu Cys Glu Val Ala Lys Gln Met Ile Gly Leu Leu Asn
            485                 490                 495

Lys Glu Thr Pro Ser Ser Ala Glu Asn His Ser Phe Trp Ile Leu Phe
            500                 505                 510

Ala Ala His Leu Asn Tyr Ala Cys Thr Thr Glu Asn Gly Met Pro Arg
        515                 520                 525

Asp Ala Val Gly Met His Lys Leu Asn Val Lys Leu Lys Asp Phe His
        530                 535                 540

Phe Gly Gly Thr Arg Tyr Leu Lys Asp Met Pro Pro Glu Glu Gln Glu
545                 550                 555                 560

Arg Arg Leu Glu Arg Lys Lys Arg Ile Glu Glu Ala Arg Arg Gly
            565                 570                 575

Ser Ser Ala His Glu Thr His Thr Asp Asn Trp Leu Leu Asn Asp Thr
        580                 585                 590

Phe Asp Tyr Gln Gln Glu Asp Arg Lys Val Glu Phe Glu Glu Asn Gly
        595                 600                 605

Trp Met Thr Pro Glu Ala Tyr Val Lys His Leu Gly Leu Lys Pro Cys
610                 615                 620

Gly Asp Val Thr Ala Ala Ser Pro Thr Glu Pro Ile His Val Leu
625                 630                 635                 640

Val Val Leu Pro Arg Pro Ala Ala Ala Thr Ala Lys Asp Ala Lys
            645                 650                 655

Arg Asp Val Pro Leu Ala Thr Ser Glu Glu Ser Ile Arg Leu Leu Met
            660                 665                 670

Asn Pro Ala Ala Gln Arg Val Leu Arg Gly Lys Ala Arg Asn Val Ala
        675                 680                 685

Leu Pro Ser Pro Leu Ser Phe Gly Gly Val Lys Ile Thr Val Leu Phe
        690                 695                 700

Asp Gly Asp Asp Ile Asp Cys Ile His Pro Asp Phe Val Ile Leu Gln
705                 710                 715                 720

His Leu Leu Ala Thr Ile Glu Glu Asp Glu Ala Ala Lys Ala Arg Val

```
                725                 730                 735
Lys Tyr Trp Ala Arg Val Ala Arg Tyr Cys Val Phe Val Glu Thr
            740                 745                 750

Asp Val Arg Asp Arg Arg His Phe Leu Leu Arg Glu Glu Val Arg Val
            755                 760                 765

Ala Tyr Glu Asp Val Ala Glu Asp Cys Phe Arg Ser Leu His Ala Ala
            770                 775                 780

Ala Tyr Ser Thr Lys Tyr Asn Arg Leu Arg Thr Thr Pro Ser Leu Ile
785                 790                 795                 800

Ala Leu Cys Asn Arg Lys Asn Ile Gly Leu Arg Phe Lys Phe Arg Gly
                805                 810                 815

Ser Pro Leu Asn Thr Ile Ala Leu Val Val Gly Glu Arg Leu Asp
                820                 825                 830

<210> SEQ ID NO 12
<211> LENGTH: 836
<212> TYPE: PRT
<213> ORGANISM: Trypanosoma cruzi

<400> SEQUENCE: 12

Phe Phe Thr Met Lys Gln Lys Arg Gly Lys Gln Asp Val Lys Met Leu
1               5                   10                  15

Glu Ser Thr Pro Pro Gln Leu Leu Pro Lys Lys Gly Arg Leu Glu Ile
                20                  25                  30

Ser Glu Leu Ala Pro Gln Gln Arg Thr Ile Arg Thr Ala Glu Glu Ile
            35                  40                  45

Glu Thr Ala Tyr Asn Glu Ala Val Arg Lys His Pro Phe Tyr Asp Asn
        50                  55                  60

Ala Asp His Thr Ile Asp Phe His Asp Ala Thr Val Phe Arg Asp Ala
65                  70                  75                  80

Arg Gly Val Val Gly Gly Val Phe Leu Pro Gly Ala Leu Pro Ala Phe
                85                  90                  95

Ala Ala Thr Met Ala Ala Asp Val Leu Arg Pro Ala Ala Val Arg Thr
            100                 105                 110

Ser Leu Arg Ser Asn Met Phe Gly Gly Phe Ala Pro Leu Ser Gly Ile
        115                 120                 125

Ala Gly Tyr Phe Asp Tyr Arg Gly Ser Pro Val Glu Leu Lys Cys Arg
    130                 135                 140

Lys Thr Ser Phe Thr Tyr Glu Asn Val His Ser Trp Pro Asn Val Phe
145                 150                 155                 160

Pro Met Ile Asp Tyr Val Ser Ala Ile Tyr Lys Ala Val Phe Pro Glu
                165                 170                 175

Gln Trp Ala Ala Gln Asp Ala Ala Val Pro Asp Ile Val Arg Ile His
            180                 185                 190

Gly Ser Pro Phe Ser Thr Leu Thr Val Asn Gln Gln Phe Arg Thr Ala
        195                 200                 205

Ser His Thr Asp Ala Gly Asp Phe Asp Met Gly Tyr Gly Leu Leu Val
    210                 215                 220

Val Leu Glu Gly Lys Phe Glu Gly Leu Ser Leu Ala Leu Asp Asp Phe
225                 230                 235                 240

Gly Val Cys Phe Arg Met Gln Pro Arg Asp Ile Leu Ile Phe Asn Thr
                245                 250                 255

His Phe Phe His Ser Asn Thr Glu Leu Glu Leu Asp Pro Gly Asp
            260                 265                 270
```

```
Glu Trp Ser Arg Leu Thr Cys Val Cys Tyr Tyr Arg Ala Leu Gly
            275                 280                 285

Glu Pro Ala Cys Val Ala Glu Tyr Glu Arg Arg Leu Ala Arg Ala Lys
        290                 295                 300

Glu Ile Gly Ala Ser Pro Pro Ala Val Asp Ala Ile Ile Gln Lys
305                 310                 315                 320

Asp Asn Gly Asn Asn Phe Asn Lys Pro Ala Pro Thr Phe Thr Tyr Leu
                325                 330                 335

Leu Thr Pro Phe Gly Gly Ala Ala Ser Val Cys Ser Leu His Cys Cys
            340                 345                 350

Thr Ala Lys Leu Leu Arg Leu His Glu Leu Leu Leu Glu Asn Pro Lys
        355                 360                 365

Leu Glu Val Ile Leu Phe Gly Glu Ser Leu Arg Thr Asp Asp Gly Leu
    370                 375                 380

Pro Arg Arg Glu Lys Glu Gln Leu Ile Ser Val His Leu Pro Val Val
385                 390                 395                 400

Val Lys Met Ser Pro Ser Gly Gly Phe Ser Glu Leu Gly Gly Ala Leu
                405                 410                 415

Lys Ala Ala Glu Glu Lys Gln Tyr Phe Phe Glu Glu Lys Tyr Leu Ala
            420                 425                 430

Asp Glu Leu Gly Pro Asp Leu Met Ser Met Trp Thr Gln Ser Arg Ala
        435                 440                 445

His Trp Leu Arg Leu Val Lys Glu Asp Trp Glu Arg Leu Cys Arg Arg
    450                 455                 460

Asp Pro Glu Arg Thr Lys Phe Thr Trp Asn Asn Ser Ser Ala Met Asn
465                 470                 475                 480

Ala Ala Phe Phe Asp Leu Cys Glu Val Ala Lys Gln Met Met Ile Gly
                485                 490                 495

Leu Leu Asn Lys Glu Thr Pro Ser Ser Ala Glu Asn His Ser Phe Trp
            500                 505                 510

Ile Leu Phe Ala Ala His Leu Asn Tyr Ala Cys Ala Thr Glu Asn Gly
        515                 520                 525

Met Pro Arg Asp Ala Val Gly Met His Lys Leu Asn Val Lys Leu Lys
    530                 535                 540

Asp Phe His Phe Gly Gly Thr Arg Tyr Leu Lys Asp Met Pro Pro Glu
545                 550                 555                 560

Glu Gln Glu Arg Arg Leu Glu Arg Lys Lys Arg Ile Glu Glu Ala Arg
                565                 570                 575

Arg Arg Gly Ser Ser Ala His Glu Thr His Thr Asp Asn Trp Leu Leu
            580                 585                 590

Asn Asp Lys Phe Asp Tyr Gln Gln Glu Asp Arg Lys Val Glu Phe Glu
        595                 600                 605

Glu Asn Gly Trp Met Thr Pro Glu Ala Tyr Val Lys His Leu Gly Leu
    610                 615                 620

Lys Pro Cys Gly Asp Val Thr Ala Thr Ser Pro Thr Glu Ser Ile
625                 630                 635                 640

His Val Leu Val Val Leu Pro Arg Pro Val Ala Ala Ala Ala
                645                 650                 655

Lys Asp Ala Lys Arg Asp Val Pro Leu Ala Thr Ser Glu Glu Ser Ile
            660                 665                 670

Arg Leu Leu Met Asn Pro Ala Ala Gln Arg Val Leu Thr Gly Lys Ala
        675                 680                 685

Arg Asn Val Thr Leu Pro Ser Pro Leu Ser Phe Gly Gly Val Lys Ile
```

```
                690                 695                 700
Thr Val Leu Phe Asp Gly Asp Asp Ile Asp Cys Ile His Pro Asp Phe
705                 710                 715                 720

Val Ile Leu Gln His Leu Leu Ala Ala Ile Glu Glu Asp Glu Ala Ala
                725                 730                 735

Lys Ala Arg Val Lys Tyr Trp Ala His Val Ala Arg Tyr Cys Val Phe
                740                 745                 750

Val Val Glu Thr Asp Val Arg Asp Arg Arg His Phe Leu Leu Arg Glu
                755                 760                 765

Glu Val Arg Val Ala Tyr Glu Asp Val Ala Glu Asp Cys Phe Arg Ser
                770                 775                 780

Leu His Ala Ala Ala Tyr Ser Thr Lys Tyr Asn Arg Leu Arg Thr Thr
785                 790                 795                 800

Pro Ser Leu Ile Ala Leu Cys Asn Arg Lys Asn Ile Gly Leu Arg Phe
                805                 810                 815

Lys Phe Arg Gly Ser Pro Leu Asn Thr Ile Ala Leu Ile Val Val Gly
                820                 825                 830

Glu Arg Leu Asp
        835

<210> SEQ ID NO 13
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 13

His His His His His His
1               5

<210> SEQ ID NO 14
<211> LENGTH: 253
<212> TYPE: PRT
<213> ORGANISM: Leishmania tarentolae

<400> SEQUENCE: 14

Ser Asp Gly Ile Pro Leu Arg Gly Glu Asp Glu Lys Val Lys Ala Asn
1               5                   10                  15

Gly Asp Ser Thr Pro Arg Pro Leu Ser Arg Leu Gly Phe Ser Glu
                20                  25                  30

Thr Asn Leu Met Val Ser Thr Ala Val Glu Lys Lys Tyr Leu Asp
            35                  40                  45

Ser Glu Phe Leu Leu His Cys Ile Ser Ala Gln Leu Leu Asp Met Trp
50                  55                  60

Lys Gln Ala Arg Ala Arg Trp Leu Glu Leu Val Gly Lys Glu Trp Ala
65                  70                  75                  80

His Met Leu Ala Leu Asn Pro Gly Arg Lys Asp Phe Leu Trp Lys Asn
                85                  90                  95

Gln Ser Glu Met Asn Ser Ala Phe Phe Asp Leu Cys Glu Val Gly Lys
                100                 105                 110

Gln Val Met Leu Gly Leu Leu Gly Lys Glu Val Ala Leu Pro Lys Glu
                115                 120                 125

Glu Gln Ala Phe Trp Ile Met Tyr Ala Val His Leu Ser Ala Ala Cys
            130                 135                 140

Ala Glu Glu Leu His Met Pro Glu Val Ala Met Ser Leu Arg Lys Leu
```

```
                145                 150                 155                 160
Asn Val Lys Leu Lys Asp Phe Asn Phe Gly Gly Thr Arg Tyr Phe Lys
                    165                 170                 175
Asp Met Pro Pro Glu Lys Lys Arg Arg Met Glu Arg Lys Gln Arg
                180                 185                 190
Ile Glu Glu Ala Arg Arg His Gly Met Pro Ser Gly Ser His Glu Lys
                    195                 200                 205
Arg Ala Asn Trp Leu Thr Asn Asp Ser Phe Asp Tyr Gln Thr Glu Asp
                    210                 215                 220
Cys Val Ile Asp Tyr Ala Gln His Lys Trp Val Leu Pro Ala Leu His
225                 230                 235                 240
Ala Lys Glu Val Thr Lys Thr Val Arg Thr Gly Glu Leu
                    245                 250

<210> SEQ ID NO 15
<211> LENGTH: 252
<212> TYPE: PRT
<213> ORGANISM: Leishmania braziliensis
<220> FEATURE:
<221> NAME/KEY: MOD_RES
<222> LOCATION: (236)..(236)
<223> OTHER INFORMATION: Any amino acid

<400> SEQUENCE: 15

Ser Asp Gly Ile Pro Leu Arg Gly Asp Glu Lys Leu Lys Ala Asn
1               5                   10                  15
Gly Asp Thr Gly Ala Lys Pro Leu Ser Arg Leu Gly Gly Phe Ser Glu
                20                  25                  30
Thr Asp Leu Met Val Ser Thr Ala Ala Glu Lys Arg Lys Tyr Leu Asp
                35                  40                  45
Ser Glu Phe Leu Ser His Cys Ile Ser Ala Gln Leu Leu Asp Met Trp
            50                  55                  60
Lys Gln Ala Arg Ala Arg Trp Leu Glu Leu Val Gly Lys Glu Trp Lys
65                  70                  75                  80
His Met Leu Thr Leu Asn Pro Glu Arg Lys Asp Phe Leu Trp Lys Asn
                85                  90                  95
Arg Ser Glu Met Asn Ser Ala Phe Phe Asp Leu Cys Glu Val Gly Lys
                100                 105                 110
Gln Val Met Leu Gly Leu Leu Asp Lys Glu Ala Ala Leu Pro Lys Glu
                115                 120                 125
Glu Gln Ala Phe Trp Thr Met Tyr Ala Val His Leu Ser Ala Ala Cys
                130                 135                 140
Ala Glu Glu Leu His Met Pro His Asp Ala Met Ser Leu Arg Lys Leu
145                 150                 155                 160
Asn Val Lys Leu Lys Asp Phe Asn Phe Gly Gly Thr Arg Tyr Phe Lys
                    165                 170                 175
Asp Met Pro Pro Glu Glu Gln Gln Arg Arg Met Glu Arg Lys Gln Arg
                180                 185                 190
Ile Glu Glu Ala Arg Arg His Gly Met Thr Gly Ala His Glu Lys Arg
                    195                 200                 205
Ala Asn Trp Leu Thr Asn Asp Ser Phe Asp Tyr Gln Thr Glu Asp Cys
                210                 215                 220
Val Val Asp Tyr Ala Lys His Lys Trp Val Leu Xaa Glu Arg His Ala
225                 230                 235                 240
Lys Ala Val Thr Lys Asn Val His Thr Ala Trp Leu
                    245                 250
```

<210> SEQ ID NO 16
<211> LENGTH: 253
<212> TYPE: PRT
<213> ORGANISM: Leishmania donovani

<400> SEQUENCE: 16

Ser Asp Gly Ile Pro Leu Arg Gly Glu Glu Lys Leu Lys Ala Asn
1               5                   10                  15

Ser Asp Ser Ala Ser Arg Pro Leu Ser Arg Leu Gly Gly Phe Ser Glu
            20                  25                  30

Thr Asn Leu Met Val Ser Thr Ala Val Glu Lys Lys Tyr Leu Asn
            35                  40                  45

Ser Glu Phe Leu Ser His Phe Ile Ser Ala Gln Leu Leu Asp Met Trp
    50                  55                  60

Lys Gln Ala Arg Gly Lys Trp Leu Glu Leu Val Gly Arg Glu Trp Thr
65                  70                  75                  80

His Met Leu Ala Leu Asn Pro Glu Arg Lys Asp Phe Leu Trp Lys Asn
                85                  90                  95

Gln Ser Glu Met Asn Ser Ala Phe Phe Asp Leu Cys Glu Val Gly Lys
            100                 105                 110

Gln Val Met Leu Gly Leu Leu Gly Lys Glu Ala Ala Leu Pro Lys Glu
        115                 120                 125

Glu Gln Ala Phe Trp Thr Met Tyr Ala Val His Leu Asn Ala Ala Cys
    130                 135                 140

Ala Glu Glu Leu Asn Met Pro His Val Ala Met Ser Leu Arg Lys Leu
145                 150                 155                 160

Asn Val Lys Leu Lys Asp Phe Asn Phe Gly Gly Thr Arg Tyr Phe Lys
                165                 170                 175

Asp Met Pro Pro Glu Glu Gln Lys Arg Arg Met Glu Arg Lys Gln Arg
            180                 185                 190

Ile Glu Glu Ala Arg Arg His Gly Met Ser Ser Gly Ala His Glu Lys
        195                 200                 205

Arg Ala Asn Trp Leu Thr Asn Asp Ser Phe Asp Tyr Gln Thr Glu Asp
    210                 215                 220

Cys Val Val Asp Tyr Ala Gln His Lys Trp Val Pro Pro Ala Leu His
225                 230                 235                 240

Ala Lys Glu Ile Thr Lys Asn Val Arg Asn Gly Glu Leu
                245                 250

<210> SEQ ID NO 17
<211> LENGTH: 253
<212> TYPE: PRT
<213> ORGANISM: Leishmania infantum

<400> SEQUENCE: 17

Ser Asp Gly Ile Pro Leu Arg Gly Glu Glu Lys Leu Lys Ala Asn
1               5                   10                  15

Ser Asp Ser Ala Ser Arg Pro Leu Ser Arg Leu Gly Gly Phe Ser Glu
            20                  25                  30

Thr Asn Leu Met Val Ser Thr Ala Val Glu Lys Lys Tyr Leu Asn
            35                  40                  45

Ser Glu Phe Leu Ser His Phe Ile Ser Ala Gln Leu Leu Asp Met Trp
    50                  55                  60

Lys Gln Ala Arg Gly Lys Trp Leu Glu Leu Val Gly Arg Glu Trp Thr
65                  70                  75                  80

His Met Leu Ala Leu Asn Pro Glu Arg Lys Asp Phe Leu Trp Arg Asn
                85                  90                  95

Gln Ser Glu Met Asn Ser Ala Phe Phe Asp Leu Cys Glu Val Gly Lys
            100                 105                 110

Gln Val Met Leu Gly Leu Leu Gly Lys Glu Ala Ala Leu Pro Lys Glu
        115                 120                 125

Glu Gln Ala Phe Trp Thr Met Tyr Ala Val His Leu Asn Ala Ala Cys
    130                 135                 140

Ala Glu Glu Leu Asn Met Pro His Val Ala Met Ser Leu Arg Lys Leu
145                 150                 155                 160

Asn Val Lys Leu Lys Asp Phe Asn Phe Gly Gly Thr Arg Tyr Phe Lys
                165                 170                 175

Asp Met Pro Pro Glu Glu Gln Lys Arg Arg Met Glu Arg Lys Gln Arg
            180                 185                 190

Ile Glu Glu Ala Arg Arg His Gly Met Ser Ser Gly Ala His Glu Lys
        195                 200                 205

Arg Ala Asn Trp Leu Thr Asn Asp Ser Phe Asp Tyr Gln Thr Glu Asp
    210                 215                 220

Cys Val Phe Asp Tyr Ala Gln His Lys Trp Val Pro Pro Ala Leu His
225                 230                 235                 240

Ala Lys Glu Ile Thr Lys Asn Val Arg Ser Gly Glu Leu
                245                 250

<210> SEQ ID NO 18
<211> LENGTH: 253
<212> TYPE: PRT
<213> ORGANISM: Leishmania major

<400> SEQUENCE: 18

Ser Asp Gly Ile Pro Leu Arg Gly Glu Asp Lys Lys Leu Lys Ala Asn
1               5                   10                  15

Ser Asp Ser Ala Ser Arg Pro Leu Ser Arg Leu Gly Gly Phe Ser Glu
            20                  25                  30

Thr Asn Leu Met Val Ser Thr Ala Val Glu Lys Lys Lys Tyr Leu Asn
        35                  40                  45

Ser Glu Phe Leu Ser His Phe Ile Ser Ala Gln Leu Leu Asp Met Trp
    50                  55                  60

Lys Gln Ala Arg Gly Lys Trp Leu Glu Leu Val Gly Arg Glu Trp Thr
65                  70                  75                  80

His Met Leu Ala Leu Asn Pro Glu Arg Lys Asp Phe Leu Trp Lys Asn
                85                  90                  95

Gln Ser Glu Met Asn Ser Ala Phe Phe Asp Leu Cys Glu Val Gly Lys
            100                 105                 110

Gln Val Met Leu Gly Leu Leu Gly Lys Glu Val Ala Leu Pro Lys Glu
        115                 120                 125

Glu Gln Ala Phe Trp Thr Met Tyr Ala Val His Leu Asn Ala Ala Cys
    130                 135                 140

Ala Glu Glu Leu His Met Pro His Val Ala Met Ser Leu Arg Lys Leu
145                 150                 155                 160

Asn Val Lys Leu Lys Asp Phe Asn Phe Gly Gly Thr Arg Tyr Phe Lys
                165                 170                 175

Asp Met Pro Pro Glu Glu Gln Lys Arg Arg Met Glu Arg Lys Gln Arg
            180                 185                 190

Ile Glu Glu Ala Arg Arg His Gly Met Ser Ser Gly Ala His Glu Lys

```
                    195                 200                 205
Arg Ala Asn Trp Leu Thr Asn Asp Ser Phe Asp Tyr Gln Thr Glu Asp
    210                 215                 220

Cys Val Val Asp Tyr Ala Gln His Lys Trp Pro Pro Ala Leu His
225                 230                 235                 240

Ala Lys Glu Ile Thr Lys Asn Val Arg Thr Gly Glu Leu
                245                 250
```

<210> SEQ ID NO 19
<211> LENGTH: 253
<212> TYPE: PRT
<213> ORGANISM: Crithidia fasciculate

<400> SEQUENCE: 19

```
Ser Asp Gly Ile Pro Leu Arg Ala Ala Glu Gln Lys Leu Lys Ala Asn
1               5                   10                  15

Ala Asp Gly Ala Ser Arg Gly Val Thr Ser Ser Gly Gly Phe Ser Glu
                20                  25                  30

Ser Asp Ala Val Leu Thr Thr Ala Val Glu Lys Ser Lys Tyr Leu Glu
                35                  40                  45

Arg Asp His Leu Ser Gln Cys Ile Ser Ala Glu Leu Leu Ala Met Trp
    50                  55                  60

Val Glu Ala Arg Lys His Trp Leu Arg Leu Val Ala Thr Glu Trp Ala
65              70                  75                  80

Arg Met Ile Ala Thr Ala Pro Glu Arg Thr Asp Phe Leu Trp Lys Asn
                85                  90                  95

Lys Ser Pro Met Asn Thr Ala Phe Phe Asp Leu Cys Glu Val Ala Lys
                100                 105                 110

Gln Val Met Leu Gly Leu Leu Asp Lys Glu Thr Ala Thr Pro Thr Glu
            115                 120                 125

Glu Arg His Phe Trp Ser Val Tyr Ala Ala His Leu His Arg Ala Cys
    130                 135                 140

Ala Glu Arg Leu Met Met Pro Glu Glu Ala Met Ser Leu Arg Lys Leu
145                 150                 155                 160

Asn Val Lys Leu Lys Asp Phe Ser Phe Gly Gly Thr Arg Tyr Phe Lys
                165                 170                 175

Asp Met Pro Val Glu Glu Gln Leu Arg Arg Val Ala Arg Lys Ala Ser
                180                 185                 190

Ile Glu Glu Ala Arg Arg Arg Ser Thr Ala Ala Lys Asp Gly Glu Gln
        195                 200                 205

Arg Ser Asn Trp Leu Thr Asn Asp Ala Phe Asp Tyr Gln Thr Glu Asp
    210                 215                 220

Cys Glu Val Asp Tyr Ala Gly His Gly Trp Ala Val Pro Lys Gln His
225                 230                 235                 240

Ala Lys Thr Val Thr Ala Asn Val His Gln Glu Ala Val
                245                 250
```

<210> SEQ ID NO 20
<211> LENGTH: 252
<212> TYPE: PRT
<213> ORGANISM: Trypanosoma brucei

<400> SEQUENCE: 20

```
Ala Asp Gly Leu Pro Arg Arg Ala Pro Glu Glu Ile Ile Pro Val His
1               5                   10                  15

Lys His Thr Asn Val Gln Met His Tyr Leu Gly Gly Phe Ser Glu Lys
```

```
            20                  25                  30
Gly Asp Ile Leu Asn Glu Ala Met Asn Lys Arg His Tyr Leu Asp Lys
         35                  40                  45
Glu Asn Leu Gln Lys Met Phe Gly Glu Glu Phe Val Asn Ile Trp Thr
 50                  55                  60
Gln Ser Arg Thr His Trp Leu Gln Leu Val Lys Lys Glu Trp Glu His
 65                  70                  75                  80
Gln Lys Glu Thr Asn Pro Thr Arg Thr Arg Phe Ser Trp Asn Asn Thr
                 85                  90                  95
Ser Ala Met Asn Phe Ala Phe Phe Asp Leu Cys Asp Val Ala Lys Gln
                100                 105                 110
Leu Met Cys Gly Ala Phe Gly Asp Arg Glu Val Asn Lys Lys Glu Glu
            115                 120                 125
Gln Ser Phe Trp Gly Met Phe Ala Ala His Leu Asp Asn Ala Cys Ile
        130                 135                 140
Asn Glu Ile Gly Met Leu Gln Gly Ser Met Gly Met His Lys Leu Asn
145                 150                 155                 160
Val Lys Leu Lys Asp Tyr Asn Phe Gly Gly Thr Arg Tyr Leu Lys Asp
                165                 170                 175
Met Pro Pro Glu Glu Gln Arg Arg Arg Arg Arg Leu Glu Ile
                180                 185                 190
Glu Gln Ala Arg Arg Ala Pro Ile Cys Asp Ser Glu Ser Gly Asp
            195                 200                 205
Trp Leu Arg Asn Glu Ala Phe Asp Tyr Gln Thr Glu Asp Val Ala Val
        210                 215                 220
Asn Tyr Glu Arg Glu Gln Trp Ile Thr Pro Glu Asn Asn Ala Lys Arg
225                 230                 235                 240
Phe Gly Phe Pro Glu Arg Gly Val Tyr Gly Ala Glu
                245                 250

<210> SEQ ID NO 21
<211> LENGTH: 253
<212> TYPE: PRT
<213> ORGANISM: Trypanosoma cruzi

<400> SEQUENCE: 21

Asp Asp Gly Leu Pro Arg Arg Glu Lys Glu Gln Leu Ile Ser Val His
  1               5                  10                  15
Leu Pro Val Val Val Lys Met Ser Pro Ser Gly Gly Phe Ser Glu Leu
                 20                  25                  30
Gly Gly Ala Leu Lys Ala Ala Glu Lys Gln Tyr Phe Phe Glu Glu
             35                  40                  45
Lys Tyr Leu Ala Asp Glu Leu Gly Pro Asp Leu Met Ser Met Trp Thr
 50                  55                  60
Gln Ser Arg Ala His Trp Leu Arg Leu Val Lys Glu Asp Trp Glu Arg
 65                  70                  75                  80
Leu Cys Arg Arg Asp Pro Glu Arg Thr Lys Phe Thr Trp Asn Asn Ser
                 85                  90                  95
Ser Ala Met Asn Ala Ala Phe Phe Asp Leu Cys Glu Val Ala Lys Gln
                100                 105                 110
Met Met Ile Gly Leu Leu Asn Lys Glu Thr Pro Ser Ser Ala Glu Asn
            115                 120                 125
His Ser Phe Trp Ile Leu Phe Ala Ala His Leu Asn Tyr Ala Cys Thr
        130                 135                 140
```

-continued

```
Thr Glu Asn Gly Met Pro Arg Asp Ala Val Gly Met His Lys Leu Asn
145                 150                 155                 160

Val Lys Leu Lys Asp Phe His Phe Gly Gly Thr Arg Tyr Leu Lys Asp
                165                 170                 175

Met Pro Pro Glu Glu Gln Glu Arg Arg Leu Glu Arg Lys Lys Arg Ile
            180                 185                 190

Glu Glu Ala Arg Arg Arg Gly Ser Ser Ala His Glu Thr His Thr Asp
        195                 200                 205

Asn Trp Leu Leu Asn Asp Thr Phe Asp Tyr Gln Gln Glu Asp Arg Lys
        210                 215                 220

Val Glu Phe Glu Glu Asn Gly Trp Met Thr Pro Glu Ala Tyr Val Lys
225                 230                 235                 240

His Leu Gly Leu Lys Pro Cys Gly Asp Val Thr Ala Ala
                245                 250
```

MULTIMER GLYCOSYLATED NUCLEIC ACID BINDING PROTEIN CONJUGATES AND USES THEREOF

RELATED PATENT APPLICATION

This patent application claims the benefit of U.S. Provisional Application No. 61/480,697 filed on Apr. 29, 2011, entitled MULTIMER GLYCOSYLATED NUCLEIC ACID BINDING PROTEIN CONJUGATES AND USES THEREOF, naming Karsten Schmidt as inventor. The entirety of the foregoing provisional patent application is incorporated herein by reference.

SEQUENCE LISTING

The instant application contains a Sequence Listing which has been submitted in ASCII format via EFS-Web and is hereby incorporated by reference in its entirety. Said ASCII copy, created on May 30, 2012, is named SEQ6033U.txt and is 98,298 bytes in size.

FIELD

The technology relates in part to multimer conjugates that can interact with nucleic acid containing glycosylated moieties. The conjugates provided herein can be used to enrich for or detect the presence, absence or amount of various types of glycosylated nucleic acid in a sample.

SUMMARY

Provided in some embodiments is a composition comprising a multimer that comprises a scaffold conjugated to two or more polypeptides, which polypeptides specifically interact with a nucleic acid containing beta-D-glucosyl-hydroxymethylcytosine and/or a nucleic acid containing beta-D-glucosyl-hydroxymethyluracil. In some embodiments, the two or more polypeptides specifically interact with a nucleic acid containing beta-D-glucosyl-hydroxymethylcytosine. Often, the nucleic acid containing beta-D-glucosyl-hydroxymethylcytosine is generated from nucleic acid containing 5-hydroxymethylcytosine. In some embodiments, the two or more polypeptides specifically interact with a nucleic acid containing beta-D-glucosyl-hydroxymethyluracil.

In some embodiments, the scaffold is chosen from an antibody, an antibody fragment, a multimerized binding partner that interacts with a binding partner counterpart in each of the polypeptides, a polymer, and a polyfunctional molecule. In some instances, the scaffold is coupled to a solid support. In some cases, the scaffold is a multimerized ligand that interacts with an amino acid sequence in the polypeptides. In some embodiments, the scaffold is an antibody fragment and sometimes the antibody fragment is an Fc portion of an antibody. Sometimes the Fc portion of the antibody comprises two chains and sometimes the Fc portion of the antibody is a single chain.

In some embodiments, one or more of the polypeptides comprise a full-length native protein that specifically interacts with the beta-D-glucosyl-hydroxymethylcytosine in the nucleic acid and/or the beta-D-glucosyl-hydroxymethyluracil in the nucleic acid. In some embodiments, one or more of the polypeptides comprise a fragment of a native protein that specifically interacts with the beta-D-glucosyl-hydroxymethylcytosine in the nucleic acid and/or the beta-D-glucosyl-hydroxymethyluracil in the nucleic acid. In some embodiments, one or more of the polypeptides comprise a modified protein that specifically interacts with the beta-D-glucosyl-hydroxymethylcytosine in the nucleic acid and/or the beta-D-glucosyl-hydroxymethyluracil in the nucleic acid, which modified protein comprises one or more amino acid modifications to a full-length native protein. In some embodiments, one or more of the polypeptides comprise a modified protein that specifically interacts with the beta-D-glucosyl-hydroxymethylcytosine in the nucleic acid and/or the beta-D-glucosyl-hydroxymethyluracil in the nucleic acid, which modified protein comprises one or more amino acid modifications to a fragment of a full-length native protein.

In some embodiments, the native protein is from a kinetoplastid flagellate organism. In some embodiments, the kinetoplastid flagellate organism is chosen from a *Trypanosoma* spp. organism, *Leishmania* spp. organism, *Crithidia* spp. organism and *Euglena* spp. organism. In some cases, the *Trypanosoma* spp. organism is chosen from *T. brucei* and *T. cruzi*. In some cases, the *Leishmania* spp. organism is chosen from *L. tarentolae, L. aethiopica, L. braziliensis, L. donovani, L. infantum, L. major* strain Friedlin and *L. mexicana*. In some cases, the *Crithidia* spp. organism is *C. fasciculata*.

In some embodiments, the native protein comprises a polypeptide sequence selected from SEQ ID NOs:1 to 12. In some embodiments, the fragment of the native protein comprises amino acids 382 to 561 of SEQ ID NO: 1 or substantially identical polypeptide thereof. In some cases, the native protein or fragment of the native protein comprises an alpha helix 4 of *L. tarentolae* polypeptide or substantially identical polypeptide thereof. In some cases, the fragment of the native protein or fragment of the native protein comprises one or more amino acids chosen from amino acids at positions 387, 388, 389, 390, 391, 399, 402, 411, 423, 427, 430, 431, 433, 434, 438, 446, 448, 451, 453, 455, 457, 459, 560, 462, 463, 464, 465, 466, 467, 469, 471, 472, 474, 476, 487, 491, 492, 496, 498, 499, 502, 503, 509, 518, 519, 520, 521, 522, 523, 524, 525, 528, 529, 530, 531, 532, 533, 535, 536, 537, 538, 540, 541, 544, 545, 548, 552, 553, 555, 556, 557, 571, 572, 574, 577, 578, 579, 580, 582, 583 and 593 of *L. tarentolae*, or corresponding amino acids thereof.

In some embodiments, the polypeptides in the multimer specifically bind to the nucleic acid containing beta-D-glucosyl-hydroxymethylcytosine and/or the nucleic acid containing beta-D-glucosyl-hydroxymethyluracil. In some cases, the two or more polypeptides in the multimer have the same amino acid sequence. In some cases, the two or more polypeptides in the multimer have different amino acid sequences. In some embodiments, the multimer is conjugated to one or more signal generating molecules. In some cases, the scaffold is a polypeptide. In some cases, the scaffold, or portion thereof, and the polypeptides that specifically interact with a nucleic acid containing beta-D-glucosyl-hydroxymethylcytosine and/or a nucleic acid containing beta-D-glucosyl-hydroxymethyluracil are contiguous.

Also provided in some embodiments is a nucleic acid comprising a polynucleotide that encodes a multimer of any of the above compositions comprising any of the corresponding embodiments.

Also provided in some embodiments is an expression vector comprising any of the above polynucleotides.

Also provided in some embodiments is a cell comprising any of the above nucleic acids or any of the above expression vectors.

Also provided in some embodiments is a composition comprising a solid support to which a multimer of any of the above compositions comprising any of the corresponding embodiments is conjugated.

Also provided in some embodiments is a method for manufacturing a multimer of any of the above compositions comprising any of the corresponding embodiments, which comprises conjugating the scaffold to the polypeptides that specifically interact with a nucleic acid containing beta-D-glucosyl-hydroxymethylcytosine and/or a nucleic acid containing beta-D-glucosyl-hydroxymethyluracil. In some embodiments, the method comprises expressing the multimer from any of the above nucleic acids or any of the above expression vectors. In some embodiments, the method comprises expressing the multimer in any of the above cells.

Also provided in some embodiments is a method for detecting the presence, absence or amount of nucleic acid containing beta-D-glucosyl-hydroxymethylcytosine and/or a nucleic acid containing beta-D-glucosyl-hydroxymethyluracil in a sample, comprising contacting the sample that may contain nucleic acid containing beta-D-glucosyl-hydroxymethylcytosine and/or a nucleic acid containing beta-D-glucosyl-hydroxymethyluracil with a multimer of any of the above compositions comprising any of the corresponding embodiments, determining the presence, absence or amount of the multimer that specifically interacts with the nucleic acid in the sample, whereby the presence, absence or amount of nucleic acid containing beta-D-glucosyl-hydroxymethylcytosine and/or a nucleic acid containing beta-D-glucosyl-hydroxymethyluracil in a sample is determined. In some instances, the method of is performed in vitro.

Certain embodiments are described further in the following description, examples, claims and drawings.

BRIEF DESCRIPTION OF THE DRAWINGS

The drawings illustrate embodiments of the technology and are not limiting. For clarity and ease of illustration, the drawings are not made to scale and, in some instances, various aspects may be shown exaggerated or enlarged to facilitate an understanding of particular embodiments.

FIG. 1 shows a multiple sequence alignment of JBP1 from *Leishmania* SEQ ID NOS 14, 2 and 15-18, respectively, in order of appearance), *Trypanosoma* (SEQ ID NOS 20-21, respectively, in order of appearance) and *Crithidia* (SEQ ID NO: 19). A DNA binding domain of JBP1 is boxed. Fully conserved residues are in bold and black text on a gray background and conserved residues are in bold gray text. The secondary structure elements and residue numbers correspond to the *L. tarantolae* protein, the sequence of which is set forth in SEQ ID NO: 1.

DETAILED DESCRIPTION

Provided herein are multimer conjugates which comprise the DNA-binding domain of a protein belonging to the family J-DNA binding proteins (JBPs) and a scaffold, and nucleic acid molecules that encode such conjugates or polypeptide portions thereof. In addition, vectors and host cells which comprise the nucleic acid molecules and polypeptides which are encoded by the nucleic acid molecules, solid supports to which the polypeptide conjugates can be conjugated, as well as processes for producing the polypeptides and methods for detecting the presence, absence or amount of nucleic acid containing glycosylated moieties in a sample are provided.

In some embodiments, the conjugates comprise a scaffold linked to two or more polypeptides that specifically interact with a nucleic acid containing beta-D-glucosylated nucleobases such as beta-D-glucosyl-hydroxymethylcytosine (i.e. beta-glu-5hmC, hereinafter referred to as "H-DNA") or beta-D-glucosyl-hydroxymethyluracil (i.e. beta-glu-5hmU, a.k.a. J-DNA). The scaffold can be chosen from an antibody, an antibody fragment, a multimerized binding partner that interacts with a binding partner counterpart in each of the polypeptides, a polymer, and a polyfunctional molecule, in certain instances. The polypeptides can be from a kinetoplastid flagellate organism and may comprise a full-length native or modified protein or a fragment thereof that specifically interacts with the beta-D-glucosyl-hydroxymethylcytosine or beta-D-glucosyl-hydroxymethyluracil in the nucleic acid, in some embodiments. In some instances, the conjugates provided herein are coupled to a solid support. The conjugates provided herein can be used to enrich for or detect the presence, absence or amount of hydroxymethylcytosine, beta-D-glucosyl-hydroxymethylcytosine or beta-D-glucosyl-hydroxymethyluracil-containing nucleic acid in a sample.

The multimer conjugates provided herein comprise a scaffold that can be conjugated to two or more polypeptides, such as JBP or a fragment thereof, thereby forming a multimer. A multimer is a group of two or more associated molecules (i.e. subunits). The subunits of a multimer can be identical as in a homomultimeric molecule or different as in a heteromultimeric molecule. Examples multimers include, dimers, trimers, etc. By forming a dimer, for example, the scaffold of a multimer conjugate provided herein brings the J-DNA binding domain of one polypeptide of the conjugate into close proximity to the J-DNA binding domain of another polypeptide of the conjugate. This allows bivalent, and in some cases where more than two JBPs are conjugated to the scaffold, multivalent, interactions between the J-DNA binding proteins and H-DNA and/or J-DNA, which can lead to high affinity binding as a result of exponentially increased avidity. As used herein, the term "avidity" refers to the strength of the multiple interactions between a multivalent protein (e.g. the multimer conjugates provided herein) and its binding target (e.g. H-DNA or J-DNA). Accordingly, the multimer conjugates provided herein are capable of binding to H-DNA and/or J-DNA via two or more J-DNA binding domains which are part of the multimer conjugate. In some instances, dimerization can lead to a 100-fold increase in the overall binding constant; for higher degree multimers the increase can be exponential, in some instances (see e.g. Kuby Immunology, 6th edition, Richard A. Goldsby—2007, W.H. Freeman & Company, Page 148). In some embodiments, the binding affinities of the multimer conjugates provided herein for H-DNA and/or J-DNA can be further increased by including the J-DNA binding domains, or fragments thereof, of the JBP proteins, since, in some cases, the full-length JBP may contain domains that interact with other proteins or non-J-DNA or non-H-DNA.

The multimer conjugates provided herein can be produced by generation of subunit conjugates (i.e. one or more JBP polypeptides, or fragments thereof, conjugated to a scaffold via an optional linker) whereby the subunits, when co-expressed or admixed, form multimers. The multimer conjugates also can be produced by the conjugation of two or more JBP polypeptides, or fragments thereof, to a scaffold comprising sites for conjugation of multiple JBP polypeptides or fragments thereof.

The multimer conjugates provided herein can be used as a diagnostic tool for isolating, purifying enriching and/or detecting H-DNA or J-DNA, for example, even if the H-DNA or J-DNA, or the H-DNA precursor hydroxymethylcytosine is present in very small amounts, e.g., about more than 10 ng, less than 10 ng, less than 7.5 ng, less than 5 ng, less than 2.5 ng, less than 1 ng, less than 0.1 ng, or about 0.01 ng as described herein. Generally, 1 ng of human or mammalian DNA equals about 330 genome equivalents or "copies". In some embodiments, H-DNA or J-DNA can be purified, enriched and/or detected with between about 1 to 500 copies present in the sample. For example, H-DNA or J-DNA can be purified, enriched and/or detected with between about 1 to 10, 1 to 20, 1 to 50, 1 to 100, or 1 to 200 copies present in the sample. Accordingly, due to the multivalent structure and function the multimeric conjugates provided herein, they can be applied to various applications including multi-step procedures in a single tube assay (e.g. specific separation, enrichment and/or detection of H-DNA or J-DNA).

Scaffold

The multimer conjugates provided herein comprise a scaffold. A scaffold can be any type of molecule or material that can be conjugated to two or more polypeptides, such as, a JBP or fragment thereof, thereby forming a multimer. In some embodiments, the JBP or fragment thereof is conjugated to the scaffold via a covalent linkage. The covalent linkage can be direct or indirect, such as, for example, via a linker. Linkers are described in further detail herein below. In some embodiments, the JBP or fragment thereof is conjugated to the scaffold via non-covalent interactions.

A scaffold can be, for example, an antibody, an antibody fragment, an immunoglobulin chain, a fragment of an immunoglobulin chain, a multimerized binding partner that interacts with a binding partner counterpart in each of the polypeptides, a polymer, or a polyfunctional molecule. As used herein, a "polyfunctional molecule" can be any molecule that contains two or more binding partners that can interact with a binding partner counterpart conjugated to or expressed within each of the polypeptides. Such binding partner interactions can lead to non-covalent interactions or covalent linkages. Non-limiting examples of binding partner pairs include chemical reactive groups (e.g., sulfhydryl/maleimide, sulfhydryl/haloacetyl derivative, amine/isotriocyanate, amine/succinimidyl ester, amine/sulfonyl halides, and any pairs that can form an amide, ether, carbon-carbon or other relatively stable linkage, antibody/antigen, antibody/antibody, antibody/antibody fragment, antibody/antibody receptor, antibody/protein A or protein G, hapten/anti-hapten, biotin/avidin, biotin/streptavidin, folic acid/folate binding protein, vitamin B12/intrinsic factor).

In some embodiments, the scaffold is a multimerized ligand that interacts with an amino acid sequence in the polypeptides (e.g. multimerized FK506 or FK-506 analog molecules as part of the scaffold and FK506 binding protein linked to the JBP or fragment thereof). In some embodiments, the scaffold is an antibody fragment such as, for example, an Fc portion of an antibody. In some cases, the Fc portion of the antibody comprises five or six chains (e.g. as in IgM). In some cases, the Fc portion of the antibody comprises four chains (as described Shopes, J. Immunol. 1992 May 1; 148(9):2918-22). In some cases, the Fc portion of the antibody comprises two chains. In some cases, the Fc portion of the antibody is a single chain.

As used herein, an "Fc portion" of an antibody comprises at least a portion of the constant region of an immunoglobulin heavy chain molecule. In some embodiments, the Fc region can be limited to the constant domain hinge region and the CH2 and CH3 domains. In some embodiments, the Fc region can be limited to a portion of the hinge region, the portion being capable of forming intermolecular disulfide bridges, and the CH2 and CH3 domains, or functional equivalents thereof. In some embodiments, the Fc portion minimally comprises CH regions which embody the properties of the multimer conjugates described herein.

In some embodiments, the constant region (Fc) contains one or more amino acid substitutions when compared to constant regions known in the art. In some cases, the Fc region contains 1 to 100, 1 to 90, 1 to 80, 1 to 70, 1 to 60, 1 to 50, 1 to 40, 1 to 30, 1 to 20, 1 to 10, 1 to 9, 1 to 8, 1 to 7, 1 to 6, 1 to 5, 1 to 4, 1 to 3 or 2 or 1 substitution(s). The comparison can be done as is known in the art or as described elsewhere herein. In some embodiments, the constant region comprises at least the CH 1 region, the CH1 and CH2 regions, or the CH1, CH2 and CH3 regions. As is known in the art, the constant region of an antibody contains two immunoglobulin heavy chains which harbor three characteristic immunoglobulin domains composed of about 110 amino acids, where the two immunoglobulin heavy chains are covalently linked via disulfide bonds. In some embodiments, the multimer conjugates comprising a JBP, or fragment thereof, and an Fc portion of an antibody, for example, are folded within a host cell such that the conjugate subunits are joined at the Fc portion in a manner similar or identical to the constant region of an antibody, resulting in a bivalent conjugate as described herein (i.e. a conjugate comprising two J-DNA binding proteins or fragments thereof).

In some embodiments, the constant region is of the IgM, IgA, IgD, IgE, or IgG isotype. In some embodiments, the constant region is of the IgG isotype. In some embodiments the IgG isotype is of class IgGl, IgG2, IgG3, or IgG4. In some embodiments, the IgA isotype is of class IgAl or IgA2. In some embodiments, the isotypes are of vertebrate origin. In some embodiments, the isotypes are of mammalian origin, such as, for example, mouse, rat, goat, horse, donkey, camel, chimpanzee, or human origin. In some embodiments, the constant region is of chicken or duck origin. As described herein, the multimer conjugates provided herein can be bivalent conjugates. In some embodiments, the conjugates provided herein can be multivalent conjugates. Such bivalent and multivalent conjugates can be generated by using those Fc regions, or portions thereof, of Ig molecules which are typically multivalent such as IgM pentamers or IgA dimers. It is understood that a J chain polypeptide may be needed to form and stabilize IgM pentamers and IgA dimers.

In some embodiments, the multimeric conjugates provided herein are bifunctional or multifunctional. A "bifunctional" or "multifunctional" conjugate means that the conjugate has, in addition to binding to H-DNA or J-DNA, due to the nature of the scaffold which is part of the conjugate provided herein, further capabilities. For example, the scaffold can offer the possibility to conjugate, link or covalently couple compound(s) or moieties to the scaffold. As used herein, the term "covalently coupled" means that the specified compounds or moieties are either directly covalently bonded to one another, or else are indirectly covalently joined to one another through an intervening moiety or moieties, such as a bridge, spacer, or linkage moiety or moieties.

Such (a) compound(s) may be a detectable substance. Examples of detectable substances include various enzymes, prosthetic groups, fluorescent materials, luminescent materials, bioluminescent materials, radioactive materials, positron emitting metals using various positron emission tomographies, and nonradioactive paramagnetic metal ions. The detectable substance may be coupled or conjugated either directly to the scaffold or indirectly, through an intermediate (such as, for example, a linker known in the art) using techniques known in the art. See, for example, U.S. Pat. No. 4,741,900 for metal ions which can be conjugated to an Fc portion of antibodies for use as diagnostics. Examples of suitable enzymes include horseradish peroxidase, alkaline phosphatase, beta-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin; and examples of suitable radioactive material include 125 1, 131 I, or 99 Tc. Further, the scaffold may be conjugated to a therapeutic moiety such as a cytotoxin, e.g., a cytostatic or cytocidal agent, a therapeutic agent or a radioactive metal ion, e.g., alpha-emitters such as, for example, 213 Bi. A cytotoxin or cytotoxic agent includes any agent that is detrimental to cells. Examples include paclitaxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologues thereof. Therapeutic agents include, but are not limited to, antimetabolites (e.g., methotrexate, 6-mereaptopurine, 6-thioguanine, cytarabine, 5-fluorouracil decarbazine), alkylating agents (e.g., mechlorethamine, thioepa chlormbucil, melphalan, carmustine (BSNU) and lomustine (CCNU), cyclothosphamide, busulfan, dibromomannitol, streptozotocin, mitomycin C, and cis-dichlorodiamine platinum (11) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine and vinblastine).

Furthermore, the scaffold may be coupled or conjugated to a protein or polypeptide possessing a desired biological activity. Such proteins may include, for example, a toxin such as abrin, ricin A, pseudomonas exotoxin, or diphtheria toxin; a protein such as tumor necrosis factor, alpha-interferon, beta-interferon, nerve growth factor, platelet derived growth factor, tissue plasminogen activator, an apoptotic agent; or a therapeutic agent such as, for example, an antimicrobial agent.

The scaffold also allows attachment of the multimeric conjugate to solid supports, in some embodiments, which are particularly useful for immunoassays or purification of the target H-DNA and/or J-DNA as described herein. The term "solid support" or "solid phase" as used herein refers to a wide variety of materials including solids, semi-solids, gels, films, membranes, meshes, felts, composites, particles, and the like typically used to sequester molecules, and more specifically refers to an insoluble material with which the multimer conjugates provided herein can be associated. Examples of solid supports for use herein include, without limitation, beads (e.g., microbeads, nanobeads) and particles (e.g., microparticles, nanoparticles), glass, cellulose, polyacrylamide, nylon, polycabonate, polystyrene, polyvinyl chloride or polypropylene or the like. In some embodiments, the scaffold is coupled to a solid phase, such as, for example, a protein A or G solid phase such as Protein A or Protein G magnetic beads. Protein A and Protein G have multiple Fc binding sites per molecule and the binding stoichiometry is at least, for example, two Fc containing molecules per Protein A or G molecule. Thus, in some cases, such as embodiments where the conjugate is monomeric, for example, and the scaffold is an Fc region, a dimerization and/or multimerization can be achieved, for example, via binding to Protein A or Protein G solid supports. A multimer can be associated with a solid support by a covalent or non-covalent interaction.

The terms "beads" and "particles" as used herein refer to solid supports suitable for associating with biomolecules, such as, for example, the multimer conjugates provided herein. Beads may have a regular (e.g., spheroid, ovoid) or irregular shape (e.g., rough, jagged), and sometimes are non-spherical (e.g., angular, multi-sided). Particles or beads having a nominal, average or mean diameter of about 1 nanometer to about 500 micrometers can be utilized, such as those having a nominal, mean or average diameter, for example, of about 10 nanometers to about 100 micrometers; about 100 nanometers to about 100 micrometers; about 1 micrometer to about 100 micrometers; about 10 micrometers to about 50 micrometers; about 1, 5, 10, 15, 20, 25, 30, 35, 40, 45, 50, 55, 60, 65, 70, 75, 80, 85, 90, 95, 100, 200, 300, 400, 500, 600, 700, 800 or 900 nanometers; or about 1, 5, 10, 15, 20, 25, 30, 35, 40, 45, 50, 55, 60, 65, 70, 75, 80, 85, 90, 95, 100, 200, 300, 400, 500 micrometers.

A bead or particle can be made of virtually any insoluble or solid material. For example, the bead or particle can comprise or consist essentially of silica gel, glass (e.g. controlled-pore glass (CPG)), nylon, Sephadex®, Sepharose®, cellulose, a metal surface (e.g. steel, gold, silver, aluminum, silicon and copper), a magnetic (e.g., paramagnetic) material, a plastic material (e.g., polyethylene, polypropylene, polyamide, polyester, polyvinylidenedifluoride (PVDF)) and the like. Beads or particles may be swellable (e.g., polymeric beads such as Wang resin) or non-swellable (e.g., CPG). Commercially available examples of beads include without limitation Wang resin, Merrifield resin and Dynabeads®. Beads may also be made as solid particles or particles that contain internal voids.

The scaffold of the multimer conjugates provided herein can be associated with the solid support in any manner suitable for the compositions and methods provided herein. The conjugate scaffold may be in association with a solid support by a covalent linkage or a non-covalent interaction. Non-limiting examples of non-covalent interactions include hydrophobic interactions, polar interactions, pair interactions including without limitation, antibody/antigen, antibody/antibody, antibody/antibody fragment, antibody/antibody receptor, antibody/protein A or protein G, hapten/anti-hapten, biotin/avidin, biotin/streptavidin, folic acid/folate binding protein, vitamin B12/intrinsic factor, nucleic acid/complementary nucleic acid (e.g., DNA, RNA, PNA) and the like.

A multimer, in some embodiments, can be constructed without a discrete scaffold molecule. In such embodiments, two polypeptides in the multimer (e.g., the multimer can include two, or more than two, polypeptides) that specifically interact with a nucleic acid containing beta-D-glucosyl-hydroxymethylcytosine and/or a nucleic acid containing beta-D-glucosyl-hydroxymethyluracil are linked directly or indirectly to one another. A polypeptide pair in the multimer can be linked via a binding partner pair (described above) in certain embodiments. Multimers formed without a discrete scaffold molecule can be linear or branched in some embodiments.

J-Binding Protein 1 (JBP1)

As noted above, a multimer comprises polypeptides that specifically interact with a nucleic acid containing beta-D-glucosyl-hydroxymethylcytosine and/or a nucleic acid containing beta-D-glucosyl-hydroxymethyluracil. As used herein, the term "specifically interact with," or grammatical variants thereof, refers to the polypeptides interacting with nucleic acid containing beta-D-glucosyl-hydroxymethylcytosine and/or beta-D-glucosyl-hydroxymethyluracil more strongly than with nucleic acid not containing beta-D-glucosyl-hydroxymethylcytosine and beta-D-glucosyl-hydroxymethyluracil. Thus, a polypeptide that specifically interacts with nucleic acid containing beta-D-glucosyl-hydroxymethylcytosine interacts with that nucleic acid more strongly than with nucleic acid not containing beta-D-glucosyl-hydroxymethylcytosine. Similarly, a polypeptide that specifically interacts with nucleic acid containing beta-D-glucosyl-hydroxymethyluracil interacts with that nucleic acid more strongly than with nucleic acid not containing beta-D-glucosyl-hydroxymethyluracil. A polypeptide that specifically interacts with a nucleic acid containing beta-D-glucosyl-hydroxymethylcytosine and/or a nucleic acid containing beta-D-glucosyl-hydroxymethyluracil often specifically binds to one or more of such nucleic acids (e.g., binds with greater binding affinity to such a nucleic acid than to a nucleic acid not containing beta-D-glucosyl-hydroxymethylcytosine and/or beta-D-glucosyl-hydroxymethyluracil). A polypeptide may in certain embodiments (i) interact with nucleic acid containing beta-D-glucosyl-hydroxymethylcytosine and not detectably interact with nucleic acid containing beta-D-glucosyl-hydroxymethyluracil, (ii) may not detectably interact with nucleic acid containing beta-D-glucosyl-hydroxymethylcytosine and interact with nucleic acid containing beta-D-glucosyl-hydroxymethyluracil, or (iii) may interact with both types of nucleic acid. A polypeptide in some embodiments may (i) specifically interact with nucleic acid containing beta-D-glucosyl-hydroxymethylcytosine and not detectably interact with nucleic acid containing beta-D-glucosyl-hydroxymethyluracil, (ii) interact with nucleic acid containing beta-D-glucosyl-hydroxymethylcytosine more strongly than with nucleic acid containing beta-D-glucosyl-hydroxymethyluracil, (iii) specifically interact with nucleic acid containing beta-D-glucosyl-hydroxymethyluracil and not detectably interact with nucleic acid containing beta-D-glucosyl-hydroxymethylcytosine, (iv) interact with nucleic acid containing beta-D-glucosyl-hydroxymethyluracil more strongly than with nucleic acid containing beta-D-glucosyl-hydroxymethylcytosine. In certain embodiments, the binding region on the nucleic acid to which a polypeptide that specifically interacts with nucleic acid containing beta-D-glucosyl-hydroxymethylcytosine and/or a nucleic acid containing beta-D-glucosyl-hydroxymethyluracil comprises or consists of beta-D-glucosyl-hydroxymethylcytosine or beta-D-glucosyl-hydroxymethyluracil. Methods for determining relative levels, or for quantifying, interactions and binding between polypeptides and nucleic acid containing beta-D-glucosyl-hydroxymethylcytosine and/or beta-D-glucosyl-hydroxymethyluracil are known in the art.

In some embodiments, a polypeptide specifically interacts with a nucleic acid containing one or more beta-D-glucosyl-hydroxymethylcytosine molecules or units (e.g., 1, 5, 10, 15, 20, 25, 30, 35, 40, 45, 50, 55, 60, 65, 70, 75, 80, 85, 90, 95, 100, 200, 300, 400, 500, 600, 700, 800, 900, 1000, 1100, 1200, 1300, 1400, 1500, 1600, 1700, 1800, 1900, 2000 or more beta-D-glucosyl-hydroxymethylcytosine molecules or units). In some embodiments, a polypeptide specifically interacts with a nucleic acid containing one or more beta-D-glucosyl-hydroxymethyluracil molecules or units (e.g., 1, 5, 10, 15, 20, 25, 30, 35, 40, 45, 50, 55, 60, 65, 70, 75, 80, 85, 90, 95, 100, 200, 300, 400, 500, 600, 700, 800, 900, 1000, 1100, 1200, 1300, 1400, 1500, 1600, 1700, 1800, 1900, 2000 or more beta-D-glucosyl-hydroxymethyluracil molecules or units).

In some embodiments, multimers comprise a scaffold and two or more polypeptides that specifically interact with a nucleic acid containing beta-D-glucosyl-hydroxymethyluracil. As used herein, the terms "beta-D-glucosyl-hydroxymethyluracil", "beta-glucosyl-5-hydroxymethyluracil", "beta-glu-5hmC", "base-J", "J base", "J nucleotide" and "J" are used interchangeably. Beta-D-glucosyl-hydroxymethyluracil is a hypermodified base present in kinetoplastid flagellates, including the *Trypanosoma, Leishmania* and *Crithidia* genera and in *Euglena*, but absent from other eukaryotes, prokaryotes and viruses. Base J is a minor base that can replace about 0.5% of thymidine in the nuclear DNA of kinetoplastida and is often present in the telomeric repeat sequence (GGGTTA)n. Small amounts of base J are also found in other repetitive sequences of *Trypanosoma brucei*, such as, for example, the expression sites of variant surface glycoprotein (VSG) genes and in sequences between transcription units.

In some embodiments, the compositions provided herein comprise conjugate multimers comprising a scaffold and two or more polypeptides that specifically interact with a nucleic acid containing beta-D-glucosyl-hydroxymethylcytosine. As used herein, the terms "beta-D-glucosyl-hydroxymethylcytosine", "beta-glucosyl-5-hydroxymethylcytosine", "beta-glu-5hmC", "base-H", "H base", "H nucleotide" and "H" are used interchangeably. A description of beta-D-glucosyl-hydroxymethylcytosine is presented herein below.

DNA methylation at cytosine residues in mammalian cells an epigenetic modification that can affect gene expression. Typically, this DNA modification involves a cytosine that is modified by a methyl group at the N5 position (5meC). The 5meC modification generally occurs at the CpG dinucleotide sequence and can sometimes occur elsewhere in the genome.

Another type of DNA modification that may be involved in gene regulation is 5-hydroxymethylcytosine (5hmC). The enzyme Tet1, an iron-dependent alpha-ketoglutarate dioxygenase, catalyzes the formation of 5hmC from 5meC. The 5hmC base may be an intermediate in the conversion of 5meC to cytosine, and thus Tet1 may be involved in demethylating DNA. In some cases, Tet2 and Tet1 can catalyze the formation of 5hmC. In some instances, 5hmC is a stable DNA modification and can sometimes be found in specialized non-dividing neurons and other animal tissues. In some cases, 5hmC may be involved in tumorigenesis and/or epigenetic gene regulation. For example, 5hmC in DNA can inhibit the binding of several methyl-CpG-binding domain proteins, i.e. proteins that are known to regulate transcription by interaction with 5meC.

The DNA of wild-type bacteriophage T4 is nearly devoid of cytosine residues, which are replaced by 5hmC. These 5hmC residues are glucosylated by the T4-encoded alpha-glucosyltransferase or beta-glucosyltransferase. In some cases, beta-glucosyltransferase is more efficient when used for in vitro glucosylation assays. The glucosylation of 5hmC residues can be used to mark 5hmC residues in mammalian DNA. Glucosylated 5hmC is chemically similar to beta-glucosyl-5-hydroxymethyluracil, (i.e. the J-base described herein), which is specifically recognized by DNA binding proteins from certain protozoa, such as the JBP1s described herein. JBP1 can also cross-react significantly with beta-glucosyl-5-hydroxymethylcytosine (beta-glu-5hmC) containing DNA (see e.g. Robertson et al., Nucleic Acids Res. 2011 Apr. 1; 39(8):e55). For example, 5hmC can be selectively identified in genomic regions by modifying 5hmC residues in genomic DNA using the T4 beta-glucosyltransferase (beta-gt) to create beta-glu-5hmC residues. In some cases, DNA containing these residues bind J-binding protein 1 (JBP1), allowing for the identification of genomic regions containing 5hmC, such as, for example, promoters of developmentally regulated genes in human embryonic stem (hES) cells.

In some cases, 5-hydroxymethyluracil (5hmC) is not naturally glycosylated in certain organisms. For example, 5-hydroxymethyluracil (5hmC) may not be naturally glycosylated in certain eukaryotes, prokaryotes and viruses, and in some cases, may not be naturally glycosylated in humans and other mammals. Thus, nucleic acid containing 5hmC can be glycosylated, in some embodiments, by methods known in the art and/or described herein, whereby a hydroxymethylcytosine (5hmC) containing nucleic acid is converted to beta-glucosyl-5-hydroxymethylcytosine (beta-glu-5hmC) containing nucleic acid. In some cases, 5hmC is converted to beta-glu-5hmC by the addition of glucose to the hydroxyl group of 5hmC via an enzymatic reaction utilizing T4 beta-glucosyltransferase (T4-BGT). Any method known in the art for converting 5hmC to beta-glu-5hmC can be used in conjunction with the embodiments provided herein, including commercially available kits (e.g. EPIMARK 5-hmC Analysis Kit, New England Biolabs, Ipswich, Mass.).

In some embodiments, the polypeptides that specifically interact with a nucleic acid containing beta-D-glucosyl-hydroxymethylcytosine and/or beta-D-glucosyl-hydroxymethyluracil (i.e. J-DNA binding proteins (JBP)) are J-binding protein 1 (JBP1). JBP1 is a 93 kDa protein originally identified in extracts of *T. brucei, Leishmania* species and *Crithidia fasciculata* (see e.g. Cross et al., (1999) EMBO J. 18:6573-6581). JBP1 binds specifically to base J in duplex DNA. JBP1 can also bind to base H in duplex DNA (see e.g. Robertson et al., Nucleic Acids Res. 2011 Apr. 1; 39(8):e55). Because JBP1 can bind to duplex DNA, the detection and/or enrichment of H-DNA and/or J-DNA by the multimer conjugates provided herein can be performed without denaturing the double-stranded DNA sample, in some embodiments.

JBP1 is essential in *Leishmania*, but not in *T. brucei*. The absence of JBP1 in *T. brucei* has no effect on growth, DNA repeat stability or gene expression, but does result in a 20-fold decrease in J-base level relative to wild-type cells. JBP1 can catalyze the first and rate-limiting step in J-base biosynthesis, the hydroxylation of thymidine in DNA. A weak sequence similarity exists between JBP1 and Fe2+ and 2-oxoglutarate (2-OG)-dependent hydroxylases (dioxygenases). Replacement of each of the four amino acids essential for hydroxylase activity resulted in mutant proteins unable to complement JBP1 function in either *T. brucei* or *Leishmania*, but still able to bind to J-DNA. Thus, thymidine hydroxylase activity and J-DNA binding are independent functions of JBP1.

Another protein in kinetoplastid flagellates which partially shares sequence similarity with JBP1 is J-binding protein 2 (JBP2). JBP1 and JBP2 share 34% identity in their N-terminal halves, which contains the thymidine hydroxylase function of JBP1 and of JBP2. The C-terminal half of JBP2, but not of JBP1, contains a region similar to proteins with SWI2/SNF2-like chromatin remodeling activity. Although JBP1 and JBP2 are unique proteins, a distant homolog of the JBP1/2 hydroxylase domain is the mammalian protein TET1, a fusion partner of the MLL gene in acute myeloid leukemia. TET1 and the related TET2 and TET3 proteins catalyze the conversion of 5-methylcytosine in DNA to 5-hydroxymethylcytosine, a reaction that may play an important role in the epigenetic control of gene expression. JBP and TET proteins have been grouped together in the TET/JBP subfamily of dioxygenases.

The binding of JBP1 to J-DNA has been studied by various methods including competition assays, gel retardation assays, and fluorescence anisotropy polarization (FP) assays. For example, using J base-containing duplex oligonucleotides in a gel retardation assay, it was shown that JBP1 binds to J base-containing oligonucleotides with an affinity between 40 and 140 nM (see e.g. Sabatini et al., (2002) J. Biol. Chem. 277:958-966). A fluorescence anisotropy polarization assay (FP) yielded affinities as low as 13 nM (see e.g. Grover et al., (2007) Angew Chem. Int. Ed. Engl. 46:2839-2843). Binding to J-DNA is highly specific, since competition assays using gel-retardation indicated that a 500-fold excess of T-DNA could not out-compete J-specific DNA binding (see e.g. Sabatini et al., (2002) J. Biol. Chem. 277: 28150-28156). The FP assay showed an affinity for T-DNA about 100 times lower than that for J-DNA (1370 nM compared to 13 nM).

The mode of interaction of JBP1 with J-DNA has been probed with several biochemical methods (see e.g. Sabatini et al., (2002) J. Biol. Chem. 277:958-966; Sabatini et al., (2002) J. Biol. Chem. 277: 28150-28156). Substitution of the hydroxymethylU in the J-base by hydroxymethylC resulted in a 17-fold decrease in J-binding, showing that the pyrimidine base to which the glucose is attached co-determines binding affinity. At least 5 by on both sides of J-base are required for optimal binding of JBP1, although critical contacts are restricted to two bases: major and minor groove contacts with base J and a sequence-independent major groove contact with the base immediately 5' of base J on the same strand (position J-1). Subsequent studies in which the sugar moiety of base J was systematically varied, have suggested a specific role for nucleotide J-1: its non-bridging phosphoryl oxygen hydrogen bonding to the equatorial 2- and 3-hydroxyl groups of the pyranosyl ring of the glucose of base J and locking the glucose in an 'edge-on' conformation perpendicular to the plane of the major DNA groove.

The multimer conjugates provided herein can comprise the JBP polypeptides provided herein or substantially identical polypeptides thereof. As used herein, "substantially identical polypeptide thereof" refers to a polypeptide having a substantially identical structure (e.g. sequence), such as those shown by alignment in FIG. 1, for example, or alignment with another amino acid sequence. In some cases, the amino acid sequences of the JBP polypeptides in a multimer conjugate are the same. In some cases, the amino acid sequences of the JBP polypeptides in the multimer conjugate are different. In some embodiments, the JBP is from a kinetoplastid flagellate organism. Examples of kinetoplastid flagellate organisms include, but are not limited to, *Trypanosoma* spp. organism, *Leishmania* spp. organism, *Crithidia* spp. organism and *Euglena* spp. organism. Examples of *Trypanosoma* spp. organisms include, but are not limited to, *T. brucei* and *T. cruzi*. Examples of *Leishmania* spp. organisms include, but are not limited to, *L. tarentolae, L. aethiopica, L. braziliensis, L. donovani, L. infantum* and *L. major* strain Friedlin. An example of a *Crithidia* spp. Organism is *C. fasciculata*.

In some embodiments, the J-DNA binding protein (JBP) polypeptide (e.g. JBP1) is a native JBP. As used herein, "native JBP" refers to a JBP encoded by a naturally occurring gene or RNA that is present in nature. In some embodiments, the JBP (e.g. JBP1) polypeptide is modified. Modifications can include, for example, modification of the primary amino acid sequence, by deletion, addition, insertion or substitution of one or more amino acids, or modification by chemical modification or post-translational modification. Such modifications include, but are not limited to, pegylation, albumination, glycosylation, farnysylation, carboxylation, hydroxylation, hasylation, carbamylation, sulfation, phosphorylation, and other polypeptide modifications known in the art.

In some embodiments, the JBP polypeptide is a full-length JBP (e.g. JBP1). Examples of full-length JBP1 polypeptides that can be part of the multimer conjugates provided herein are set forth is SEQ ID NOs: 1, and 3-12. In some embodiments, the JBP1 is a fragment of a full length JBP1. In some cases, the fragment comprises the J-DNA binding domain of a JBP. The term "J-DNA binding domain of a JBP" encompasses a polypeptide which can have the structural and/or functional characteristics of the J-DNA binding domain of a JBP. The J-DNA binding domain of a JBP, as used herein, can bind to H-DNA and/or J-DNA, in certain embodiments. The H-DNA and/or J-DNA binding activity can be tested by methods known in the art and described herein below. Examples of JBP1 polypeptide fragments that comprise the J-DNA binding domain of a JBP include, but are not limited to, polypeptide sequences corresponding to amino acids 382 to 561 of SEQ ID NO: 1, amino acids 23-202 of SEQ ID NO: 2, amino acids 382-561 of SEQ ID NO: 3, 382-561 of SEQ ID NO: 4, 382-561 of SEQ ID NO: 5, 382-561 of SEQ ID NO: 6, 382-561 of SEQ ID NO: 7, 382-561 of SEQ ID NO: 8, 406-583 of SEQ ID NO: 9, 400-578 of SEQ ID NO: 10, 400-578 of SEQ ID NO: 11, and 403-581 of SEQ ID NO: 12, or substantially identical polypeptide thereof.

In some embodiments, the multimer conjugates provided herein comprise JBP1 fragments comprising the helix alpha4 peptide. The helix alpha4 peptide of the *T. tarentolae* JBP1, for example, corresponds to amino acids 516 to 525 of SEQ ID NO: 1. The amino acids corresponding helix alpha4 peptides of other JBP1 polypeptides can be identified by alignment, such as the alignment presented in FIG. 1, and are included in the embodiments provided herein. In some embodiments, the multimer conjugates comprise JBP1 fragments comprising the helix alpha1 peptide. The helix alpha1 peptide of the *T. tarentolae* JBP1, for example, corresponds to amino acids 434 to 441 of SEQ ID NO: 1. The amino acids corresponding helix alpha1 peptides of other JBP1 polypeptides can be identified by alignment, such as the alignment presented in FIG. 1, and are included in the embodiments provided herein. In some embodiments, the multimer conjugates comprise JBP1 fragments comprising the loop between helices alpha3 and alpha4. The loop between helices alpha3 and alpha4 of the *T. tarentolae* JBP1, for example, corresponds to amino acids 510 to 515 of SEQ ID NO: 1. The amino acids corresponding the loop between helices alpha3 and alpha4 of other JBP1 polypeptides can be identified by alignment, such as the alignment presented in FIG. 1, and are included in the embodiments provided herein. In some embodiments, the multimer conjugates comprise JBP1 fragments comprising the helix alpha2 peptide and the loop before helix alpha2. The helix alpha2 peptide and the loop before helix alpha2 of the *T. tarentolae* JBP1, for example, corresponds to amino acids 452 to 463 of SEQ ID NO: 1. The amino acids corresponding helix alpha2 peptide and the loop before helix alpha2 of other JBP1 polypeptides can be identified by alignment, such as the alignment presented in FIG. 1, and are included in the embodiments provided herein.

In some embodiments, the JBP or fragment thereof comprises one or more amino acids that are fully conserved among JBP1 proteins from two or more kinetoplastid flagellates. Examples of such conserved amino acids are chosen from amino acids at positions 387, 388, 389, 390, 391, 399, 402, 411, 423, 427, 430, 431, 433, 434, 438, 446, 448, 451, 453, 455, 457, 459, 560, 462, 463, 464, 465, 466, 467, 469, 471, 472, 474, 476, 487, 491, 492, 496, 498, 499, 502, 503, 509, 518, 519, 520, 521, 522, 523, 524, 525, 528, 529, 530, 531, 532, 533, 535, 536, 537, 538, 540, 541, 544, 545, 548, 552, 553, 555, 556, 557, 571, 572, 574, 577, 578, 579, 580, 582, 583 and 593 of *L. tarentolae* (SEQ ID NO: 1), or corresponding amino acids thereof. As used herein, "corresponding amino acids thereof" refers to amino acids having the same or similar structure in the same position, such as those shown by alignment in FIG. 1, for example, or alignment with another amino acid sequence, and are included in the embodiments provided herein.

A JBP or fragment thereof (e.g. a J-DNA binding domain or fragment thereof) useful in accordance with the multimer conjugates provided herein can, for example, be identified by using sequence comparisons and/or alignments by employing means and methods known in the art, such as those described herein, and comparing and/or aligning known JBPs to/with a sequence suspected to be a JBP.

For example, when a position in both of the two compared sequences is occupied by the same base or amino acid monomer subunit (for instance, if a position in each of the two DNA molecules is occupied by adenine, or a position in each of two polypeptides is occupied by a lysine), then the respective molecules are identical at that position. The percentage identity between two sequences is a function of the number of matching or identical positions shared by the two sequences divided by the number of positions compared×100. For instance, if 6 of 10 of the positions in two sequences are matched or are identical, then the two sequences are 60% identical. Generally, a comparison is made when two sequences are aligned to give maximum homology and/or identity. Such alignment can be provided using, for instance, the method of Needleman, J. Mol. Biol. 48 (1970): 443-453, implemented conveniently by computer programs such as the Align program (DNAstar, Inc.). Homologous sequences share identical or similar amino acid residues, where similar residues are conservative substitutions for, or "allowed point mutations" of, corresponding amino acid residues in an aligned reference sequence. In this regard, a "conservative substitution" of a residue in a reference sequence are those substitutions that are physically or functionally similar to the corresponding reference residues, e.g., that have a similar size, shape, electric charge, chemical properties, including the ability to form covalent or hydrogen bonds, or the like. Conservative substitutions are those fulfilling the criteria defined for an "accepted point mutation" in Dayhoff et al., 5: Atlas of Protein Sequence and Structure, 5: Suppl. 3, chapter 22: 354-352, Nat. Biomed. Res. Foundation, Washington, D.C. (1978).

In some embodiments, the J-DNA binding domain or fragment thereof of the JBPs provided herein shares 50%, 60%, 70%, 75%, 80%, 85%, 90%, 91%, 92%, 93%, 94%, 95%, 96%, 97%, 98%, 99% or more identity at the amino acid level to one or more of the JBPs shown in FIG. 1 and is able to bind H-DNA and/or J-DNA. Means and methods for determining the identity of sequences, for example, amino acid sequences, is described elsewhere herein.

The binding of the multimer conjugates provided herein to H-DNA and/or J-DNA can be assayed by any method known in the art including but not limited to, competition assays (e.g. gel retardation competition assays) and fluorescence anisotropy polarization (FP) assays (see e.g. Sabatini et al., (2002) J. Biol. Chem. 277:958-966; Grover et al., (2007) Angew Chem. Int. Ed. Engl. 46:2839-2843) or any method known in the art for assaying protein-nucleic acid binding including, gel shift assays (e.g. electromobility shift assays (EMSA), band shift assays) or any commercially available assay or kit. Gel shift assays, for example, are based on the observation that complexes of protein and DNA migrate through a nondenaturing polyacrylamide gel more slowly than free DNA fragments or double-stranded oligonucleotides. The gel shift assay is carried out by first incubating a protein(s) (such as nuclear or cell extract) with a 32P end-labeled DNA fragment containing the putative protein binding site. The reaction products are then analyzed on a nondenaturing polyacrylamide gel.x The specificity of the DNA-binding protein for the putative binding site is established by competition experiments using, for example, DNA fragments or oligonucleotides containing a binding site for the protein of interest or other unrelated DNA sequences.

Nucleic Acid

Provided herein are nucleic acid molecules which comprise a nucleotide sequence that encodes a multivalent conjugate, a multivalent conjugate subunit, or the polypeptide portion of a multivalent conjugate or conjugate subunit. The term "nucleic acid molecule" when used herein encompasses any nucleic acid molecule having a nucleotide sequence of bases comprising purine- and pyrimidine bases which are comprised by the nucleic acid molecule, whereby the bases represent the primary structure of a nucleic acid molecule. As used herein, "nucleic acid" also refers to the nucleic acid with which the multimer conjugates provided herein specifically interact, such as, for example, H-DNA and/or J-DNA as described herein. Nucleic acid sequences include DNA, cDNA, genomic DNA, RNA, synthetic forms, for example, PNA, and mixed polymers, both sense and antisense strands, or may contain non-natural or derivatized nucleotide bases, as will be readily appreciated by those skilled in the art. The polynucleotides can be composed of any polyribonucleotide or polydeoxyribonucleotide, which may be unmodified RNA or DNA or modified RNA or DNA. A polynucleotide can be composed of single- and double-stranded DNA, DNA that is a mixture of single- and double-stranded regions, single- and double-stranded RNA, and RNA that is mixture of single- and double-stranded regions, hybrid molecules comprising DNA and RNA that may be single-stranded or, more typically, double-stranded or a mixture of single- and double-stranded regions. In addition, polynucleotide can be composed of triple-stranded regions comprising RNA or DNA or both RNA and DNA. Polynucleotide may also contain one or more modified bases or DNA or RNA backbones modified for stability or for other reasons. "Modified" bases include, for example, tritylated bases and unusual bases such as inosine. A variety of modifications can be made to DNA and RNA; thus, the term "nucleic acid molecules" embraces chemically, enzymatically, or metabolically modified forms.

In some embodiments, the nucleic acid has a nucleotide sequence encoding a variant of a polypeptide encoded by a polynucleotide provided herein, where in the variant comprises one or more amino acid residues are substituted compared to the polypeptide, and the variant is capable of binding H-DNA and/or J-DNA. Also provided are nucleic acid sequences each having a nucleotide sequence which hybridizes with a nucleic acid sequence provided herein and which is at least 65% identical to the nucleotide sequence of nucleic acid molecule provided herein and which encodes a polypeptide capable of binding H-DNA and/or J-DNA.

In some embodiments, the nucleic acid sequences encode a polypeptide which is at least 65%, 70%, 75%, 80%, 85%, 90%, or 99% identified to one of the polypeptides provided herein (e.g. the polypeptide set forth in SEQ ID NO: 1 or a fragment thereof). The term "hybridizes" as used herein relates to hybridizations under stringent conditions. The term "hybridizing sequences" refers to sequences which display a sequence identity of at least 65%, at least 70%, at least 80%, at least 90%, at least 95%, or at least 97, 98% or 99% identity with a nucleic acid sequence as described above encoding a polypeptide which is able to bind to H-DNA and/or J-DNA.

Such hybridization conditions may be established according to conventional protocols described, for example, in Sambrook, Russell "Molecular Cloning, A Laboratory Manual", Cold Spring Harbor Laboratory, N.Y. (2001); Ausubel, "Current Protocols in Molecular Biology", Green Publishing Associates and Wiley Interscience, N.Y. (1989), or Higgins and Hames (Eds.) "Nucleic acid hybridization, a practical approach" IRL Press Oxford, Washington D.C., (1985). The setting of conditions is well within the skill of the artisan and can be determined according to protocols described in the art. Thus, the detection of specifically hybridizing sequences will typically require stringent hybridization and washing conditions such as 0.1×SSC, 0.1% SDS at 65° C., for example. Non-stringent hybridization conditions for the detection of homologous or not exactly complementary sequences may be set at 6×SSC, 1% SDS at 65° C., for example. The length of the probe and the composition of the nucleic acid to be determined constitute further parameters of the hybridization conditions. Note that variations in the above conditions may be accomplished through the inclusion and/or substitution of alternate blocking reagents used to suppress background in hybridization experiments. Typical blocking reagents include Denhardt's reagent, BLOTTO, heparin, denatured salmon sperm DNA, and commercially available proprietary formulations. The inclusion of specific blocking reagents may require modification of the hybridization conditions described above, due to problems with compatibility. Hybridizing nucleic acid molecules also comprise fragments of the above described molecules. Such fragments may represent nucleic acid sequences as described herein. Furthermore, nucleic acid molecules which hybridize with any of the aforementioned nucleic acid molecules also include complementary fragments, derivatives and allelic variants of these molecules. Additionally, a hybridization complex refers to a complex between two nucleic acid sequences by virtue of the formation of hydrogen bonds between complementary G and C bases and between complementary A and T bases; these hydrogen bonds may be further stabilized by base stacking interactions. The two complementary nucleic acid sequences hydrogen bond in an antiparallel configuration. A hybridization complex may be formed in solution (e.g., Cot or Rot analysis) or between one nucleic acid sequence present in solution and another nucleic acid sequence immobilized on a solid support (e.g., membranes, filters, chips, pins or glass slides to which, e.g., cells have been fixed). The terms complementary or complementarity refer to the natural binding of polynucleotides under permissive salt and temperature conditions by base-pairing. For example, the sequence "A-G-T" binds to the complementary sequence "T-C-A". Complementarity between two single-stranded molecules may be "partial", in which only some of the nucleic acids bind, or it may be complete when total complementarity exists between single-stranded molecules. The degree of complementartity between nucleic acid strands has significant effects on the efficiency and strength of hybridization between nucleic acid strands. This is of particular importance in amplification reactions, which depend upon binding between nucleic acids strands.

As used herein, the term "identical" or "percent identity" in the context of two or more nucleic acid or amino acid sequences, refers to two or more sequences or subsequences that are the same, or that have a specified percentage of amino acid residues or nucleotides that are the same (e.g., at least 65% identity, at least 70-95% identity, at least 95%, 96%, 97%, 98% or 99% identity), when compared and aligned for maximum correspondence over a window of comparison, or over a designated region as measured using a sequence comparison algorithm as known in the art, or by manual alignment and visual inspection. Sequences having, for example, 65% to 95% or greater sequence identity are considered to be substantially identical. Such a definition also applies to the complement of a test sequence. Those having skill in the art will know how to determine percent identity between/among sequences using, for example, algorithms such as those based on CLUSTALW computer program (Thompson Nucl. Acids Res. 2 (1994), 4673-4680) or FASTDB (Brutlag Comp. App. Biosci. 6 (1990), 237-245), as is known in the art.

Although the FASTDB algorithm typically does not consider internal non-matching deletions or additions in sequences, i.e., gaps, in its calculation, this can be corrected manually to avoid an overestimation of the % identity. CLUSTALW, however, does take sequence gaps into account in its identity calculations. Also available to those having skill in this art are the BLAST and BLAST 2.0 algorithms (Altschul Nucl. Acids Res. 25 (1977), 3389-3402). The BLASTN program for nucleic acid sequences uses as defaults a word length (W) of 11, an expectation (E) of 10, M=5, N=4, and a comparison of both strands. For amino acid sequences, the BLASTP program uses as defaults a wordlength (W) of 3, and an expectation (E) of 10. The BLOSUM62 scoring matrix (Henikoff Proc. Natl. Acad. Sd., USA, 89, (1989), 10915) uses alignments (B) of 50, expectation (E) of 10, M=5, N=4, and a comparison of both strands. For example, BLAST2.0, which stands for Basic Local Alignment Search Tool (Altschul, Nucl. Acids Res. 25 (1997), 3389-3402; Altschul, J. Mol. Evol. 36 (1993), 290-300; Altschul, J. Mol. Biol. 215 (1990), 403-410), can be used to search for local sequence alignments. BLAST produces alignments of both nucleotide and amino acid sequences to determine sequence similarity. Because of the local nature of the alignments, BLAST is especially useful in determining exact matches or in identifying similar sequences. The fundamental unit of BLAST algorithm output is the High-scoring Segment Pair (HSP). An HSP consists of two sequence fragments of arbitrary but equal lengths whose alignment is locally maximal and for which the alignment score meets or exceeds a threshold or cutoff score set by the user. The BLAST approach is to look for HSPs between a query sequence and a database sequence, to evaluate the statistical significance of any matches found, and to report only those matches which satisfy the user-selected threshold of significance. The parameter E establishes the statistically significant threshold for reporting database sequence matches. E is interpreted as the upper bound of the expected frequency of chance occurrence of an HSP (or set of HSPs) within the context of the entire database search. Any database sequence whose match satisfies E is reported in the program output.

Analogous computer techniques using BLAST (Altschul (1997), loc. cit.; Altschul (1993), loc. cit.; Altschul (1990), loc. cit.) are used to search for identical or related molecules in nucleotide databases such as GenBank or EMBL. This analysis is much faster than multiple membrane-based hybridizations. In addition, the sensitivity of the computer search can be modified to determine whether any particular match is categorized as exact or similar. The basis of the search is the product score which is defined as:

$$\frac{\% \text{ sequence identity} \times \% \text{ maximum } BLAST \text{ score}}{100}$$

It takes into account both the degree of similarity between two sequences and the length of the sequence match. For example, with a product score of 40, the match will be exact within a 1-2% error; and at 70, the match will be exact. Similar molecules are usually identified by selecting those which show product scores between 15 and 40, although lower scores may identify related molecules.

Moreover, provided herein are nucleic acid molecules the sequence of which is degenerate in comparison with the sequence of an above-described nucleic acid molecule. When used herein the term "being degenerate as a result of the genetic code" means that due to the redundancy of the genetic code different nucleotide sequences code for the same amino acid. Also provided herein are the complementary strand to the aforementioned and below mentioned nucleic acid molecules if they may be in a single-stranded form.

Polypeptides

The term "polypeptide" when used herein means a peptide, a protein, or a polypeptide, which are used interchangeably and which encompasses amino acid chains of a given length, wherein the amino acid residues are linked by covalent peptide bonds. Peptidomimetics of such proteins/polypeptides wherein amino acid(s) and/or peptide bond(s) have been replaced by functional analogs are also included herein as well as those other than the 20 gene-encoded amino acids, such as selenocysteine. Peptides, oligopeptides and proteins may be termed polypeptides. As mentioned the terms polypeptide and protein are often used interchangeably herein. The term polypeptide also refers to, and does not exclude, modifications of the polypeptide. Modifications include glycosylation, acetylation, acylation, phosphorylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cysteine, formation of pyroglutamate, formulation, gamma-carboxylation, glycosylation, GPI anchor formation, hydroxylation, iodination, methylation, myristoylation, oxidation, pegylation, proteolytic processing, phosphorylation, prenylation, racemization, selenoylation, sulfation, transfer-RNA mediated addition of amino acids to proteins such as arginylation, and ubiquitination (see, e.g., PROTEINS—STRUCTURE AND MOLECULAR PROPERTIES, 2nd Ed., T. E. Creighton, W.H. Freeman and Company, New York (1993); POST-TRANSLATIONAL COVALENT MODIFICATION OF PROTEINS, B. C. Johnson, Ed., Academic Press, New York (1983), pgs. 1-12; Seifter, Meth. Enzymol. 182 (1990); 626-646, Rattan, Ann. NY Acad. Sci. 663 (1992); 48-62).

In some embodiments, the multimer conjugates provided herein are polypeptides. In some embodiments, the multimer conjugates provided herein are a combination of polypeptide and non-polypeptide. In some embodiments, the multimer conjugates comprise one or more variant polypeptides.

As used herein, a "variant" of a polypeptide provided herein encompasses a polypeptide wherein one or more amino acid residues are substituted, and sometimes conservatively substituted, compared to a polypeptide provided herein and wherein the variant is able to bind to H-DNA and/or J-DNA. Such variants include deletions, insertions, inversions, repeats, and substitutions selected according to general rules known in the art so as have no effect on the activity of the polypeptide provided herein. For example, guidance concerning how to make phenotypically silent amino acid substitutions is provided in Bowie, Science 247: (1990) 1306-1310, wherein the authors indicate that there are two main strategies for studying the tolerance of an amino acid sequence to change. The first strategy exploits the tolerance of amino acid substitutions by natural selection during the process of evolution. By comparing amino acid sequences in different species, conserved amino acids can be identified. These conserved amino acids are likely important for protein function. In contrast, the amino acid positions where substitutions have been tolerated by natural selection indicates that these positions are not critical for protein function. Thus, positions tolerating amino acid substitution could be modified while still maintaining biological activity of the protein. The second strategy uses genetic engineering to introduce amino acid changes at specific positions of a cloned gene to identify regions critical for protein function. For example, site directed mutagenesis or alanine-scanning mutagenesis (introduction of single alanine mutations at every residue in the molecule) can be used. (Cunningham and Wells, Science 244: (1989) 1081-1085.) The resulting mutant molecules can then be tested for biological activity.

These two strategies have revealed that proteins can be tolerant of amino acid substitutions. The amino acid changes that are likely to be permissive at certain amino acid positions in the protein are also indicated. For example, the most buried (within the tertiary structure of the protein) amino acid residues require nonpolar side chains, whereas few features of surface side chains are generally conserved.

In some embodiments, the polypeptides provided herein have a lower degree of identity but have sufficient similarity so as to perform one or more of the functions performed by another polypeptide provided herein. Similarity is determined by conserved amino acid substitution. Such substitutions are those that substitute a given amino acid in a polypeptide by another amino acid of like characteristics (e.g., chemical properties). According to Cunningham et al. above, such conservative substitutions are likely to be phenotypically silent. Additional guidance concerning which amino acid changes are likely to be phenotypically silent are found in Bowie, Science 247: (1990) 1306-1310.

Tolerated conservative amino acid substitutions can involve replacement of the aliphatic or hydrophobic amino acids Ala, Val, Leu and Me; replacement of the hydroxyl residues Ser and Thr; replacement of the acidic residues Asp and Glu; replacement of the amide residues Asn and Gln, replacement of the basic residues Lys, Arg, and His; replacement of the aromatic residues Phe, Tyr, and Trp, and replacement of the small-sized amino acids Ala, Ser, Thr, Met, and Gly.

In addition, the conservative substitutions provided below are also contemplated.

Alanine (A): D-Ala, Gly, beta-Ala, L-Cys, D-Cys
Arginine (R): D-Arg, Lys, D-Lys, homo-Arg, D-homo-Arg, Met, Me, D-Met, D-Ile, Orn, D-Orn
Asparagine (N): D-Asn, Asp, D-Asp, Glu 1 D-Glu, Gln, D-Gln
Aspartic Acid (D): D-Asp, D-Asn, Asn, Glu, D-Glu, Gln, D-Gln
Cysteine (C): D-Cys, S-Me-Cys, Met, D-Met, Thr, D-Thr
Glutamine (Q): D-Gln, Asn, D-Asn, Glu, D-Glu, Asp, D-As
Glutamic Acid (E): D-Glu, D-Asp, Asp, Asn, D-Asn, Gln, D-Gln
Glycine (G): Ala, D-Ala, Pro, D-Pro, β-Ala, Acp Isoleucine D-Ile, Val, D-Val, Leu, D-Leu, Met, D-Met
Leucine (L): D-Leu, Val, D-Val, Met, D-Met
Lysine (K): D-Lys, Arg, D-Arg, homo-Arg, D-homo-Arg, Met, D-Met, lie, D-Ile, Orn, D-Orn
Methionine (M): D-Met, S-Me-Cys, He, D-Ile, Leu, D-Leu, Val, D-Val
Phenylalanine (F): D-Phe, Tyr, D-Thr, L-Dopa, His, D-His, Trp, D-Trp, Trans-3,4, or 5-phenylproline, cis-3,4, or 5-phenylproline
Proline (P): D-Pro, L-1-thioazolidine-4-carboxylic acid, D- or L-1-oxazolidine-4-carboxylic acid
Serine (S): D-Ser, Thr, D-Thr, allo-Thr, Met, D-Met, Met (O), D-Met(O), L-Cys, D-Cys
Threonine (T): D-Thr, Ser, D-Ser, allo-Thr, Met, D-Met, Met(O), D-Met(O), Val, D-Val
Tyrosine (Y): D-Tyr, Phe, D-Phe, L-Dopa, His, D-His
Valine (V): D-Val, Leu, D-Leu, lie, D-Ile, Met, D-Met Aside from the uses described above, such amino acid substitutions may also increase protein or peptide stability. The multimer conjugates provided herein encompass amino acid substitutions that contain, for example, one or more non-peptide bonds (which replace the peptide bonds) in the protein or peptide sequence. Also included are substitutions that include amino acid residues other than naturally occurring L-amino acids, e.g., D-amino acids or non-naturally occurring or synthetic amino acids, e.g., beta or gamma amino acids.

Both identity and similarity can be readily calculated by reference to the following publications: Computational Molecular Biology, Lesk, A. M., ed., Oxford University Press, New York, 1988; Biocomputing: Infolivaties and Genome Projects, Smith, D M., ed., Academic Press, New York, 1993; Informafies Computer Analysis of Sequence Data, Part 1, Griffin, A. M., and Griffin, H. G., eds., Humana Press, New Jersey, 1994; Sequence Analysis in Molecular Biology, von Heinje, G., Academic Press, 1987; and Sequence Analysis Primer, Gribskov, M. and Devereux, eds., M Stockton Press, New York, 1991.

Linkers, Tags, Labels and Detectable Molecules

In some embodiments of the multimer conjugates provided herein, the conjugate further comprises a linker polypeptide. In some cases, the linker polypeptide is provided in the polynucleotide encoding the conjugate between the nucleotide sequence encoding the JBP and a scaffold such that it results in a fusion between the JBP, linker polypeptide and scaffold. A "fusion" refers to a co-linear linkage of two or more proteins or fragments thereof via their individual peptide backbones through genetic expression of a nucleic acid molecule encoding those proteins. Thus, fusion proteins include a JBP, or DNA binding domain of a JBP or fragment thereof, wherein the fragment has the activity of binding H-DNA and/or J-DNA, covalently linked to the linker polypeptide which is itself covalently linked to a scaffold as is described herein. In some cases, a JBP-linker fusion protein is generated and subsequently conjugated to the scaffold, such as, for example, in multimer conjugates where the scaffold is a non-protein scaffold.

The polypeptide linker, in some embodiments, is a flexible linker. In some cases, the linker comprises a plurality of hydrophilic, peptide-bonded amino acids and connects the C-terminal end of the JBP and the N-terminal end of a scaffold, the C-terminal end of the scaffold and the N-terminal end of the JBP, or the N-terminal or C-terminal end of the JBP to any region of the scaffold. Optionally, the linker contains a protease cleavage site proximal to the scaffold which allows the cutting off of the scaffold, if desired. Protease cleavage sites are, for example, a thrombin cleavage site.

In some embodiments, the polypeptide linker comprises a plurality of glycine, alanine, aspartate, glutamate, proline, isoleucine and/or arginine residues. In some cases, the polypeptide linker comprises a plurality of consecutive copies of an amino acid sequence. Typically, the polypeptide linker comprises 1 to 20, e.g. 1 to 19, 1 to 18, 1 to 17, 1 to 16 or 1 to 15, amino acids although polypeptide linkers of more than 20 amino acids are also contemplated. For example, the polypeptide linker can comprise 1 to 14 amino acid residues. In some embodiments, the polypeptide linker comprises 14 amino acids.

The multimer conjugates, in some embodiments, optionally comprise a tag at the N- and/or C-terminus. A "tag" is an amino acid sequence which is homologous or heterologous to an amino acid sequence to which it is fused. The tag can facilitate purification of a protein or can facilitate detection of the protein to which it is fused. In some cases, the tag is selected from the group consisting of a HA-tag, myc6-tag, flag-tag, strep-tag, strepII-tag, TAP-tag, HAT-tag, chitin binding domain (CBD), maltose-binding protein, immunoglobulin A (IgA), His-6-tag (SEQ ID NO: 13), glutathione-S-transferase (GST) tag, intein and streptavidin binding protein (SBP) tag.

The multimer conjugates, in some embodiments, optionally comprise one or more detectable labels and/or signal generating molecules. Examples of labels include, without limitation, monoclonal antibodies, polyclonal antibodies, proteins, or other polymers (e.g., affinity matrices), carbohydrates or lipids, which often are attached, or are capable of being attached, to a detectable label. Detection can proceed by any known method, such as immunoblotting, Western blot analysis, tracking of radioactive or bioluminescent markers, capillary electrophoresis, or another other methods that tracks a molecule based upon size, charge and/or affinity. A detectable moiety can be any material having a detectable physical or chemical property. Such detectable labels have been well-developed in the field of gels, columns, solid substrates cell cytometry and immunoassays and, in general, any label useful in such methods can be applied to the conjugates provided herein. Thus, a label is any composition detectable by spectroscopic, photochemical, biochemical, immunochemical, electrical, optical or chemical methods. Useful labels include, without limitation, magnetic beads (e.g. DYNABEADS), fluorescent dyes (e.g., fluorescein isothiocyanate, Texas red, rhodamine, and the like), radiolabels (e.g., 3H, 125I, 35S, 14C, or 32P), enzymes (e.g., LacZ, CAT, horse radish peroxidase, alkaline phosphatase and others, commonly used as detectable enzymes, either as marker gene products or in an ELISA), nucleic acid intercalators (e.g., ethidium bromide) and calorimetric labels such as colloidal gold or colored glass or plastic (e.g. polystyrene, polypropylene, latex, and the like) beads.

A label can be coupled directly or indirectly to a desired component of an assay or separation method according to methods known in the art. A wide variety of labels can be used, with the choice of label depending on the sensitivity required, ease of conjugation of the compound, stability requirements, available instrumentation, and disposal provisions. Non-radioactive labels often are attached by indirect attachments. A ligand molecule (e.g., biotin) sometimes is covalently bound to a polymer, in certain embodiments. The ligand then binds to an anti-ligand (e.g., streptavidin) molecule which is either inherently detectable or covalently bound to a signal system, such as a detectable enzyme, a fluorescent compound, or a chemiluminescent compound. A number of ligand/anti-ligand pairs can be used. Where a ligand has a natural anti-ligand, for example, biotin, thyroxine, and cortisol, it can be used in conjunction with a labeled, anti-ligand, in some embodiments. A haptenic or antigenic compound can be used in combination with an antibody in certain embodiments.

A label can be conjugated directly to a signal generating molecule (e.g., by conjugation with an enzyme or fluorophore) in some embodiments. An enzyme of interest sometimes is utilized as a label, and can be a hydrolase (e.g., phosphatase, esterase, glycosidase), or oxidoreductases (e.g., peroxidases), in certain embodiments. Fluorescent compounds include fluorescein and its derivatives, rhodamine and its derivatives, dansyl, umbelliferone, and the like. Chemiluminescent compounds include luciferin, and 2,3-dihydrophthalazinediones, e.g., luminol. For a review of various labeling or signal producing systems which are used, see, U.S. Pat. No. 4,391,904. In some embodiments, the signal generating molecule is conjugated directly to a multimer conjugate provided herein.

Vectors

In some embodiments, a nucleic acid molecule provided herein is part of a vector. Such a vector may be, e.g., a plasmid, cosmid, virus, bacteriophage or another vector used e.g. conventionally in genetic engineering, and may comprise further genes such as marker genes which allow for the selection and/or replication of the vector in a suitable host cell and under suitable conditions. In some embodiments, the vector is an expression vector, in which the nucleic acid molecule is operatively linked and to expression control sequence(s) allowing expression in prokaryotic or eukaryotic host cells as described herein. The term "operatively linked", as used in this context, refers to a linkage between one or more expression control sequences and the coding region in the polynucleotide to be expressed in such a way that expression is achieved under conditions compatible with the expression control sequence.

The nucleic acid molecules provided herein may thus be inserted into several commercially available vectors. Nonlimiting examples include plasmid vectors compatible with mammalian cells, such as pUC, pBluescript (Stratagene), pET (Novagen), pREP (Invitrogen), pCRTopo (Invitrogen), pcDNA3 (Invitrogen), pCEP4 (Invitrogen), pMC1 neo (Stratagene), pXT1 (Stratagene), pSG5 (Stratagene), EBO-pSV2neo, pBPV-1, pdBPVMMTneo, pRSVgpt, pRSVneo, pSV2-dhfr, pUCTag, pIZD35, pLXIN and pSIR (Clontech) and pIRES-EGFP (Clontech). In some embodiments, the nucleic acid molecules are inserted into the vector Signal pIG plus (Ingenius, R&D Systems). Baculovirus vectors such as pBlueBac, BacPacz Baculovirus Expression System (CLONTECH), and MAXBAC Baculovirus Expression System, insect cells and protocols (Invitrogen) are available commercially and may also be used to produce high yields of biologically active protein, (see also, Miller (1993), Curr. Op. Genet. Dev., 3, 9; O'Reilly, Baculovirus Expression Vectors: A Laboratory Manual, p. 127). In addition, prokaryotic vectors such as pcDNA2; and yeast vectors such as pYes2 are non-limiting examples of other vectors suitable for use herein.

Other expression vector examples are those for expressing proteins in *Drosophila* cells which are well known in the art, such as the DES®-series of Invitrogen. In some embodiments, the *Drosophila* cell expression vector is pMT/BiP/V5-His B (Invitrogen). The pMT/BiP/V5-His vector offers the following additional features. It has a small size (3.6 kb) to improve DNA yields and increase subcloning efficiency, it has a C-terminal V5 epitope tag for rapid detection with Anti-V5 Antibody and it has a C-terminal 6×His tag (SEQ ID NO: 13) for simple purification of recombinant fusion proteins using nickel-chelating resin.

For vector modification techniques, see Sambrook and Russel (2001), loc. cit. Vectors can contain one or more replication and inheritance systems for cloning or expression, one or more markers for selection in the host, e.g., antibiotic resistance, and one or more expression cassettes.

The coding sequences inserted in the vector can be synthesized by standard methods, isolated from natural sources, or prepared as hybrids. Ligation of the coding sequences to transcriptional regulatory elements (e.g., promoters, enhancers, and/or insulators) and/or to other amino acid encoding sequences can be carried out using established methods.

Furthermore, the vectors may, in addition to the nucleic acid sequences, comprise expression control elements, allowing proper expression of the coding regions in suitable hosts. Such control elements are known to the artisan and may include a promoter, translation initiation codon, translation and insertion site or internal ribosomal entry sites (IRES) (Owens, Proc. Natl. Acad. Sci. USA 98 (2001), 1471-1476) for introducing an insert into the vector. In some embodiments, the nucleic acid molecule is operatively linked to an expression control sequences allowing expression in eukaryotic or prokaryotic cells.

Control elements ensuring expression in eukaryotic and prokaryotic cells are well known to those skilled in the art. As mentioned above, they typically comprise regulatory sequences ensuring initiation of transcription and optionally poly-A signals ensuring termination of transcription and stabilization of the transcript. Additional regulatory elements may include transcriptional as well as translational enhancers, and/or naturally-associated or heterologous promoter regions. Possible regulatory elements permitting expression in for example mammalian host cells comprise the CMV-HSV thymidine kinase promoter, SV40, RSV-promoter (Rous sarcoma virus), human elongation factor 1α-promoter, CMV enhancer, CaM-kinase promoter or SV40-enhancer.

For the expression in prokaryotic cells, a multitude of promoters including, for example, the tac-lac-promoter, the lacUV5 or the trp promoter, has been described. Beside elements which are responsible for the initiation of transcription such regulatory elements may also comprise transcription termination signals, such as SV40-poly-A site or the tk-poly-A site, downstream of the polynucleotide. In this context, suitable expression vectors are known in the art such as Okayama-Berg cDNA expression vector pcDV1 (Pharmacia), pRc/CMV, pcDNAI, pcDNA3 (In-Vitrogene, as used, inter alia in the appended examples), pSPORTI (GIBCO BRL) or pGEMHE (Promega), or prokaryotic expression vectors, such as lambda gt11.

An expression vector provided herein is at least capable of directing the replication, and often the expression, of the nucleic acids and proteins provided herein. Suitable origins of replication include, for example, the Col E1, the SV40 viral and the M 13 origins of replication. Suitable promoters include, for example, the cytomegalovirus (CMV) promoter, the lacZ promoter, the gal 10 promoter and the *Autographa californica* multiple nuclear polyhidrosis virus (AcMNPV) polyhedral promoter. Suitable termination sequences include, for example, the bovine growth hormone, SV40, lacZ and AcMNPV polyhedral polyadenylation signals. Examples of selectable markers include neomycin, ampicillin, and hygromycin resistance and the like. Specifically-designed vectors allow the shuttling of DNA between different host cells, such as bacteria-yeast, or bacteria-animal cells, or bacteria-fungal cells, or bacteria invertebrate cells.

Beside the nucleic acid molecules provided herein, the vector may further comprise nucleic acid sequences encoding for secretion signals. A secretion signal that can be used in herein when the polypeptide is expressed in *Drosophila* cells, e.g. *Drosophila* S2 cells, is the *Drosophila* BiP secretion signal well known in the art. Other secretion signal sequences are well known to the person skilled in the art. Furthermore, depending on the expression system used, leader sequences capable of directing the expressed polypeptide to a cellular compartment may be added to the coding sequence of the nucleic acid molecules provided herein and are well known in the art. The leader sequence(s) is (are) assembled in appropriate phase with translation, initiation and termination sequences, and sometimes, a leader sequence capable of directing secretion of translated protein, or a part thereof, into, inter alia, the extracellular membrane. Optionally, the heterologous sequence can encode a fusion protein including a C- or N-terminal identification peptide imparting desired characteristics, e.g., stabilization or simplified purification of expressed recombinant product. Once the vector has been incorporated into the appropriate host, the host is maintained under conditions suitable for high level expression of the nucleotide sequences, and, as desired, the collection and purification of the proteins, antigenic fragments or fusion proteins may follow. The vector can also comprise regulatory regions from pathogenic organisms.

Furthermore, the vector may also be, besides an expression vector, a gene transfer and/or gene targeting vector. Gene therapy, which is based on introducing therapeutic genes (for example for vaccination) into cells by ex-vivo or in-vivo techniques is an example application of gene transfer. Suitable vectors, vector systems and methods for in-vitro or in-vivo gene therapy are described in the literature and are known to the person skilled in the art; see, e.g., Giordano, Nature Medicine 2 (1996), 534-539; Schaper, Circ. Res. 79 (1996), 911-919; Anderson, Science 256 (1992), 808-813, Isner, Lancet 348 (1996), 370-374; Muhlhauser, Circ. Res. 77 (1995), 1077-1086; Wang, Nature Medicine 2 (1996), 714-716; WO 94/29469; WO 97/00957; Schaper, Current Opinion in Biotechnology 7 (1996), 635-640 or Verma, Nature 389 (1997), 239-242 and references cited therein.

The nucleic acid molecules provided herein and vectors as described herein above may be designed for direct introduction or for introduction via liposomes, or viral vectors (e.g. adenoviral, retroviral) into the cell. Additionally, baculoviral systems or systems based on vaccinia virus or Semliki Forest Virus can be used as eukaryotic expression system for the nucleic acid molecules provided herein. In addition to recombinant production, fragments of the protein, the fusion protein or antigenic fragments may be produced by direct peptide synthesis using solid-phase techniques (Stewart et al. (1969) Solid Phase Peptide Synthesis; Freeman Co, San Francisco; Merrifield, J. Am. Chem. Soc. 85 (1963), 2149-2154). In vitro protein synthesis may be performed using manual techniques or by automation. Automated synthesis may be achieved, for example, using Applied Biosystems 431A Peptide Synthesizer (Perkin Elmer, Foster City Calif.) in accordance with the instructions provided by the manufacturer. Various fragments may be chemically synthesized separately and combined using chemical methods to produce the full length molecule.

Cells

Provided herein are host cells genetically engineered with nucleic acid molecule provided herein or a vector provided herein. Such host cell may be produced by introducing the vector or nucleotide sequence into a host cell which upon its presence in the cell mediates the expression of a protein encoded by the nucleotide sequence or comprising a nucleotide sequence or a vector provided herein wherein the nucleotide sequence and/or the encoded polypeptide is foreign to the host cell.

By "foreign" it is meant that the nucleotide sequence and/or the encoded polypeptide is either heterologous with respect to the host, which means derived from a cell or organism with a different genomic background, or is homologous with respect to the host but located in a different genomic environment than the naturally occurring counterpart of the nucleotide sequence. This means that, if the nucleotide sequence is homologous with respect to the host, it is not located in its natural location in the genome of the host, and is often surrounded by different genes. In this case the nucleotide sequence may be either under the control of its own promoter or under the control of a heterologous promoter. The location of the introduced nucleic acid molecule or the vector can be determined by the skilled person by using methods well-known to the person skilled in the art, e.g., Southern Blotting. The vector or nucleotide sequence which is present in the host may either be integrated into the genome of the host or it may be maintained in some form extrachromosomally. In this respect, it is also to be understood that the nucleotide sequence can be used to restore or create a mutant gene via homologous recombination.

The host may be any prokaryotic or eukaryotic cell. Suitable prokaryotic/bacterial cells are those generally used for cloning like *E. coli, Salmonella typhimurium, Serratia marcescens* or *Bacillus subtilis*. The eukaryotic host may be a mammalian cell, an amphibian cell, a fish cell, an insect cell, a fungal cell, a plant cell or a bacterial cell (e.g., *E coli* strains HB101, DH5a, XL1 Blue, Y1090 and JM101). In some embodiments, eukaryotic recombinant host cells are used. Examples of eukaryotic host cells include, but are not limited to, yeast, e.g., *Saccharomyces cerevisiae, Schizosaccharomyces pombe, Kluyveromyces lactis* or *Pichia pastoris* cells, cell lines of human, bovine, porcine, monkey, and rodent origin, as well as insect cells, including but not limited to, *Spodoptera frugiperda* insect cells and zebra fish cells.

In some embodiments, *Drosophila* cells are used. In some embodiments, the *Drosophila* cells are *Drosophila* S2 (ATCC CRL-1963) which can be used for heterologous protein expression in *Drosophila* expression systems, for example, the *Drosophila* Expression System (DES®). The S2 cell line was derived from a primary culture of late stage (20-24 hours old) *Drosophila melanogaster* embryos. This versatile cell line grows rapidly at room temperature without CO2 and is easily adapted to suspension culture.

Mammalian species-derived cell lines suitable for use and commercially available include, but are not limited to, L cells, CV-1 cells, COS-1 cells (ATCC CRL 1650), COS-7 cells (ATCC CRL 1651), HeLa cells (ATCC CCL 2), C1271 (ATCC CRL 1616), BS-C-1 (ATCC CCL 26) and MRC-5 (ATCC CCL 171).

Multimer Conjugate Production

Also provided herein is a method for producing a multimer conjugate or subunit thereof or polypeptide portion thereof which is capable of binding H-DNA and/or J-DNA, comprising culturing the host cell provided herein and recovering the produced polypeptide. The polypeptide can be encoded by a nucleic acid molecule provided herein. The method of producing a multimer conjugate, in some embodiments, can further comprise conjugating the polypeptide portion of the multimer conjugate to the scaffold, in embodiments wherein, for example, the scaffold is a non-polypeptide and/or the scaffold portion is produced separately. Methods for conjugating a polypeptide to another polypeptide or non-polypeptide material are know in the art and described herein.

Also provided is a process for producing cells capable of expressing a polypeptide provided herein which is capable of binding H-DNA and/or J-DNA, comprising genetically engineering cells in vitro by methods known in the art or by those described herein. The polypeptide can be encoded by a nucleic acid molecule provided herein. Numerous suitable methods exist in the art to produce polypeptides in appropriate hosts. If the host is a unicellular organism or a mammalian or insect cell, the person skilled in the art can revert to a variety of culture conditions that can be further optimized without an undue burden of work. The produced protein is harvested from the culture medium or from isolated (biological) membranes by established techniques. Furthermore, the produced polypeptide may be directly isolated from the host cell.

The polypeptides provided herein may be produced by microbiological methods or by transgenic mammals. Sometimes the polypeptide can be recovered from transgenic plants. Sometimes polypeptides and/or conjugates provided herein can be produced synthetically or semi-synthetically. For example, chemical synthesis, such as the solid phase procedure described by Houghton Proc. Natl. Acad. Sci. USA (82) (1985), 5131-5135, can be used. Another method is in vitro translation of mRNA. Some methods involve the recombinant production of protein in host cells as described above. For example, nucleotide acid sequences comprising all or a portion of any one of the nucleotide sequences provided herein can be synthesized by PCR, inserted into an expression vector, and a host cell transformed with the expression vector. Thereafter, the host cell is cultured to produce the desired polypeptide, which is isolated and purified. Protein isolation and purification can be achieved by any one of several known techniques; for example and without limitation, ion exchange chromatography, gel filtration chromatography and affinity chromatography, high pressure liquid chromatography (HPLC), reversed phase HPLC, preparative disc gel electrophoresis. In addition, cell-free translation systems can be used to produce the polypeptides provided herein. Suitable cell-free expression systems for use herein include rabbit reticulocyte lysate, wheat germ extract, canine pancreatic microsomal membranes, *E. coli* S30 extract, and coupled transcription/translation systems such as the TNT-system (Promega). These systems allow the expression of recombinant polypeptides or peptides upon the addition of cloning vectors, DNA fragments, or RNA sequences containing coding regions and appropriate promoter elements. Protein isolation/purification techniques may require modification of the proteins provided herein using conventional methods, as described above. For example, a histidine tag can be added to the protein to allow purification on a nickel column. Other modifications may cause higher or lower activity, permit higher levels of protein production, or simplify purification of the protein. After production of the polypeptide and/or conjugate it may be modified by pegylation, derivatization and the like.

Antibodies

Provided herein is an antibody that specifically binds to the multimer conjugate or conjugate subunit thereof or polypeptide portion thereof provided herein. In some cases the multimer conjugate or conjugate subunit thereof or polypeptide portion thereof has the capability to bind to H-DNA and/or J-DNA. The term "specifically" in this context means that the antibody reacts with the polypeptide or conjugate provided herein, but not with only portions of the polypeptide, e.g., with the J-DNA binding domain, the Fc portion of a scaffold comprising an Fc domain, or a leader or secretion sequence. In some embodiments, the antibody could specifically bind to the polypeptide linker of the multimer conjugate provided herein, if such a polypeptide linker is present.

Accordingly, the antibody binds specifically, for example, to a portion of the J-DNA binding domain and the scaffold (e.g. the Fc portion of the scaffold) or to a portion of the J-DNA binding domain and the linker polypeptide or to a portion of the linker polypeptide and the scaffold, or, as mentioned above, only to the linker polypeptide. Whether the antibody specifically reacts as defined herein above can easily be tested by comparing the binding reaction of the antibody with the portions as mentioned above and with only the respective portion(s) of the polypeptide or conjugate provided herein.

The antibody provided herein can be, for example, polyclonal or monoclonal. The term "antibody" also comprises derivatives or fragments thereof which still retain the binding specificity. Techniques for the production of antibodies are well known in the art and described, e.g. in Harlow and Lane "Antibodies, A Laboratory Manual", CSH Press, Cold Spring Harbor, 1988. These antibodies can be used, for example, for the immunoprecipitation and immunolocalization of the multimer conjugates and fragments thereof as well as for the monitoring of the presence of such multimer conjugates and fragments thereof, for example, in recombinant organisms or in diagnosis. They can also be used for the identification of compounds interacting with the proteins provided herein. For example, surface plasmon resonance as employed in the BIAcore system can be used to increase the efficiency of phage antibodies which bind to an epitope of the conjugate provided herein (Schier, Human Antibodies Hybridomas 7 (1996), 97-105; Malmborg, J. Immunol. Methods 183 (1995), 7-13). Antibodies include chimeric, single chain and humanized antibodies, as well as antibody fragments, such as, Fab fragments. Antibody fragments or derivatives further comprise F(ab')2, Fv or scFv fragments; see, for example, Harlow and Lane, loc. cit. Various procedures are known in the art and may be used for the production of such antibodies and/or fragments. Thus, the (antibody) derivatives can be produced by peptidomimetics. Further, techniques described for the production of single chain antibodies (see, inter alia, U.S. Pat. No. 4,946,778) can be adapted to produce single chain antibodies to polypeptide(s) and/or conjugates provided herein. Also, transgenic animals may be used to express humanized antibodies to the conjugates provided herein. In some embodiments, the antibody is a monoclonal antibody. For the preparation of monoclonal antibodies, any technique which provides antibodies produced by continuous cell line cultures can be used. Examples for such techniques include the hybridoma technique (Kohler and Milstein Nature 256 (1975), 495-497), the trioma technique, the human B-cell hybridoma technique (Kozbor, Immunology Today 4 (1983), 72) and the EBV-hybridoma technique to produce human monoclonal antibodies (Cole et al., Monoclonal Antibodies and Cancer Therapy, Alan R. Liss, Inc. (1985), 77-96). Techniques describing the production of single chain antibodies (e.g., U.S. Pat. No. 4,946,778) can be adapted to produce single chain antibodies to immunogenic polypeptides as described above. Furthermore, transgenic mice may be used to express humanized antibodies directed against the immunogenic polypeptides. In some embodiments, the antibodies/antibody constructs as well as antibody fragments or derivatives to be employed herein can be expressed in a cell. This may be achieved by direct injection of the corresponding protein molecules or by injection of nucleic acid molecules encoding the proteins. Furthermore, gene therapy approaches are contemplated. Accordingly, as used herein, the term "antibody molecule" relates to full immunoglobulin molecules as well as to parts of such immunoglobulin molecules. Furthermore, the term relates, as discussed above, to modified and/or altered antibody molecules, like chimeric and humanized antibodies. The term also relates to monoclonal or polyclonal antibodies as well as to recombinantly or synthetically generated/synthesized antibodies. The term also relates to intact antibodies as well as to antibody fragments thereof, like, separated light and heavy chains, Fab, Fab/c, Fv, Fab', F(ab') 2. The term "antibody molecule" also comprises bifunctional antibodies and antibody constructs, like single chain Fvs (scFv) or antibody-fusion proteins. It is also contemplated herein that the term "antibody" comprises antibody constructs which may be expressed in cells, e.g. antibody constructs which may be transfected and/or transduced via, inter alia, viruses or vectors. In some embodiments, the antibody can be coupled, linked or conjugated to detectable substances as described herein above in connection with the scaffold of the conjugate provided herein.

Compositions

Provided herein are compositions comprising the nucleic acid molecule, the vector, the host cell, the antibody, the polypeptide and/or the multimer conjugate described herein. The term "composition", as used in herein, relates to composition(s) which comprise(s) at least one of the aforementioned compounds. In some embodiments, the compositions comprise the aforementioned compounds in any combination. Compositions may, optionally, comprise further molecules which are capable of binding H-DNA and/or J-DNA. The composition may be in solid, liquid or gaseous form and may be in the form of (a) powder(s), (a) tablet(s), (a) solution(s), (an) aerosol(s), granules, pills, suspensions, emulsions, capules, syrups, liquids, elixirs, extracts, tincture or fluid extracts or in a form which is particularly suitable for oral or parental or topic administration.

Kits

Provided herein is a kit comprising the nucleic acid molecule, the vector, the host, the antibody, the polypeptide and/or the multimer conjugate provided herein. In some cases, the kit further comprises, optionally (a) reaction buffer(s), storage solutions and/or remaining reagents or materials required for the conduct of scientific or diagnostic assays or the like. Furthermore, parts of the kit provided herein can be packaged individually in vials or bottles or in combination in containers or multicontainer units.

The kit provided herein may be used for carrying out the method for isolating, enriching, purifying and/or detecting H-DNA and/or J-DNA as described herein and/or it could be employed in a variety of applications referred herein, e.g., as diagnostic kits, as research tools or therapeutic tools. Additionally, the kit provided herein may contain means for detection of H-DNA and/or J-DNA suitable for scientific, medical and/or diagnostic purposes. The manufacture of the kits can follow standard procedures which are known to the person skilled in the art.

Applications

The multimer conjugates provided herein can be used as a suitable diagnostic tool for isolating, enriching and/or detecting H-DNA (or in some cases, its precursor hydroxymethylcytosine DNA) and/or J-DNA from more than 10 ng, less than 10 ng, less than 7.5 ng, less than 5 ng, less than 2.5 ng, less than 1 ng, less than 0.1 ng, or from about 0.01 ng in a sample. In some embodiments, the H-DNA precursor, hydroxymethylcytosine DNA, can be isolated, enriched and/or detected after it has been subjected to glycosylation whereby it forms H-DNA. Accordingly, provided herein is a diagnostic composition, optionally further comprising suitable means for detection. A further embodiment is the use of the multimer conjugates for the detection of H-DNA and/or J-DNA. In addition, the nucleic acid molecules, the polypeptides and/or multimer conjugates, the vector, the host cell or the antibody provided herein can be used for the preparation of a diagnostic composition for detecting H-DNA and/or J-DNA. Moreover, the nucleic acid molecules, the polypeptide and/or multimer conjugates, the vector, the host cell or the antibody provided herein can be used for the preparation of a diagnostic composition for the detection of tumorous tissue or tumor cells. Moreover, the nucleic acid molecules, the polypeptides and/or multimer conjugates, the vector, the host cell or the antibody provided herein can be used for the preparation of a diagnostic composition for the detection of a pathogen or parasitic disease, such as, for example, a pathogenic protozoa. In some embodiments, the pathogenic protozoa is a kinetoplastid flagellate. Examples of kinetoplastid flagellate species are known in the art and are provided herein.

Provided herein is an in vitro method for detecting H-DNA and/or J-DNA comprising (a) contacting a sample comprising H-DNA and/or J-DNA with the multimer conjugate provided herein; and (b) detecting the binding of the conjugate to H-DNA and/or J-DNA. In some embodiments, the in vitro method is reverse South-Western blotting, immune precipitation, or affinity purification of H-DNA and/or J-DNA. The in vitro method also can be any procedure in which the multimer conjugate provided herein is linked to a solid matrix, for example, a matrix such as sepharose, agarose, capillaries, and vessel walls. In some embodiments, the in vitro methods further comprise as step (c) analyzing the H-DNA and/or J-DNA, for example, by sequencing, Southern Blot, microarrays, restriction enzyme digestion, bisulfite sequencing, pyrosequencing, PCR or MB-PCR. Analyzing H-DNA and/or J-DNA which has been isolated, enriched, purified and/or detected by using the multimer conjugates provided herein is not limited to the methods described herein, but encompasses all methods known in the art for analyzing H-DNA and/or J-DNA.

In one example of a diagnostic application of the multimer conjugates provided herein, MB-PCR is employed. Briefly, in a first step the multimer conjugate is added into a coatable PCR-vessel, for example, TopYield Strips from Nunc. In doing so, the multimer conjugate coated onto the inner surface of the vessel by techniques known in the art. In a next step, blocking reagents, e.g., 4.5% milk powder, are added into the coated PCR vessel. In a further step, DNA fragments of interest (for example, H-DNA and/or -DNA fragments) are added into the coated and blocked PCR vessel, which can bind to the multimer conjugate-coated vessel wall. In a following step, the coated and blocked PCR vessel containing DNA-fragments is incubated and then washed to remove unbound DNA-fragments. Afterwards, a PCR mix including gene-specific primers or at least two, three, four, five, six, seven etc. pairs of primers for, e.g., multiplex PCR for the gene or gene locus or gene loci of interest which is/are suspected to contain H-DNA and/or J-DNA, is added to run, for example, a real time PCR or conventional PCR followed by gel electrophoresis to separate amplification products.

The multimer conjugates provided herein can be useful for the detection of H-DNA and/or J-DNA in a sample as described herein below which may include (a) single cell(s). In some cases, the multimer conjugates provided herein can be useful for whole cells. "Whole cell" means the genomic context of a whole single cell. Thus, it could be useful for a genome-wide analysis of H-DNA and/or J-DNA. Such a method comprises an enriching/purifying step of H-DNA and/or J-DNA using the multimer conjugates provided herein and a detection step, e.g., hybridization of genomic DNA microarrays, tiling arrays, low-density arrays or lab-on-a-chip-approaches. Furthermore, the multimer conjugate provided herein may be particularly useful in the detection of H-DNA and/or J-DNA on single gene level. Such a method often comprises the step of enriching and/or purifying an H-DNA and/or J-DNA single gene and the step of detecting the H-DNA and/or J-DNA by employing PCR, real-time PCR and the like.

Another possible diagnostic application of the multimer conjugate provided herein is immunohistochemistry. Accordingly, the multimer conjugate can be used to "stain" H-DNA and/or J-DNA. Either the multimer conjugate is, via its scaffold, coupled, linked or conjugated to a suitable detectable substance as described herein or, for example, an antibody is used for detecting the multimer conjugate when bound to H-DNA and/or J-DNA.

As described herein, H-DNA can be generated from the glucosylation of 5-hydroxymethylcytosine (5hmC). Thus, in some embodiments, malignancies (i.e. cancers) can be detected by the methods provided herein by their 5-hydroxymethylcytosine (5hmC) pattern/profile, for example, which may, in some cases, be of a prognostic and/or predicable value. In some cases, the 5hmC pattern can be used to establish a pharmacologic profile for a patient. For example, the susceptibility and/or sensitivity to, e.g., an anti-cancer drug can be determined in some cases if it is detected that certain oncogenes and/or tumor suppressor genes contain certain 5hmC profiles.

The methods provided herein may be useful, in some embodiments, for identifying genomic loci and/or genes which contain certain 5hmC profiles in a malignancy such as cancer or a tumorous disease. The methods provided herein also may be useful, in some embodiments, for providing the basis for assaying the 5hmC status of such genomic loci and/or genes on a single gene level. In some cases, the malignancies are tumors. The tumor can be any possible type of tumor. Examples are skin, breast, brain, cervical carcinomas, testicular carcinomas, head and neck, lung, mediastinum, gastrointestinal tract, genitourinary system, gynecological system, breast, endocrine system, skin, childhood, unknown primary site or metastatic cancer, a sarcoma of the soft tissue and bone, a mesothelioma, a melanoma, a neoplasm of the central nervous system, a lymphoma, a leukemia, a paraneoplastic syndrome, a peritoneal carcinomastosis, a immunosuppression-related malignancy and/or metastatic cancer etc. The tumor cells may, e.g., be derived from: head and neck, comprising tumors of the nasal cavity, paranasal sinuses, nasopharynx, oral cavity, oropharynx, larynx, hypopharynx, salivary glands and paragangliomas, a cancer of the lung, comprising non-small cell lung cancer, small cell lung cancer, a cancer of the mediastinum, a cancer of the gastrointestinal tract, comprising cancer of the esophagus, stomach, pancreas, liver, biliary tree, small intestine, colon, rectum and anal region, a cancer of the genitourinary system, comprising cancer of the kidney, urethra, bladder, prostate, urethra, penis and testis, a gynecologic cancer, comprising cancer of the cervix, vagina, vulva, uterine body, gestational trophoblastic diseases, ovarian, fallopian tube, peritoneal, a cancer of the breast, a cancer of the endocrine system, comprising a tumor of the thyroid, parathyroid, adrenal cortex, pancreatic endocrine tumors, carcinoid tumor and carcinoid syndrome, multiple endocrine neoplasias, a sarcoma of the soft tissue and bone, a mesothelioma, a cancer of the skin, a melanoma, comprising cutaneous melanomas and intraocular melanomas, a neoplasm of the central nervous system, a cancer of the childhood, comprising retinoblastoma, Wilm's tumor, neurofibromatoses, neuroblastoma, Ewing's sarcoma family of tumors, rhabdomyosarcoma, a lymphoma, comprising non-Hodgkin's lymphomas, cutaneous T-cell lymphomas, primary central nervous system lymphoma, and Hodgkin's disease, a leukemia, comprising acute leukemias, chronic myelogenous and lymphocytic leukemias, plasma cell neoplasms and myelodysplastic syndromes, a paraneoplastic syndrome, a cancer of unknown primary site, a peritoneal carcinomastosis, a immunosuppression-related malignancy, comprising AIDS-related malignancies, comprising Kaposi's sarcoma, AIDS-associated lymphomas, AIDS-associated primary central nervous system lymphoma, AIDS-associated Hodgkin's disease and AIDS-associated anogenital cancers, and transplantation-related malignancies, a metastatic cancer to the liver, metastatic cancer to the bone, malignant pleural and pericardial effusions and malignant ascites. In some cases, the cancer or tumorous disease is cancer of the head and neck, lung, mediastinum, gastrointestinal tract, genitourinary system, gynecological system, breast, endocrine system, skin, childhood, unknown primary site or metastatic cancer, a sarcoma of the soft tissue and bone, a mesothelioma, a melanoma, a neoplasm of the central nervous system, a lymphoma, a leukemia, a paraneoplastic syndrome, a peritoneal carcinomastosis, a immunosuppression-related malignancy and/or metastatic cancer, AML, plasmacytoma or CLL.

The diagnostic composition provided herein comprises at least one of the herein described compounds provided herein. The diagnostic composition may be used, for example, in methods for isolating, enriching and/or determining the presence H-DNA and/or J-DNA, for example, in a sample as described above. As used herein, the term "sample" includes any biological sample obtained from an individual, cell line, tissue culture, or other source containing polynucleotides or polypeptides or portions thereof. Biological samples include body fluids (such as blood, sera, plasma, urine, synovial fluid and spinal fluid) and tissue sources found to express polynucleotides comprising H-DNA and/or J-DNA. Methods for obtaining tissue biopsies and body fluids from mammals are well known in the art. A biological sample which includes genomic DNA, mRNA or proteins can be a source. As used herein, a sample can also include any substance where parasitic protozoa might be found, such as for example, a biological sample obtained from an individual (e.g. human or livestock) or a sample obtained from a food source, crop, body of water (e.g. river, lake, stream, ocean, well), or drinking water source.

The diagnostic composition provided herein optionally comprises suitable means for detection. The nucleic acid molecule(s), vector(s), host(s), antibody(ies), polypeptide(s) and multimer conjugate(s) described above are, for example, suitable for use in immunoassays in which they can be utilized in liquid phase or bound to a solid phase carrier. Examples of well-known carriers include glass, polystyrene, polyvinyl ion, polypropylene, polyethylene, polycarbonate, dextran, nylon, amyloses, natural and modified celluloses, polyacrylamides, agaroses, and magnetite. The nature of the carrier can be either soluble or insoluble.

Solid phase carriers are known to those in the art and may comprise polystyrene beads, latex beads, magnetic beads, colloid metal particles, glass and/or silicon chips and surfaces, nitrocellulose strips, membranes, sheets, duracytes and the walls of wells of a reaction tray, plastic tubes or other test tubes. Suitable methods of immobilizing nucleic acid molecule(s), vector(s), host(s), antibody(ies), aptamer(s), polypeptide(s), conjugate(s) etc. on solid phases include but are not limited to ionic, hydrophobic, covalent interactions or (chemical) crosslinking and the like. Examples of immunoassays which can utilize the compounds herein are competitive and non-competitive immunoassays in either a direct or indirect format. Commonly used detection assays can comprise radioisotopic or non-radioisotopic methods. Examples of such immunoassays are the radioimmunoassay (RIA), the sandwich (immunometric assay) and the Northern or Southern blot assay. Furthermore, these detection methods comprise, inter alia, IRMA (Immune Radioimmunometric Assay), EIA (Enzyme Immuno Assay), ELISA (Enzyme Linked Immuno Assay), FIA (Fluorescent Immuno Assay), and CLIA (Chemioluminescent Immune Assay). Furthermore, the diagnostic compounds provided herein may be are employed in techniques like FRET (Fluorescence Resonance Energy Transfer) assays.

Appropriate labels and methods for labeling are known in the art. Examples of the types of labels which can be used herein include inter alia, fluorochromes (like fluorescein, rhodamine, Texas Red, etc.), enzymes (like horse radish peroxidase, β-galactosidase, alkaline phosphatase), radioactive isotopes (like 32 P, 33 P, 35 S or 125 I), biotin, digoxygenin, colloidal metals, chemi- or bioluminescent compounds (like dioxetanes, luminol or acridiniums). A variety of techniques are available for labeling biomolecules, are well known in the art and are considered to be within the scope herein and comprise, inter alia, covalent coupling of enzymes or biotinyl groups, phosphorylations, biotinylations, random priming, nick-translations, tailing (using terminal transferases). Such techniques are, e.g., described in Tijssen, "Practice and theory of enzyme immunoassays", Burden and von Knippenburg (Eds), Volume 15 (1985); "Basic methods in molecular biology", Davis L G, Dibmer M D, Battey Elsevier (1990); Mayer, (Eds) "Immunochemical methods in cell and molecular biology" Academic Press, London (1987); or in the series "Methods in Enzymology", Academic Press, Inc. Detection methods comprise, but are not limited to, autoradiography, fluorescence microscopy, direct and indirect enzymatic reactions, etc.

EXAMPLES

The examples set forth below illustrate certain embodiments and do not limit the technology.

Example 1

Examples of Sequences

Provided hereafter are non-limiting examples of certain amino acid sequences.

TABLE 1

Examples of Sequences

| Name | SEQ ID NO | Sequence |
|---|---|---|
| L. tarentolae JBP1 (GenBank accession no. Q9U6M1) | 1 | mepdskkvkldifnfpttretrtpeevaesyaeavkshpfydnvhsvvdfydsgtikdgr gqiigvvlrealpkyaasmaselltsaavrtslrsmmfggepplsgiagyfdyrgspvel ksrktsftyeheaawpavfpvvdyvseiyrhvaperwkaqndaipdlvrihgtpfstlti nsrfrtashtdvgdfdagysciacldgqfkglalsfddfginvllqprdvmifdshhfhs ntevelsfsgedwkrltcyfyyraalgepasyaeyqrrleksktdtrftpvvhhvrvken gtsvnrpspvypisqspfwvpmvahclqhcasaaqcvheamtadgsrlaemmfgeslsts dgiplrgedekvkangdstprplsrlggfsetnlmvstavekkkyldsefllhcisaqll dmwkqararwlelvgkewahmlalnperkdflwknqsemnsaffdlcevgkqvmlgllgk evalpkeeqafwimyavhlsaacaeelhmpevamslrklnvklkdfnfggtryfkdmppe ekkrrmerkqrieearrhgmpsgshekranwltndsfdyqtedcvidyaqhkwvlpalha |

TABLE 1-continued

Examples of Sequences

| Name | SEQ ID NO | Sequence |
|---|---|---|
| | | kevtktvrtgelpttervvrvlvvipdpqsklenvdcklevpdmvgsssewerlmsspav hrvlsaaqrnlqlpdsvthgnvqthfafhstlptdiydfvvlqhvlsripddaqasayir raaalcsgclfvvetdvqcrqyytlkysircsydtvaplffqqlhrvcygtktarvrtkg elesliptvccaryklqgsplnttvhvvspfpscevqnlssalcdra |
| L. aethiopica JBP1 (partial sequence) | 2 | sdgiplrgeenklkansdsaprplsrlggfsetnlmvstavekkkylnseflshfisaqll dmwkqargkwlelvgrewthmlalnperkdflwknqsemnsaffdlcevgkqvm lgllgkevalpkeeqafwtmyavhlntacaeeelhmphvamslrklnvklkdfnfggtr yfkdmppeeqkrrmerkqrieearrhgmssgahekranwltndsfdyqtedcvvd yaqhkwpppalhareitknvrtgel |
| L. braziliensis JBP1 (GenBank accession no. XP_001562766) | 3 | messtkrikmdifnfptiketrtpeevaesyaeavklhpfydnahcvidfydsgtikdgr geiigvvlrkalpkyatsmasallisaavrtslrsmifggesplsgiagyfdyrgspvel ksrktsftyeheeawsavfpvvdyvseiyrhvaperwkaqnnaipdlvrihgtpfstlti nsrfrtashtdvgdfdagysciacidgkfkglaltfddfrinvlmqprdvmvfdshhfhs ntevevscseedwkrltcyfyyrtalgepssyaeyrrrlekskqdpsftpvvsnvmmken gtnlnrpspvhpvppspfwlpmlahclqhcasaaqsvheamtadgsqlaeiifgeplsts dgiplrgddeklkangdtgakplsrlggfsetdlmvstaaekrkyldseflshcisaqll dmwkqararwlelvgkewkhmltlnperkdflwknrsemnsaffdlcevgkqvmlglldk eaalpkeeqafwtmyavhlsaacaeeelhmphdamslrklnvklkdfnfggtryfkdmppe eqqrrmerkgrieearrhgmtgahekranwltndsgriedyqtedcvvdyakhkwvlperhak avtknyhtawlptreevvrvlvvlpdlqirvegvdcklekpdtvedssewvrrlvsspavh rllaaaqrnlqlpddvmhgnihirfvfhstlptdmydfvvlqhvlsripddvlassyitr aaalcsgclfveetdvqcrqyytlkysirrnydavaphffqqlhqasygtkmarvrtkge lealiptvccaryklqgsplnttihvvsptaph |
| L. donovani JBP1 (GenBank accession no. CBZ32114) | 4 | mepdpkkvkldifdfptaretrtpeevaesyaeavkshpfydnvhsaidfydsgtikdgr gqiigvvlrealpkyaasmasellasaavrtslrsmmfggesplsgiagyfdyrgspvel ksrktsftyeheaawpavfpvvdyvselyrhvaperwkaqndaipdvvrihgtpfstlti nsrfrtashtdvgdfdggysciacldgqfkglalafddfginvlmqprdvmifdshhfhs ntevelsfsgedwkrltcyfyyraalgepasyaeyrrrlekskqdtsftpvvsnvrvken gtnlnrpspvypiflspfwvpmvahclqhcaseaqcvhdamtadgsrlaevmfgeplsts dgiplrgeeeklkansdsasrplsrlggfsetnlmvstavekkkylnseflshfisaqll dmwkqargkwlelvgrewthmlalnperkdflwknqsemnsaffdlcevgkqvmlgllgk eaalpkeeqafwtmyavhlnaacaeeelnmphvamslrklnvklkdfnfggtryfkdmppe eqkrrmerkgrieearrhgmssgahekranwltndsfdyqtedcvvdyaqhkwvppalha keitknvrsgelptregvvrvlvvlpdpqskvdcvdcklevsetvrcscewerlmsspav hrvlaaaqrnlqlpdsvthdnieirfafhsrlptdmcdfvvlqhvlscipddvlasayir rsaalcsgcfvvvetdvqcrqyytlkcsvrcdydavaplffqqlhrvsygtkaarvrtkg elesliptvccaryklqgsplnttvhvvapappr |
| L. infantum JBP1 (GenBank accession no. XP_001463611) | 5 | mepdpkkvkldifdfptaretrtpeevaesyaeavkshpfydnvhsaidfydsgtikdgr gqiigvvlrealpkyaasmasellasaavrtslrsmmfggesplsgiagyfdyrgspvel ksrktsftyeheaawpavfpvvdyvselyrhvaperwkaqndaipdvvrihgtpfstlti nsrfrtashtdvgdfdggysciacldgqfkglalafddfginvlmqprdvmifdshhfhs ntevelsfsgedwkrltcyfyyraalgepasyaeyrrrlekskqdtsftpvvsnvrvken gtnlnrpspvypiflspfwvpmvahclqhcaseaqcvhdamtadgsrlaevmfgeplsts dgiplrgeeeklkansdsasrplsrlggfsetnlmvstavekkkylnseflshfisaqll dmwkqargkwlelvgrewthmlalnperkdflwrnqsemnsaffdlcevgkqvmlgllgk eaalpkeeqafwtmyavhlnaacaeeelnmphvamslrklnvklkdfnfggtryfkdmppe eqkrrmerkgrieearrhgmssgahekranwltndsfdyqtedcvfdyaqhkwvppalha keitknvrsgelptregvvrvlvvlpdpqskvdcvdcklevsetvrcscewerlmsspav hrvlaaaqrnlqlpdsvthdnieirfafhsrlptdmcdfvvlqhvlscipddvlasayir rsaalcsgcfvvvetdvqcrqyytlkcsvrcdydavaplffqqlhrvsygtkaarvrtkg elesliptvccaryklqgsplnttvhvvapappr |
| L. major strain Friedlin JBP1 (GenBank accession no. XP_001681321) | 6 | mepdpkkikldifnfptaretrtpeevaesyaeavkshpfydnvhsvidfydsgtikdgr gqiigvvlrealpkyavsmasellasaavrtslrsmmfggesplsgiagyfdyrgspvel ksrktsftyeheaawpavfpvvdyvselyrhvaperwkaqndaipdvvrihgtpfstlti nsrfrtashtdvgdfdggysciacldghfkglalafddfginvlmqprdvmifdshhfhs ntevelsfsgedwkrltcyfyyraalgepasyaeyqrrlekskqdnsftpvvsnvrvken gtnlnrpspvypicpspfwvpmvahclqhcaseaqcvhdamtadgsrlaevmfgeplsts dgiplrgedkklkansdsasrplsrlggfsetnlmvstavekkkylnseflshfisaqll dmwkqargkwlelvgrewthmlalnperkdflwknqsemnsaffdlcevgkqvmlgllgk evalpkeeqafwtmyavhlnaacaeeelhmphvamslrklnvklkdfnfggtryfkdmppe eqkrrmerkgrieearrhgmssgahekranwltndsfdyqtedcvvdyaqhkwpppalha keitknvrtgelptregvvrvlvvlpdpqsklecvdcklevpetvrcscewerlmsslav rrvlaaaqrnlqlpgsvthgnieirfafhsrlptdmcdfvvlqhvlscipddvlasayir raaalctgcvyvvetdvqcrqyytlkcaarcdydavaslffqqlhrvsygtkaarvrtkg elesliptvccaryklqgsplnttvhvvspapsr |

TABLE 1-continued

Examples of Sequences

| Name | SEQ ID NO | Sequence |
| --- | --- | --- |
| L. Mexicana JBP1 (GenBank accession no. CBZ24305) | 7 | mepdskkvkldifsfptaretrtpeevaesyaeavkshpfydnvhsvidfydsgtikdgr gkiigvvlrealpkyatsmaselltsaavrtslrsmmfggesplsgiagyfdyrgspvel ksrktsftyeheaewpavfpvidyvselyrhvapkqwkaqndaipdlvrihgtpfstlti nsrfrtashtdvgdfdggysciacldgqfkglalaldsfginvlmqprdvmifdshhfhs ntevelsfsgedwkrltcyfyyraalgepasyaeyrrrlekskqdtsftpavsnvrvken dtnlnrpspvypishspfwvpmvahclqhcasaaqcvhdamtadgsrlaevmfgeplstl dgiplrredeklkangdsasrplsrlggfsetnlmvttavekkkylnseflshgisaqll nmwkqarakwlelvsrewthmialnperkdflwknqsemnsaffdlcevgkqvmlgllgk eaalpkeeqafwtmyavhlnaacaeelhmphaamslhklnvklkdfnfggtryfkdmppe eqkrrverkgrieearrhgmssgshekranwltndsfdyqtedcivdyaqhkwyppavha keitknvrtgelptreglvrvlvvlpdpqskvkcvdcklevpetlrcssewerlmsslav hrvlaavqrnlqlpdsvtqgniqihfafhstlptavydfvvlqhvlscipedvlaseyir raaalcsgclfvaetdvqcrqyytlkcavrcdydtvaplffqqlhqasygtkaarvrtkg elesliptvccaryklkgsplnttvhvvspapps |
| C. fasciculata JBP1 (GenBank accession no. AAF01742) | 8 | mepkskkvkqdifnfpdgkdvpttkekaeayvdalkahpfydnvhsvvdvydsatlrdgk grvigymlrkalpehattaasgllsaaavrtslrssmfggesplsgiagyfdyrgspvel karktaftyehekkwpavfplvdyvseiyksvmpehwaaqdsaipdivrihgtpfstlti nsrfrtashtdagdfdggysciacidgdfkglalgfddfhvnvpmqprdvlvfdshyfhs nseleiscpteewrrltcyfyyrsalgepssyaeyrrrlaaaqqdstaqpvvssvvekpn gknlykpstvfpidptpfavvaqlhrlhhcaakglcvhellavpssplavllfgerlscs dgiplraaeqklkanadgasrgvtssggfsesdavlttavekskylerdhlsqcisaell amwvearkhwlrlvatewarmiatapertdflwknkspmntaffdlcevakqvmlglldk etatpteerhfwsvyaahlhracaerlmmpeeamslrklnvklkdfsfggtryfkdmpve eqkrrvarkasieearrrstaakdgeqrsnwltndafdyqtedcevdyaghgwavpkqha ktvtanvhqeavaatteavrvlvvlprppsgdrgdaavdlpkevttsaewvrlmsspavr rvlaakqrnltllpncnveavslnfayhdslpqkatfdfvvlqhvlsampedaiatdyvs rmrsictgclfvvetdvqcrqyftlhyplrvqydavapaffqllhrcsygtplartrtka evealfpfvccaryklqgspmntvvhllale |
| T. brucei JBP1 (GenBank accession no. XP_829420) | 9 | mrrqvkkvlrekaddsmkpgwdvyqpsndvvyafnhymqgsqidaearekaekafqeavk khpfhnnadhtvdfhgttvfrnakgkvcgvlipkalpsfatsmaadvlecavartslrsa lfggvspnsgiagyfdyrgtpvelkcrktsftyehtkewrsvfpmidytsaiykaalpdh wkaqdaavpdvvrihgspfstltvnerfrtashtdngdfdngygvlavlkgeysglslal ddygvcfnmqptdvllfdthlfhsnteleakeanatwnrlscvfyyraalgeqpcveeyr rrlkkakeekstslsfnhieqkdngentnkpapvypvsltpfscaasawalrgcaaamlt rlhglvrenaslmtelfgepvevadglprrapeeiipvhkhtnvqmhylggfsekgdiln eamnkrhyldkenlqkmfgeefvniwtqsrthwlqlvkkewehqketnptrtrfswnnts amnfaffdlcdvakqlmcgafgdrevnkkeeqsfwgmfaahldnacineigmlqgsmgmh klnvklkdynfggtrylkdmppeeqerrrrrrleiegarrrapicdsesgdwlrneafdy qtedvavnyereqwitpennakrfgfpergvygaegaatgtisvlivlpkptnhrqktce lptsreadrimknpaaqrllcakpcniglstssnksrtvlcgniridkvfdggsvggkmy dfvimrhllaattgereplclvrwtslaryctfvvevdlldrhhyilkseigeeysavs eicfsalysatyardkvnlrttpcllsfidksgnmlesrfkfngsplntvafvvrrrek |
| T cruzi JBP1 (GenBank accession no. XP_815377) | 10 | mkqkrgkqdvkmvesappqllpkkgrleiselapqqrtirtaeeiemayneavrkhpfyd nadhtidfhdatvfrdargvvggvllpgalpafaatmaadvlrpaavrtslrsnmfggfa plsgiagyfdyrgspvelkcrktsftyenvhswpnvfpmidyvsaiykavfperwaaqda avpdivrihgspfstltvnqqfrtashtdagdfdmgygllavlegkfeglslalddfgvc frmqprdvlifnthffhsntepelnhpkddwsrltcvcyyraalgepacvaeyerrlara keigaspppavdailqkdngnnfnkpaptftysltpfggaasicslhcctakllrlhell lenptlevilfgeslrtddglprrekeqlisvhlpvvvkmspsggfselggalkaaeekq yffeekyladelgpdlmsmwtqsrahwlrlvkedwerlcrrdpertkftwnnssamnaaf fdlcevakqmmigllnketpssaenhsfwilfaahlnyacttengmprdavgmhklnvkl kdfhfggtrylkdmppeeqerrlerkkrieearrrgnaarethtdnwllndtfdyqqedr kvefeengwmtpeayvkhlglkpcgdvtaaaspteihvlvvlprpaaaapkdvkrdvpl atseesirllmnpaaqrvltgkarnvtlpsplsfggvkitvlfdgddidcihpdfvvlqh llaaieedeaakarvkywahvarycvfvvetdvrdrrhfllreevrvayedvaedcfrsl haaaystkcnrlrttpslialsnskniglakfrgsplntialivvgerld |
| T cruzi JBP1 (GenBank accession no. EAN90000) | 11 | mkqkrgkqdvkmlesappqllpkkgrleiselapqqrtirtaeeietayneavrkhpfyd nadhtidfhdatvfrdargvvggvflpgalpafaatmaadvlrpaavrtslrsnmfggfa plsgiagyfdyrgspvelkcrktsftyenvhswpnvfpmidyvsaiykavfpeqwaaqda avpdivrihgspfstltvnqqfrtashtdagdfdmgygllavlegkfeglslalddfgvc frmqprdilifnthffhsntepelnhprddwsrltcvcyyraalgepacvaeyerrlara keigaspppavdailqkdngnnfnkpaptfpylltpfggaasvcslhcctakllrlhell lenptlevilfgeslrtddglprrekeqlisvhlpvvvkmspsggfselggalkaaeekq yffeekyladelgpdlmsmwtqsrahwlrlvkedwerlcrrdpertkftwnnssamnaaf fdlcevakqmmigllnketpssaenhsfwilfaahlnyacttengmprdavgmhklnvkl kdfhfggtrylkdmppeeqerrlerkkrieearrrgssahethtdnwllndtfdyqqedr kvefeengwmtpeayvkhlglkpcgdvtaaaspteihvlvvlprpaaaatakdakrdvp latseesirllmnpaaqrvlrgkarnvalpsplsfggvkitvlfdgddidcihpdfvilq hllatieedeaakarvkywarvarycvfvvetdvrdrrhfllreevrvayedvaedcfrs lhaaaystkynrlrttpslialcnrkniglrfkfrgsplntialvvvgerld |

TABLE 1-continued

Examples of Sequences

| Name | SEQ ID NO | Sequence |
|---|---|---|
| T cruzi JBP1 (GenBank accession no. EFZ24904) | 12 | fftmkqkrgkqdvkmlestppqllpkkgrleiselapqqrtirtaeeietayneavrkhp fydnadhtidfhdatvfrdargvvggvflpgalpafaatmaadvlrpaavrtslrsnmfg gfaplsgiagyfdyrgspvelkcrktsftyenvhswpnvfpmidyvsaiykavfpeqwaa qdaavpdivrihgspfstltvnqqfrtashtdagdfdmgygllvvlegkfeglslalddf gvcfrmqprdilifnthffhsnteleldhpgdewsrltcycyyraalgepacvaeyerrl arakeigaspppavdaiiqkdngnnfnkpaptftylltpfggaasvcslhcctakllrlh elllenpklevilfgeslrtddglprrekeqlisvhlpvvvkmspsggfselggalkaae ekqyffeekyladelgpdlmsmwtqsrahwlrlvkedwerlcrrdpertkftwnnssamn aaffdlcevakqmmigllnketpssaenhsfwilfaahlnyacatengmprdavgmhkln vklkdfhfggtrylkdmppeeqerrlerkkrieearrrgssahethtdnwllndkfdyqq edrkvefeengwmtpeayvkhlglkpcgdvtataspteshivlvvlprpvvaaaaakdak rdvplatseesirllmnpaaqrvltgkarnvtlpsplsfggvkitvlfdgddidcihpdf vilqhllaaieedeaakarvkywahvarycvfvvetdvrdrrhfllreevrvayedvaed cfrslhaaaystkynrlrttpslialcnrkniglrfkfrgsplntialivvgerld |

Example 2

Examples of Embodiments

A1. A composition comprising a multimer that comprises a scaffold conjugated to two or more polypeptides, which polypeptides specifically interact with a nucleic acid containing beta-D-glucosyl-hydroxymethylcytosine and/or a nucleic acid containing beta-D-g lucosyl-hydroxymethyluracil.

A1.1 The composition of embodiment A1, wherein the two or more polypeptides specifically interact with a nucleic acid containing beta-D-glucosyl-hydroxymethylcytosine.

A1.2 The composition of embodiment A1.1, wherein the nucleic acid containing beta-D-glucosyl-hydroxymethylcytosine is generated from nucleic acid containing 5-hydroxymethylcytosine.

A1.3 The composition of embodiment A1, wherein the two or more polypeptides specifically interact with a nucleic acid containing beta-D-glucosyl-hydroxymethyluracil.

A2. The composition of embodiment A1, wherein the scaffold is chosen from an antibody, an antibody fragment, a multimerized binding partner that interacts with a binding partner counterpart in each of the polypeptides, a polymer, and a polyfunctional molecule.

A2.1 The composition of embodiment A2, wherein the scaffold is coupled to a solid support.

A2.2 The composition of embodiment A2 or A2.1, wherein the scaffold is a multimerized ligand that interacts with an amino acid sequence in the polypeptides.

A3. The composition of embodiment A2, wherein the antibody fragment is an Fc portion of an antibody.

A3.1 The composition of embodiment A3, wherein the Fc portion of the antibody comprises two chains.

A3.2 The composition of embodiment A3, wherein the Fc portion of the antibody is a single chain.

A4. The composition of embodiment A1 or A2, wherein one or more of the polypeptides comprise a full-length native protein that specifically interacts with the beta-D-glucosyl-hydroxymethylcytosine in the nucleic acid and/or the beta-D-glucosyl-hydroxymethyluracil in the nucleic acid.

A5. The composition of embodiment A1 or A2, wherein one or more of the polypeptides comprise a fragment of a native protein that specifically interacts with the beta-D-glucosyl-hydroxymethylcytosine in the nucleic acid and/or the beta-D-glucosyl-hydroxymethyluracil in the nucleic acid.

A6. The composition of embodiment A1 or A2, wherein one or more of the polypeptides comprise a modified protein that specifically interacts with the beta-D-glucosyl-hydroxymethylcytosine in the nucleic acid and/or the beta-D-glucosyl-hydroxymethyluracil in the nucleic acid, which modified protein comprises one or more amino acid modifications to a full-length native protein.

A7. The composition of embodiment A1 or A2, wherein one or more of the polypeptides comprise a modified protein that specifically interacts with the beta-D-glucosyl-hydroxymethylcytosine in the nucleic acid and/or the beta-D-glucosyl-hydroxymethyluracil in the nucleic acid, which modified protein comprises one or more amino acid modifications to a fragment of a full-length native protein.

A8. The composition of any one of embodiments A4 to A7, wherein the native protein is from a kinetoplastid flagellate organism.

A9. The composition of embodiment A8, wherein the kinetoplastid flagellate organism is chosen from a *Trypanosoma* spp. organism, *Leishmania* spp. organism, *Crithidia* spp. organism and *Euglena* spp. organism.

A10. The composition of embodiment A9, wherein the *Trypanosoma* spp. organism is chosen from *T. brucei* and *T. cruzi*.

A11. The composition of embodiment A9, wherein the *Leishmania* spp. organism is chosen from *L. tarentolae, L. aethiopica, L. braziliensis, L. donovani, L. infantum, L. major* strain Friedlin and *L. mexicana*.

A12. The composition of embodiment A9, wherein the *Crithidia* spp. organism is *C. fasciculata*.

A13. The composition of any one of embodiments A8 to A12, wherein the native protein comprises a polypeptide sequence selected from SEQ ID NOs:1 to 12.

A14. The composition of any one of embodiments A8 to A12, wherein the fragment of the native protein comprises amino acids 382 to 561 of SEQ ID NO:1 or substantially identical polypeptide thereof.

A15. The composition of any one of embodiments A8 to A14, wherein the native protein or fragment of the native protein comprises an alpha helix 4 of *L. tarentolae* polypeptide or substantially identical polypeptide thereof.

A16. The composition of any one of embodiments A8 to A14, wherein the fragment of the native protein or fragment of the native protein comprises one or more amino acids chosen from amino acids at positions 387, 388, 389, 390, 391, 399, 402, 411, 423, 427, 430, 431, 433, 434, 438, 446, 448, 451, 453, 455, 457, 459, 560, 462, 463, 464, 465, 466, 467, 469, 471, 472, 474, 476, 487, 491, 492, 496, 498, 499, 502, 503, 509, 518, 519, 520, 521, 522, 523, 524, 525, 528, 529, 530, 531, 532, 533, 535, 536, 537, 538, 540, 541, 544, 545, 548, 552, 553, 555, 556, 557, 571, 572, 574, 577, 578, 579, 580, 582, 583 and 593 of *L. tarentolae*, or corresponding amino acids thereof.

A17. The composition of any one of embodiments A1 to A16, wherein the polypeptides in the multimer specifically bind to the nucleic acid containing beta-D-glucosyl-hydroxymethylcytosine and/or the nucleic acid containing beta-D-glucosyl-hydroxymethyluracil.

A18. The composition of any one of embodiments A1 to A17, wherein the two or more polypeptides in the multimer have the same amino acid sequence.

A19. The composition of any one of embodiments A1 to A17, wherein the two or more polypeptides in the multimer have different amino acid sequences.

A20. The composition of any one of embodiments A1 to A19, wherein the multimer is conjugated to one or more signal generating molecules.

A21. The composition of any one of embodiments A1 to A20, wherein the scaffold is a polypeptide.

A22. The composition of embodiment A21, wherein the scaffold, or portion thereof, and the polypeptides that specifically interact with a nucleic acid containing beta-D-glucosyl-hydroxymethylcytosine and/or a nucleic acid containing beta-D-glucosyl-hydroxymethyluracil contain amino acids and are contiguous.

B1. A nucleic acid comprising a polynucleotide that encodes a multimer of embodiment A22.

B2. An expression vector comprising a polynucleotide of embodiment B1.

B3. A cell comprising a nucleic acid of embodiment B1 or an expression vector of embodiment B2.

C1. A composition comprising a solid support to which a multimer of any one of embodiments A1 to A22 is conjugated.

D1. A method for manufacturing a multimer of any one of embodiments A1 to A21, which comprises conjugating the scaffold to the polypeptides that specifically interact with a nucleic acid containing beta-D-glucosyl-hydroxymethylcytosine and/or a nucleic acid containing beta-D-glucosyl-hydroxymethyluracil.

D2. A method for manufacturing a multimer of embodiment A22, which comprises expressing the multimer from a nucleic acid of embodiment B1 or an expression vector of embodiment B2.

D3. A method for manufacturing a multimer of embodiment A22, which comprises expressing the multimer in a cell of embodiment B3.

E1. A method for detecting the presence, absence or amount of nucleic acid containing beta-D-glucosyl-hydroxymethylcytosine and/or a nucleic acid containing beta-D-g lucosyl-hydroxymethyluracil in a sample, comprising contacting the sample that may contain nucleic acid containing beta-D-glucosyl-hydroxymethylcytosine and/or a nucleic acid containing beta-D-glucosyl-hydroxymethyluracil with a multimer of any one of embodiments A1 to A22;

determining the presence, absence or amount of the multimer that specifically interacts with the nucleic acid in the sample, whereby the presence, absence or amount of nucleic acid containing beta-D-glucosyl-hydroxymethylcytosine and/or a nucleic acid containing beta-D-glucosyl-hydroxymethyluracil in a sample is determined.

E2. The method of embodiment E1, which is performed in vitro.

The entirety of each patent, patent application, publication and document referenced herein hereby is incorporated by reference. Citation of the above patents, patent applications, publications and documents is not an admission that any of the foregoing is pertinent prior art, nor does it constitute any admission as to the contents or date of these publications or documents.

Modifications may be made to the foregoing without departing from the basic aspects of the technology. Although the technology has been described in substantial detail with reference to one or more specific embodiments, those of ordinary skill in the art will recognize that changes may be made to the embodiments specifically disclosed in this application, yet these modifications and improvements are within the scope and spirit of the technology.

The technology illustratively described herein suitably may be practiced in the absence of any element(s) not specifically disclosed herein. Thus, for example, in each instance herein any of the terms "comprising," "consisting essentially of," and "consisting of" may be replaced with either of the other two terms. The terms and expressions which have been employed are used as terms of description and not of limitation, and use of such terms and expressions do not exclude any equivalents of the features shown and described or portions thereof, and various modifications are possible within the scope of the technology claimed. The term "a" or "an" can refer to one of or a plurality of the elements it modifies (e.g., "a reagent" can mean one or more reagents) unless it is contextually clear either one of the elements or more than one of the elements is described. The term "about" as used herein refers to a value within 10% of the underlying parameter (i.e., plus or minus 10%), and use of the term "about" at the beginning of a string of values modifies each of the values (i.e., "about 1, 2 and 3" refers to about 1, about 2 and about 3). For example, a weight of "about 100 grams" can include weights between 90 grams and 110 grams. Further, when a listing of values is described herein (e.g., about 50%, 60%, 70%, 80%, 85% or 86%) the listing includes all intermediate and fractional values thereof (e.g., 54%, 85.4%). Thus, it should be understood that although the present technology has been specifically disclosed by representative embodiments and optional features, modification and variation of the concepts herein disclosed may be resorted to by those skilled in the art, and such modifications and variations are considered within the scope of this technology.

Certain embodiments of the technology are set forth in the claim(s) that follow(s).

What is claimed is:

1. A method for detecting the presence, absence or amount of nucleic acid containing beta-D-glucosyl-hydroxymethylcytosine and/or a nucleic acid containing beta-D-glucosyl-hydroxymethyluracil in a sample, comprising:
contacting the sample that may contain nucleic acid containing beta-D-glucosyl-hydroxymethylcytosine and/or a nucleic acid containing beta-D-glucosyl-hydroxymethyluracil with a multivalent multimer conjugate comprising two or more polypeptides selected from the group consisting of a full-length native J-DNA binding protein (JBP) or substantially identical polypeptide thereof, a J-DNA binding fragment of a full-length native JBP or substantially identical polypeptide thereof and a polypeptide comprising the J-DNA binding domain of a JBP or substantially identical polypeptide thereof, wherein each polypeptide in the multimer is directly conjugated to a scaffold, wherein the scaffold is an antibody or an antibody fragment, which polypeptides specifically interact with a nucleic acid containing beta-D-glucosyl-hydroxymethylcytosine and/or a nucleic acid containing beta-D-glucosyl-hydroxymethyluracil; and
determining the presence, absence or amount of the multimer that specifically interacts with the nucleic acid in the sample, whereby the presence, absence or amount of nucleic acid containing beta-D-glucosyl-hydroxymethylcytosine and/or a nucleic acid containing beta-D-glucosyl-hydroxymethyluracil in a sample is determined.

2. The method of claim 1, which is performed in vitro.

3. The method of claim 1, wherein the two or more polypeptides specifically interact with a nucleic acid containing beta-D-glucosyl-hydroxymethylcytosine.

4. The method of claim 1, wherein the two or more polypeptides specifically interact with a nucleic acid containing beta-D-glucosyl-hydroxymethyluracil.

5. The method of claim 1, wherein the scaffold is coupled to a solid support.

6. The method of claim 1, wherein the antibody fragment is an Fc portion of an antibody.

7. The method of claim 1, wherein one or more of the two or more polypeptides comprise one or more substantially identical polypeptides, wherein the one or more substantially identical polypeptides comprise modified JBP that specifically interacts with the beta-D-glucosyl-hydroxymethylcytosine in the nucleic acid and/or the beta-D-glucosyl-hydroxymethyluracil in the nucleic acid, which modified protein comprises one or more amino acid modifications to a full-length native JBP or to a J-DNA binding fragment of a full-length native JBP.

8. The method of claim 1, wherein one or more of the two or more polypeptides comprise one or more full-length native JBP from a kinetoplastid flagellate organism, a J-DNA binding fragment of a full-length native JBP from a kinetoplastid flagellate organism, or a polypeptide comprising the J-DNA binding domain of a JBP from a kinetoplastid flagellate organism, or substantially identical polypeptides thereof.

9. The method of claim 8, wherein the kinetoplastid flagellate organism is selected from the group consisting of *Trypanosoma* spp. organism, *Leishmania* spp. organism, *Crithidia* spp. organism and *Euglena* spp. organism.

10. The method of claim 8, wherein the native JBP comprises a polypeptide sequence selected from the group consisting of SEQ ID NOs: 1 to 11 and 12.

11. The method of claim 8, wherein a fragment of the native JBP comprises amino acids 382 to 561 of SEQ ID NO:1.

12. The method of claim 8, wherein the native JBP or a fragment of the native JBP comprises an alpha helix 4 of *L. tarentolae* polypeptide.

13. The method of claim 1, wherein the scaffold, or portion thereof, and the polypeptides that specifically interact with a nucleic acid containing beta-D-glucosyl-hydroxymethylcytosine and/or a nucleic acid containing beta-D-glucosyl-hydroxymethyluracil contain amino acids and are contiguous.

* * * * *